United States Patent
Russell et al.

(10) Patent No.: US 11,813,318 B2
(45) Date of Patent: Nov. 14, 2023

(54) BETA-2 MICROGLOBULIN-DEFICIENT CELLS

(71) Applicant: University of Washington through its Center for Commercialization, Seattle, WA (US)

(72) Inventors: David W. Russell, Seattle, WA (US); Roli K. Hirata, Seattle, WA (US)

(73) Assignee: UNIVERSITY OF WASHINGTON, Seattle, WA (US)

( * ) Notice: Subject to any disclaimer, the term of this patent is extended or adjusted under 35 U.S.C. 154(b) by 1116 days.

(21) Appl. No.: 16/507,589

(22) Filed: Jul. 10, 2019

(65) Prior Publication Data

US 2019/0381154 A1 Dec. 19, 2019

Related U.S. Application Data

(63) Continuation of application No. 14/111,837, filed as application No. PCT/US2012/034051 on Apr. 18, 2012, now abandoned.

(60) Provisional application No. 61/477,474, filed on Apr. 20, 2011.

(51) Int. Cl.
| | | |
|---|---|---|
| *A61K 35/28* | (2015.01) | |
| *C12N 5/10* | (2006.01) | |
| *C07K 14/74* | (2006.01) | |
| *A61K 39/00* | (2006.01) | |
| *A61K 35/12* | (2015.01) | |

(52) U.S. Cl.
CPC .......... *A61K 39/0005* (2013.01); *A61K 35/28* (2013.01); *C07K 14/70539* (2013.01); *A61K 35/12* (2013.01); *A61K 2039/515* (2013.01); *C07K 2319/00* (2013.01); *C12N 2740/17043* (2013.01); *C12N 2750/14143* (2013.01); *C12N 2800/30* (2013.01)

(58) Field of Classification Search
None
See application file for complete search history.

(56) References Cited

U.S. PATENT DOCUMENTS

| | | | |
|---|---|---|---|
| 4,892,538 A | 1/1990 | Aebischer et al. | |
| 5,011,472 A | 4/1991 | Aebischer et al. | |
| 5,837,234 A | 11/1998 | Gentile et al. | |
| 5,869,270 A | 2/1999 | Rhode et al. | |
| 6,139,835 A | 10/2000 | Kucherlapati et al. | |
| 6,514,752 B1 * | 2/2003 | Kucherlapati | A01K 67/0276 435/325 |
| 6,750,321 B1 * | 6/2004 | Chen | A61P 5/00 530/328 |
| 6,986,887 B2 | 1/2006 | Lawman et al. | |
| 7,399,838 B2 | 7/2008 | Reiter | |
| 8,142,772 B2 | 3/2012 | Noessner et al. | |
| 8,945,868 B2 | 2/2015 | Collingwood et al. | |
| 2002/0156258 A1 | 10/2002 | Masternak et al. | |
| 2004/0225112 A1 | 11/2004 | Crew et al. | |
| 2005/0196404 A1 | 9/2005 | Crew | |
| 2007/0020703 A1 | 1/2007 | Menier | |
| 2007/0274960 A1 | 11/2007 | Harman et al. | |
| 2008/0032941 A9 | 2/2008 | Rabbani | |
| 2008/0219956 A1 | 9/2008 | Russell et al. | |
| 2008/0299091 A1 | 12/2008 | Revazova et al. | |

FOREIGN PATENT DOCUMENTS

| | | |
|---|---|---|
| JP | 2009137857 | 6/2009 |
| WO | WO 1991/10425 | 7/1991 |
| WO | WO 1991/10470 | 7/1991 |
| WO | 1992/09688 A1 | 6/1992 |
| WO | 1993/05817 A1 | 4/1993 |
| WO | 1995/017911 A1 | 7/1995 |
| WO | 2001/72768 A1 | 10/2001 |
| WO | WO 2007/091078 | 8/2007 |
| WO | 2009/072555 | 5/2009 |
| WO | 2010/052229 A1 | 5/2010 |
| WO | 2012/012667 A2 | 1/2012 |
| WO | WO 2012/145384 | 10/2012 |
| WO | 2014/022423 A2 | 2/2014 |

OTHER PUBLICATIONS

Library of Congress (2022, pp. 1/6-6/6, world wide web at loc.gov/everyday-mysteries/biology-and-human-anatomy/item/what-are-stem-cells/) (Year: 2022).*
Aftab et al (BMC Evolut. Biol. 2008, 8:226: 1-11).
Borrego et al. (J. Exp. Med. 1998, 187(5): 813-818).
Bradley et al (Nature, 2002, 2: 859-871).
Brehm & Shultz, "Human allograft rejection in humanized mice: a historical perspective" Cellular & Molecular Immunology 9:225-231 (2012).
Chang et al. "Definitive-like erythroid cells derived from human embryonic stem cells co-express high levels of embryonic and fetal globins with little or no adult globin" Blood, vol. 108, No. 5, pp. 1515-1523 (2006).
Chen et al., "DLD-1 and HCT-15 cell lines derived separately form colorectal carcinomas have totally different chromosome changes but the same genetic origin" Cancer Genet Cytogenet. 81:103-108 (1995).
Declaration of Professor David Russell with biographical sketch, 10 pages (signed Dec. 2, 2019).

(Continued)

*Primary Examiner* — G. R. Ewoldt
*Assistant Examiner* — Marianne DiBrino
(74) *Attorney, Agent, or Firm* — MCDONNELL BOEHNEN HULBERT & BERGHOFF LLP

(57) ABSTRACT

The invention provides isolated primate cells preferably human cells that comprise a genetically engineered disruption in a beta-2 microglobulin (B2M) gene, which results in deficiency in MHC class I expression and function. Also provided are the method of using the cells for transplantation and treating a disease condition.

16 Claims, 5 Drawing Sheets

Specification includes a Sequence Listing.

(56) References Cited

OTHER PUBLICATIONS

Declaration of Professor Robert Lanza with CV, 36 pages (signed Nov. 11, 2019).
De Preval & Mach, "The absence of beta 2-microglobulin in Daudi cells: active gene but inactive messenger RNA." Immunogenetics 17(2):133-40 (1983).—Abstract only.
Deyle et al. "Normal Collagen and Bone Production by Gene-Targeted Human Osteogenesis Imperfecta iPSCs" The American Sociely of Gene and Cell Therapy, vol. 20, No. 1, pp. 204-213, (2012).
DiLorenzo et al. "Translational Mini-Review Series on Type 1 Diabetes: Systematic analysis of T cell epitopes in autoimmune diabetes," Clinical and Experimental Immunology vol. 148, pp. 1-16, (2007).
Dulberger et al., "Human leukocyte antigen F presents peptides and regulates immunity through interactions with NK cell receptors." Immunity 46:1018-1029 (Jun. 2017).
Gornalusse et al., "HLA-E expressing pluripotent stem cells escape allogeneic responses and lysis by NK cells" Nat Biotechnol. 35(8):765-772 (Aug. 2017).
Hoglund et al., "Recognition of beta-2 microglobulin-negative T-cell blasts by natural killer cells from normal but not from B2m negative mice: Nonresponsiveness controlled by B2m negative bone marrow in chimeric mice" PNAS 88:10332-336 (Nov. 1991).
Hull et al., "The origin and characteristics of a pig kidney cell strain, LLC-PK1" In Vitro 12:670-677 (1976).
Karre, "Natural killer cell recognition of missing self" Nature Immunology 9(5):477-480 (2008).
Karpova et al., "Combined spectral karyotyping, comparative genomice hybridization, and in vitro apoptypingof a panel of Burkitt's lymphoma derived B cell lines reveals an unexpected complexity of chromosomal aberrations and a recurrence of specific abnormalities in chemoresistant cell lines" Int. J. Oncology, 28:605-617 (2006).
Khan "AAV-mediated gene targeting methods for human cells" Nat Protoc. vol. 6, No. 4, pp. 482-501, (2011).
Kroon et al. "Pancreatic endoderm derived from human embryonic stem cells generates glucose-responsive insulin secreting cells in vivo" Nature Biotechnology, vol. 26, No. 4, pp. 443-452, (2008).
Laflamme et al. "Cardiomyocytes derived from human embryonic stem cells in pro-survival enhance function of infarcted rat hearts" Nature Biotechnology, vol. 25, No. 9, pp. 1015-1024, (2007).
Lee et al., "2B4 acts as a non-Major Histocompatibility Complex binding inhibitory receptor on mouse Natural Killer cells" J. Exp. Med. 199(9):1245-54 (May 2004).
Madsen et al. "Mice lacking all conventional MHC class 1 genes" PNAS, 96:10338-343 (1999).
Masternak et al., "A gene encoding a novel RFX-associated transactivator is mutated in the majority of MHC class II deficiency patients." Nature Genetics 20(3):273-7 (Nov. 1998).
Murphy et al., "Acute rejection of murine bone marrow allografts by natural killer cells and T cells" J. Exp. Med. 166:1499-1509 (Nov. 1987).
Peijnenburg et al "Defective MHC class II expression in an MHC class II deficiency patient is caused by a novel deletion of a splice donor site in the MHC class II transactivator gene" Immunogenetics, 51(1):42-49 (2000).
PIR_80 Acc. No. I61856, 3 pages (1996).
PIR_80 Acc. No. A28834, 4 pages (1989).
Santos et al., "Non-classical human leucocyte antigens in ankylosing spondylitis: possible association with HLA-E and HLA-F" Rheumatic & Musculoskeletal Diseases Open 4(1):e000677 (2018).
Slukvin et al. "Directed Differentiation of Human Embryonic Stem Cells into Functional Dendritic Cells Through the Meyloid Pathway" The Journal of Immunology, vol. 176, pp. 2924-2932, (2006).
Steimle et al. "A novel DNA-binding regulatory factor is mutated in primary MHC class II deficiency (bare lymphocyte syndrome)" Genes & Development 9(9):1021-32 (1995).

Suarez-Alvarez et al., "Epigenetic Mechanisms regulate MHC and Antigen Processing Molecules in Human Embryonic and Induced Pluripotent Stem Cells" Plos ONE 5(4) e10192, Apr. 2010.
Tatake and Zeff (PSEBM, 1993, 203:405-417) (Year: 1993).
Van Eggermond et al "Trancriptional silencing of RFXAP in MHC class II-deficiency" Molecular Immunology, 45(10):2920-28 (2008).
Pazmany, et al., "Protection from Natural Killer Cell-Mediated Lysis by HLA-G Expression in Target cells," Science (1996) vol. 274, pp. 792-795.
International Search report for PCT/US2012/034051, dated Jul. 20, 2012.
"7th Australasian gene Therapy society meeting," The Journal of Gene Medicine, 13(7-8): 410-446, Jul. 2011.
Gattoni-Celli et al. "beta-2 microglobulin gene is mutated in a human colon cancer cell line HCT deficient in the expression of HLA class I antigens on the cell surface," Cancer Research. 52(5): 1201-1204, 1992.
Orr, et al. "Natural Killer Cell Education and Tolerance," Cell, 142: 847-856, Sep. 2010.
Parham "MHC class I molecules and KIRS in human history, health and survival," Nature Reviews: immunology, 5:201-214, Mar. 2005.
Ordaz, et al. "DC-expressed MHC class I single-chain trimer-based vaccines prime cytotoxic T lymphocytes against exogenous but not endogenous antigens," Cellular Immunology, 262:141-149, Feb. 2010.
Bix et al. "Rejection of class I MHC-deficient haemopoietic cells by irradiated MHC-matched mice," Nature, vol. 349, Jan. 1991, pp. 329-331.
Crew et al. "An HLA-E single chain trimer inhibits human NK cell reactivity towards porcine cells," Molecular Immunology, 42(2005): 1205-1214.
Jaimes et al. "Regulation of HLA class II expression prevents allogeneic T-cell responses," Tissue Antigens (2010), 77:36-44.
Jiang et al. "Interaction of natural killer cells with MHC class II: reversal of HLA-DR1-mediated protection of K562 transfectant from natural killer cell-mediated cytolysis by brefeldin-A," Immunology (1996) 87: 481-486.
Storkus, et al., "Reversal of natural killing susceptibility in target cells expressing transfected class I HLA genes," Proc. Natl. Acad Sci USA (Apr. 1989) 86: 2361-2364.
Li et al (Nature 7/11, 475: 217-223) (Year: 2011).
Wang et al (Stem Cells Translational Medicine, 2015, 4: 1234-1245) (Year: 2015).
Zijlstra et al 1989 (Nature, 1989, 342: 435-438) (Year: 1989).
Schwartz and Wesselschmidt (Human Pluripotent Stem Cells Methods and Protocols, Human Press, 2011, Chapter 2 pp. 23-24) (Year: 2011).
Lu et al (Stem Cell Rev and Rep, 2013, 9:806-813).
Biology online (2016, world wide web at biology-online.org).
Matsunaga et al (J. Immunol. 2008, 181: 6635-6643).
Khan et al (Mol. Ther. 6/10, 18(6): 1192-1199).
Marsh (2009, HLA Nomenclature, Anthony Nolan Research Institute London).
Brehm MA et al. 2010. Parameters for establishing humanized mouse models to study human immunity: analysis of human hematopoietic stem cell engraftment in three immunodeficient strains of mice bearing the IL2(gamma)mutation. Clin Immunol 135:84-98.
Campos-Martin et al. 2004. Expression of human CD1d molecules protects target cells from NK cell-mediated cytolysis. J Immunol 172:7297-7305.
Carbone et al. 2000. Inhibition of human NK cell-mediated killing by CD1 molecules. J Immunol 164:6130-6137.
Coffman et al. 1993 The Journal of Immunology vol. 151, No. 1, 425-435, "Improved Renal Function in Mouse Kidney Allografts Lacking MHC Class I Antigens".
Hillyard et al. 2007. Statins inhibit NK cell cytotoxicity by membrane raft depletion rather than inhibition of isoprenylation. Atherosclerosis 191:319-325.
Huang et al. 2005. NK cells play a critical role in the regulation of class I-deficient hemopoietic stem cell engraftment: evidence for NK tolerance correlates with receptor editing. J Immunol 175:3753-3761.

(56) References Cited

OTHER PUBLICATIONS

King et al. 2008. A new Hu-PBL model for the study of human islet alloreactivity based on NOD-scid mice bearing a targeted mutation in the IL-2 receptor gamma chain gene. Clin Immunol 126:303-314.
Koller et al. 1990 Science vol. 248, pp. 1227-1230, "Normal Development of Mice Deficient in B2M, MHC Class I Proteins and CD8+ T Cells".
Kumar et al. 2005. A new self: MHC-class-I-independent natural-killer-cell self-tolerance. Nat Rev Immunol 5:363-374.
Li and Faustman, 1993 Transplantation vol. 55, 940-946, No. 4, "Use of Donor B2-Microglobulin-Deficient Transgenic Mouse Liver Cells for Isografts, Allografts, and Xenografts".
Pegram et al. 2011. Activating and inhibitory receptors of natural killer cells. Immunol Cell Biol 89:216-224.
Prange et al. 2001 Transplantation vol. 71, No. 7, pp. 982-985, "Transplanted MHC Class I-Deficient Nonobese Diabetic Mouse Islets Are Protected From Autoimmune Injury in Diabetic Nonobese Recipients".
Qian et al. 1996 Immunology vol. 88, 124-129, "Impact of Donor MHC Class I or Class II Antigen Deficiency on First- and Second-Set Rejection of Mouse Heart or Liver Allografts".
Raulet et al. 2006. Self-tolerance of natural killer cells. Nat Rev Immunol 6:520-531.
Yeager et al. 1995. Morphine inhibits spontaneous and cytokine-enhanced natural killer cell cytotoxicity in volunteers. Anesthesiology 83:500-508.
Zijlstra et al. 1990 Nature vol. 344, pp. 742-746, "B2-Microglobulin Deficient Mice Lack CD4-8+ Cytolytic T cells".
Lilienfeld et al. "Transgenic expression of HLA-E single chain trimer protects porcine endothelial cells against human natural killer cell-mediated cytotoxicity," Xenotransplantation (2007) 14:126-134.
Toshilani et al. "Expression of a single chain HLA class I molecule in a human cell line: Presentation of exogenous peptide and processed antigen to cytotoxic T lymphocytes," Proc. Natl. Acad. Sci. USA (1996) 93: 236-240.
Bicknell et al. "82-Microglobulin gene mutations: A study of established coloreclal cell lines and fresh tumors," Proc. Natl. Acad. Sci. USA (1994) 91: 4751-4755.
Obermann et al. "Peplide-82-microglobulin-major histocompatability complex expressing cells are potent antigen-presenting cells that can generate specific T cells," Immunology (2007) 122(1): 90-97.
Daudi cells from the American Type Culture Collection. 2016.
Greten et al. "Peplide-82-microglobulin-MHC fusion molecules bind antigen-specific T cells and can be used for multivalent MHC-Ig complexes," Journal of Immunological Methods (2002) 271: 125-135.
Hansen et al. "Translational and basic applications of peplide-MHCI single chain Irimers," Trend Immunol. (2010) 31(10):363-369.
Kolsiou et al. "Properties and Application of single-chain major histocompatibility complex class I molecules," Antioxidanls & Redox Signalling (2011) 15(3): 645-655.
Jordanova et al. "Beta-2-MICROGLOBULIN Aberrations in Diffuse Large B-Cell Lymphoma of the Testis and the Central Nervous System" Int. J. Cancer 103:393-98 (2003).
Paschen et al., "Complete Loss of HLA Class I Antigen Expression on Melanoma Cells: a Result of Successive Mutational Events" Int. J. Cancer 103:759-67 (2003).
Quintarelli et al., Blood 2007 vol. 110, pp. 2793-2802.
Restifo et al., Molecular Mechanisms Used by Tumors to Escape Immune Recognition: "Immunogenetherapy and the Cell Biology of Major Histocompatibility Complex Class I" J Immunother Emphasis Tumor Immunol. 14(3):182-90 (Oct. 1993).
Riolobos et al., "HLA Engineering of human pluripotent stem cells" Molecular Therapy 21(6):1232-41 (Jun. 2013).
GenBank Accession No. NM_134440.1, Mar. 24, 2012 (Year: 2012).
GenBank Accession No. NM_003721.2, Mar. 24, 2012 (Year: 2012).
GenBank Accession No. NM_000449.3, Mar. 24, 2012 (Year: 2012).
GenBank Accession No. NM_001025603.1, Mar. 24, 2012 (Year: 2012).
GenBank Accession No. NM_000538.3, Mar. 25, 2012 (Year: 2012).
GenBank Accession No. NM_000246.3, Mar. 25, 2012 (Year: 2012).
Munz et al., J. Repr. Immunol. 1999 43:139-155 (Year: 1999).

\* cited by examiner

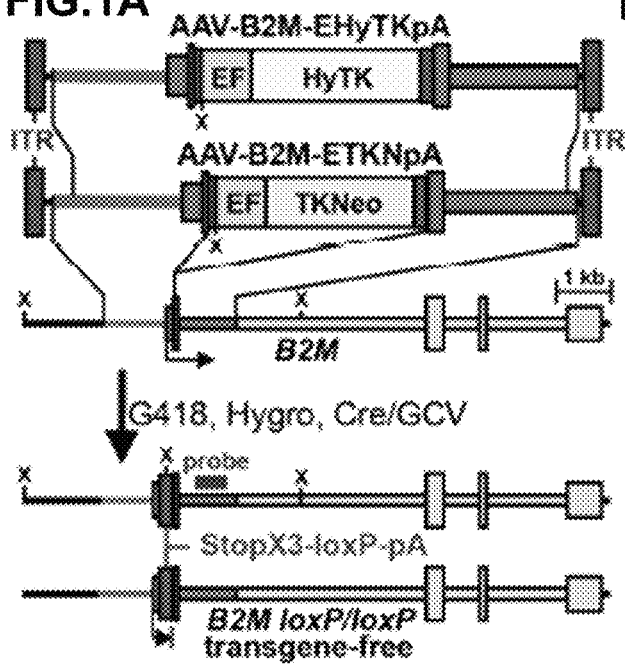
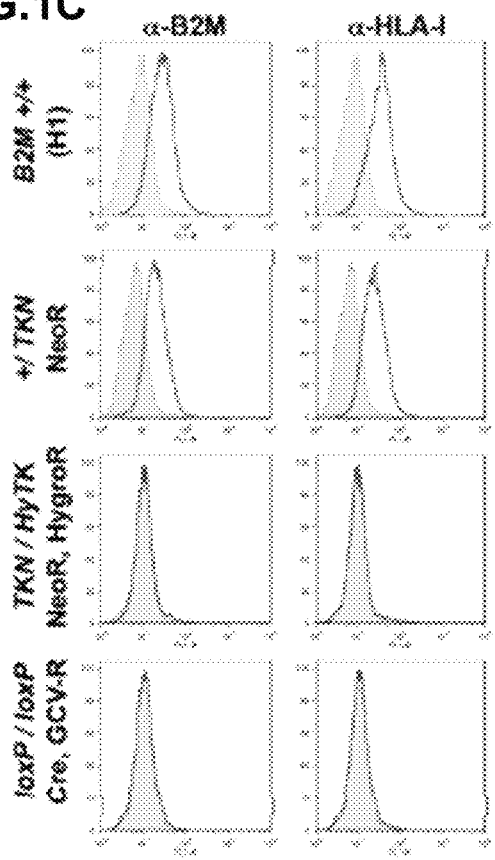
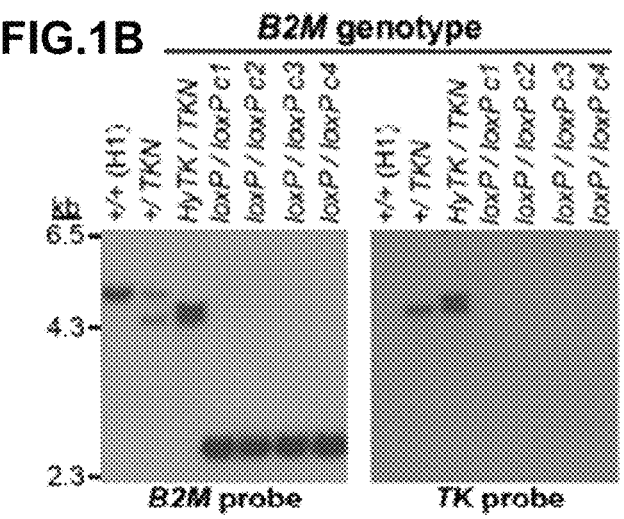

FIG. 3A
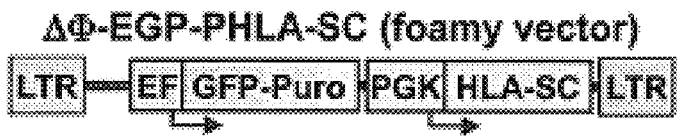
FIG. 3B HLA-SC Proteins
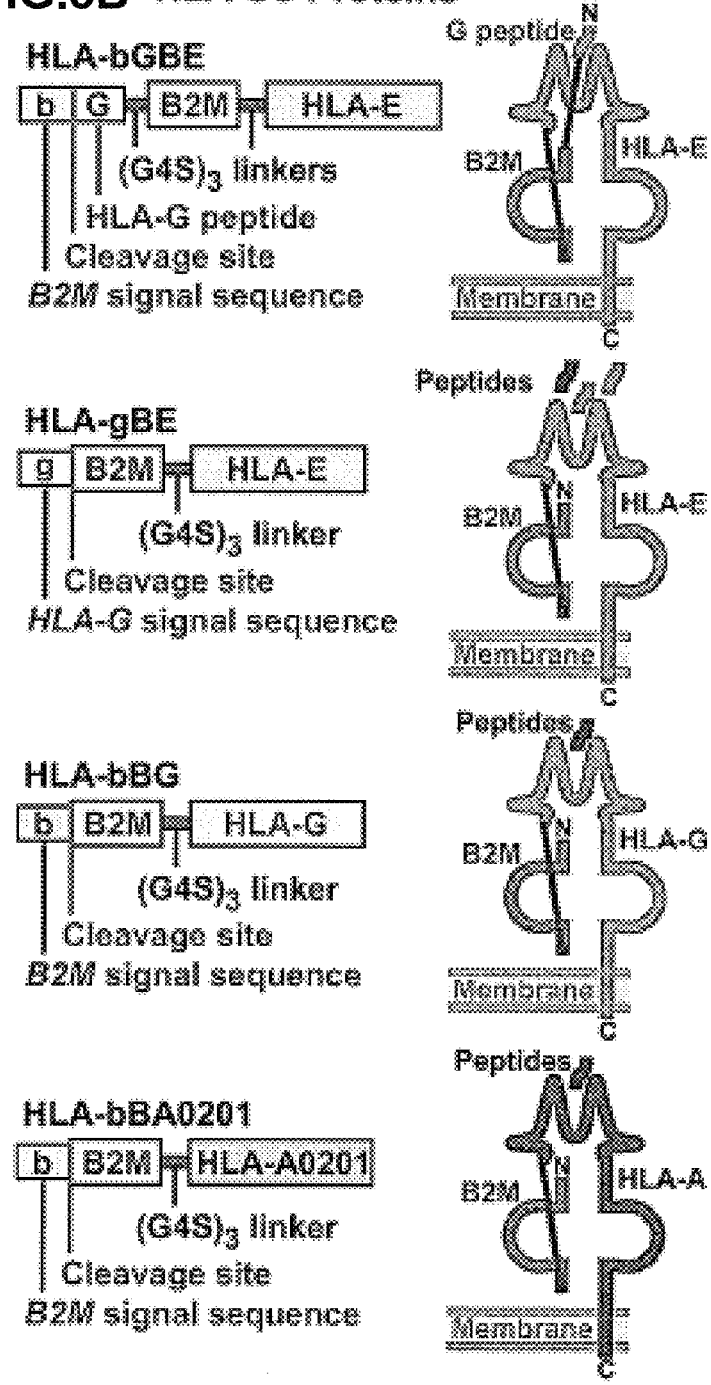
FIG. 3C
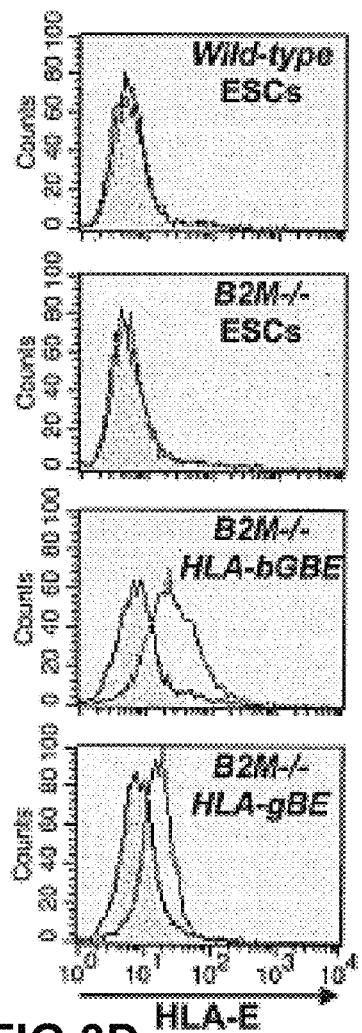
FIG. 3D
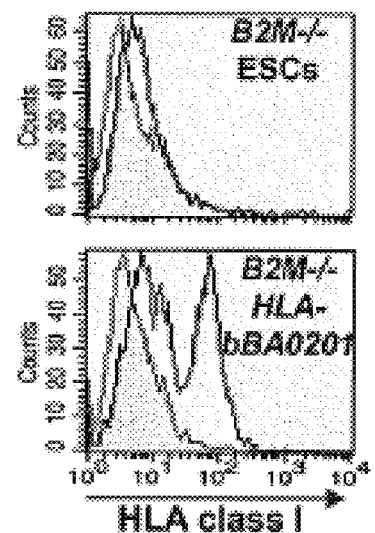

SEQUENCE LISTING

```
<160> NUMBER OF SEQ ID NOS: 24

<210> SEQ ID NO 1
<211> LENGTH: 987
<212> TYPE: DNA
<213> ORGANISM: Homo sapiens
<220> FEATURE:
<221> NAME/KEY: CDS
```

<222> LOCATION: (61)..(420)

<400> SEQUENCE: 1

| aatataagtg | gaggcgtcgc | gctggcgggc | attcctgaag | ctgacagcat | tcgggccgag | 60 |

| atg | tct | cgc | tcc | gtg | gcc | tta | gct | gtg | ctc | gcg | cta | ctc | tct | ctt | tct | 108 |
| Met | Ser | Arg | Ser | Val | Ala | Leu | Ala | Val | Leu | Ala | Leu | Leu | Ser | Leu | Ser | |
| 1 | | | | 5 | | | | | 10 | | | | | 15 | | |

| ggc | ctg | gag | gct | atc | cag | cgt | act | cca | aag | att | cag | gtt | tac | tca | cgt | 156 |
| Gly | Leu | Glu | Ala | Ile | Gln | Arg | Thr | Pro | Lys | Ile | Gln | Val | Tyr | Ser | Arg | |
| | | | 20 | | | | | 25 | | | | | 30 | | | |

| cat | cca | gca | gag | aat | gga | aag | tca | aat | ttc | ctg | aat | tgc | tat | gtg | tct | 204 |
| His | Pro | Ala | Glu | Asn | Gly | Lys | Ser | Asn | Phe | Leu | Asn | Cys | Tyr | Val | Ser | |
| | | 35 | | | | | 40 | | | | | 45 | | | | |

| ggg | ttt | cat | cca | tcc | gac | att | gaa | gtt | gac | tta | ctg | aag | aat | gga | gag | 252 |
| Gly | Phe | His | Pro | Ser | Asp | Ile | Glu | Val | Asp | Leu | Leu | Lys | Asn | Gly | Glu | |
| 50 | | | | | 55 | | | | | 60 | | | | | | |

| aga | att | gaa | aaa | gtg | gag | cat | tca | gac | ttg | tct | ttc | agc | aag | gac | tgg | 300 |
| Arg | Ile | Glu | Lys | Val | Glu | His | Ser | Asp | Leu | Ser | Phe | Ser | Lys | Asp | Trp | |
| 65 | | | | | 70 | | | | | 75 | | | | | 80 | |

| tct | ttc | tat | ctc | ttg | tac | tac | act | gaa | ttc | acc | ccc | act | gaa | aaa | gat | 348 |
| Ser | Phe | Tyr | Leu | Leu | Tyr | Tyr | Thr | Glu | Phe | Thr | Pro | Thr | Glu | Lys | Asp | |
| | | | | 85 | | | | | 90 | | | | | 95 | | |

| gag | tat | gcc | tgc | cgt | gtg | aac | cat | gtg | act | ttg | tca | cag | ccc | aag | ata | 396 |
| Glu | Tyr | Ala | Cys | Arg | Val | Asn | His | Val | Thr | Leu | Ser | Gln | Pro | Lys | Ile | |
| | | | 100 | | | | | 105 | | | | | 110 | | | |

| gtt | aag | tgg | gat | cga | gac | atg | taa | gcagcatcat | ggaggtttga | agatgccgca | 450 |
| Val | Lys | Trp | Asp | Arg | Asp | Met | | | | | |
| | | | 115 | | | | | | | | |

| tttggattgg | atgaattcca | aattctgctt | gcttgctttt | taatattgat | atgcttatac | 510 |
| acttacactt | tatgcacaaa | atgtagggtt | ataataatgt | taacatggac | atgatcttct | 570 |
| ttataattct | actttgagtg | ctgtctccat | gtttgatgta | tctgagcagg | ttgctccaca | 630 |
| ggtagctcta | ggagggctgg | caacttagag | gtggggagca | gagaattctc | ttatccaaca | 690 |
| tcaacatctt | ggtcagattt | gaactcttca | atctcttgca | ctcaaagctt | gttaagatag | 750 |
| ttaagcgtgc | ataagttaac | ttccaattta | catactctgc | ttagaatttg | ggggaaaatt | 810 |
| tagaaatata | attgacagga | ttattggaaa | tttgttataa | tgaatgaaac | attttgtcat | 870 |
| ataagattca | tatttacttc | ttatacattt | gataaagtaa | ggcatggttg | tggttaatct | 930 |
| ggtttatttt | tgttccacaa | gttaaataaa | tcataaaact | tgatgtgtta | tctctta | 987 |

<210> SEQ ID NO 2
<211> LENGTH: 119
<212> TYPE: PRT
<213> ORGANISM: Homo sapiens

<400> SEQUENCE: 2

| Met | Ser | Arg | Ser | Val | Ala | Leu | Ala | Val | Leu | Ala | Leu | Leu | Ser | Leu | Ser |
| 1 | | | | 5 | | | | | 10 | | | | | 15 | |

| Gly | Leu | Glu | Ala | Ile | Gln | Arg | Thr | Pro | Lys | Ile | Gln | Val | Tyr | Ser | Arg |
| | | | 20 | | | | | 25 | | | | | 30 | | |

| His | Pro | Ala | Glu | Asn | Gly | Lys | Ser | Asn | Phe | Leu | Asn | Cys | Tyr | Val | Ser |
| | | 35 | | | | | 40 | | | | | 45 | | | |

| Gly | Phe | His | Pro | Ser | Asp | Ile | Glu | Val | Asp | Leu | Leu | Lys | Asn | Gly | Glu |
| 50 | | | | | 55 | | | | | 60 | | | | | |

| Arg | Ile | Glu | Lys | Val | Glu | His | Ser | Asp | Leu | Ser | Phe | Ser | Lys | Asp | Trp |
| 65 | | | | | 70 | | | | | 75 | | | | | 80 |

```
Ser Phe Tyr Leu Leu Tyr Tyr Thr Glu Phe Thr Pro Thr Glu Lys Asp
            85                  90                  95

Glu Tyr Ala Cys Arg Val Asn His Val Thr Leu Ser Gln Pro Lys Ile
        100                 105                 110

Val Lys Trp Asp Arg Asp Met
        115

<210> SEQ ID NO 3
<211> LENGTH: 1611
<212> TYPE: DNA
<213> ORGANISM: Homo sapiens
<220> FEATURE:
<221> NAME/KEY: CDS
<222> LOCATION: (85)..(1182)

<400> SEQUENCE: 3
```

| | |
|---|---|
| gagaagccaa tcagtgtcgt cgcggtcgct gttctaaagt ccgcacgcac ccaccgggac | 60 |
| tcagattctc cccagacgcc gagg atg gcc gtc atg gcg ccc cga acc ctc<br>                                        Met Ala Val Met Ala Pro Arg Thr Leu<br>                                        1                  5 | 111 |
| ctc ctg cta ctc tcg ggg gcc ctg gcc ctg acc cag acc tgg gcg ggc<br>Leu Leu Leu Leu Ser Gly Ala Leu Ala Leu Thr Gln Thr Trp Ala Gly<br>10                  15                    20                  25 | 159 |
| tcc cac tcc atg agg tat ttc ttc aca tcc gtg tcc cgg ccc ggc cgc<br>Ser His Ser Met Arg Tyr Phe Phe Thr Ser Val Ser Arg Pro Gly Arg<br>                  30                    35                  40 | 207 |
| ggg gag ccc cgc ttc atc gcc gtg ggc tac gtg gac gac acg cag ttc<br>Gly Glu Pro Arg Phe Ile Ala Val Gly Tyr Val Asp Asp Thr Gln Phe<br>              45                    50                   55 | 255 |
| gtg cgg ttc gac agc gac gcc gcg agc cag aag atg gag ccg cgg gcg<br>Val Arg Phe Asp Ser Asp Ala Ala Ser Gln Lys Met Glu Pro Arg Ala<br>      60                    65                    70 | 303 |
| ccg tgg ata gag cag gag ggg ccg gag tat tgg gac cag gag aca cgg<br>Pro Trp Ile Glu Gln Glu Gly Pro Glu Tyr Trp Asp Gln Glu Thr Arg<br>75                  80                    85 | 351 |
| aat atg aag gcc cac tca cag act gac cga gcg aac ctg ggg acc ctg<br>Asn Met Lys Ala His Ser Gln Thr Asp Arg Ala Asn Leu Gly Thr Leu<br>90                  95                    100               105 | 399 |
| cgc ggc tac tac aac cag agc gag gac ggt tct cac acc atc cag ata<br>Arg Gly Tyr Tyr Asn Gln Ser Glu Asp Gly Ser His Thr Ile Gln Ile<br>                  110                  115                120 | 447 |
| atg tat ggc tgc gac gtg ggg ccg gac ggg cgc ttc ctc cgc ggg tac<br>Met Tyr Gly Cys Asp Val Gly Pro Asp Gly Arg Phe Leu Arg Gly Tyr<br>                    125                  130                135 | 495 |
| cgg cag gac gcc tac gac ggc aag gat tac atc gcc ctg aac gag gac<br>Arg Gln Asp Ala Tyr Asp Gly Lys Asp Tyr Ile Ala Leu Asn Glu Asp<br>            140                    145                  150 | 543 |
| ctg cgc tct tgg acc gcg gcg gac atg gca gct cag atc acc aag cgc<br>Leu Arg Ser Trp Thr Ala Ala Asp Met Ala Ala Gln Ile Thr Lys Arg<br>     155                    160                    165 | 591 |
| aag tgg gag gcg gtc cat gcg gcg gag cag cgg aga gtc tac ctg gag<br>Lys Trp Glu Ala Val His Ala Ala Glu Gln Arg Arg Val Tyr Leu Glu<br>170                 175                   180               185 | 639 |
| ggc cgg tgc gtg gac ggg ctc cgc aga tac ctg gag aac ggg aag gag<br>Gly Arg Cys Val Asp Gly Leu Arg Arg Tyr Leu Glu Asn Gly Lys Glu<br>                  190                  195                200 | 687 |
| acg ctg cag cgc acg gac ccc ccc aag aca cat atg acc cac cac ccc<br>Thr Leu Gln Arg Thr Asp Pro Pro Lys Thr His Met Thr His His Pro<br>            205                    210                  215 | 735 |
| atc tct gac cat gag gcc acc ctg agg tgc tgg gcc ctg ggc ttc tac | 783 |

```
                Ile Ser Asp His Glu Ala Thr Leu Arg Cys Trp Ala Leu Gly Phe Tyr
                        220                 225                 230 cct gcg gag atc aca ctg acc tgg cag cgg gat ggg gag gac cag acc       831
Pro Ala Glu Ile Thr Leu Thr Trp Gln Arg Asp Gly Glu Asp Gln Thr
        235                 240                 245 cag gac acg gag ctc gtg gag acc agg cct gca ggg gat gga acc ttc       879
Gln Asp Thr Glu Leu Val Glu Thr Arg Pro Ala Gly Asp Gly Thr Phe
250                 255                 260                 265 cag aag tgg gcg gct gtg gtg gtg cct tct gga gag gag cag aga tac       927
Gln Lys Trp Ala Ala Val Val Val Pro Ser Gly Glu Glu Gln Arg Tyr
                270                 275                 280 acc tgc cat gtg cag cat gag ggt ctg ccc aag ccc ctc acc ctg aga       975
Thr Cys His Val Gln His Glu Gly Leu Pro Lys Pro Leu Thr Leu Arg
            285                 290                 295 tgg gag ctg tct tcc cag ccc acc atc ccc atc gtg ggc atc att gct      1023
Trp Glu Leu Ser Ser Gln Pro Thr Ile Pro Ile Val Gly Ile Ile Ala
        300                 305                 310 ggc ctg gtt ctc ctt gga gct gtg atc act gga gct gtg gtc gct gcc      1071
Gly Leu Val Leu Leu Gly Ala Val Ile Thr Gly Ala Val Val Ala Ala
315                 320                 325 gtg atg tgg agg agg aag agc tca gat aga aaa gga ggg agt tac act      1119
Val Met Trp Arg Arg Lys Ser Ser Asp Arg Lys Gly Gly Ser Tyr Thr
330                 335                 340                 345 cag gct gca agc agt gac agt gcc cag ggc tct gat gtg tct ctc aca      1167
Gln Ala Ala Ser Ser Asp Ser Ala Gln Gly Ser Asp Val Ser Leu Thr
                350                 355                 360 gct tgt aaa gtg tga gacagctgcc ttgtgtggga ctgagaggca agagttgttc      1222
Ala Cys Lys Val
            365 ctgcccttcc ctttgtgact tgaagaaccc tgactttgtt tctgcaaagg cacctgcatg    1282 tgtctgtgtt cgtgtaggca taatgtgagg aggtggggag agcaccccac ccccatgtcc    1342 accatgaccc tcttcccacg ctgacctgtg ctccctctcc aatcatcttt cctgttccag    1402 agaggtgggg ctgaggtgtc tccatctctg tctcaacttc atggtgcact gagctgtaac    1462 ttcttccttc cctattaaaa ttagaacctg agtataaatt tactttctca aattcttgcc    1522 atgagaggtt gatgagttaa ttaaaggaga agattcctaa aatttgagag acaaaattaa    1582 tggaacgcat gagaaccttc cagagtcca                                      1611

<210> SEQ ID NO 4
<211> LENGTH: 365
<212> TYPE: PRT
<213> ORGANISM: Homo sapiens

<400> SEQUENCE: 4

Met Ala Val Met Ala Pro Arg Thr Leu Leu Leu Leu Leu Ser Gly Ala
1               5                   10                  15

Leu Ala Leu Thr Gln Thr Trp Ala Gly Ser His Ser Met Arg Tyr Phe
                20                  25                  30

Phe Thr Ser Val Ser Arg Pro Gly Arg Gly Glu Pro Arg Phe Ile Ala
            35                  40                  45

Val Gly Tyr Val Asp Asp Thr Gln Phe Val Arg Phe Asp Ser Asp Ala
        50                  55                  60

Ala Ser Gln Lys Met Glu Pro Arg Ala Pro Trp Ile Glu Gln Glu Gly
65                  70                  75                  80

Pro Glu Tyr Trp Asp Gln Glu Thr Arg Asn Met Lys Ala His Ser Gln
                85                  90                  95
```

```
Thr Asp Arg Ala Asn Leu Gly Thr Leu Arg Gly Tyr Tyr Asn Gln Ser
            100                 105                 110

Glu Asp Gly Ser His Thr Ile Gln Ile Met Tyr Gly Cys Asp Val Gly
        115                 120                 125

Pro Asp Gly Arg Phe Leu Arg Gly Tyr Arg Gln Asp Ala Tyr Asp Gly
    130                 135                 140

Lys Asp Tyr Ile Ala Leu Asn Glu Asp Leu Arg Ser Trp Thr Ala Ala
145                 150                 155                 160

Asp Met Ala Ala Gln Ile Thr Lys Arg Lys Trp Glu Ala Val His Ala
                165                 170                 175

Ala Glu Gln Arg Arg Val Tyr Leu Glu Gly Arg Cys Val Asp Gly Leu
            180                 185                 190

Arg Arg Tyr Leu Glu Asn Gly Lys Glu Thr Leu Gln Arg Thr Asp Pro
        195                 200                 205

Pro Lys Thr His Met Thr His His Pro Ile Ser Asp His Glu Ala Thr
    210                 215                 220

Leu Arg Cys Trp Ala Leu Gly Phe Tyr Pro Ala Glu Ile Thr Leu Thr
225                 230                 235                 240

Trp Gln Arg Asp Gly Glu Asp Gln Thr Gln Asp Thr Glu Leu Val Glu
                245                 250                 255

Thr Arg Pro Ala Gly Asp Gly Thr Phe Gln Lys Trp Ala Ala Val Val
            260                 265                 270

Val Pro Ser Gly Glu Glu Gln Arg Tyr Thr Cys His Val Gln His Glu
        275                 280                 285

Gly Leu Pro Lys Pro Leu Thr Leu Arg Trp Glu Leu Ser Ser Gln Pro
    290                 295                 300

Thr Ile Pro Ile Val Gly Ile Ile Ala Gly Leu Val Leu Leu Gly Ala
305                 310                 315                 320

Val Ile Thr Gly Ala Val Val Ala Ala Val Met Trp Arg Arg Lys Ser
                325                 330                 335

Ser Asp Arg Lys Gly Gly Ser Tyr Thr Gln Ala Ala Ser Ser Asp Ser
            340                 345                 350

Ala Gln Gly Ser Asp Val Ser Leu Thr Ala Cys Lys Val
        355                 360                 365

<210> SEQ ID NO 5
<211> LENGTH: 1578
<212> TYPE: DNA
<213> ORGANISM: Homo sapiens
<220> FEATURE:
<221> NAME/KEY: CDS
<222> LOCATION: (55)..(1143)

<400> SEQUENCE: 5
agttctaaag tccccacgca cccacccgga ctcagagtct cctcagacgc cgag atg      57
                                                              Met
                                                               1 ctg gtc atg gcg ccc cga acc gtc ctc ctg ctc tcg gcg gcc ctg          105
Leu Val Met Ala Pro Arg Thr Val Leu Leu Leu Ser Ala Ala Leu
         5                  10                  15 gcc ctg acc gag acc tgg gcc ggc tcc cac tcc atg agg tat ttc tac      153
Ala Leu Thr Glu Thr Trp Ala Gly Ser His Ser Met Arg Tyr Phe Tyr
             20                  25                  30 acc tcc gtg tcc cgg ccc ggc cgc ggg gag ccc cgc ttc atc tca gtg      201
Thr Ser Val Ser Arg Pro Gly Arg Gly Glu Pro Arg Phe Ile Ser Val
         35                  40                  45 ggc tac gtg gac gac acc cag ttc gtg agg ttc gac agc gac gcc gcg      249
```

```
Gly Tyr Val Asp Asp Thr Gln Phe Val Arg Phe Asp Ser Asp Ala Ala
 50              55                  60                  65 agt ccg aga gag gag ccg cgg gcg ccg tgg ata gag cag gag ggg ccg    297
Ser Pro Arg Glu Glu Pro Arg Ala Pro Trp Ile Glu Gln Glu Gly Pro
                 70                  75                  80 gag tat tgg gac cgg aac aca cag atc tac aag gcc cag gca cag act    345
Glu Tyr Trp Asp Arg Asn Thr Gln Ile Tyr Lys Ala Gln Ala Gln Thr
             85                  90                  95 gac cga gag agc ctg cgg aac ctg cgc ggc tac tac aac cag agc gag    393
Asp Arg Glu Ser Leu Arg Asn Leu Arg Gly Tyr Tyr Asn Gln Ser Glu
         100                 105                 110 gcc ggg tct cac acc ctc cag agc atg tac ggc tgc gac gtg ggg ccg    441
Ala Gly Ser His Thr Leu Gln Ser Met Tyr Gly Cys Asp Val Gly Pro
     115                 120                 125 gac ggg cgc ctc ctc cgc ggg cat gac cag tac gcc tac gac ggc aag    489
Asp Gly Arg Leu Leu Arg Gly His Asp Gln Tyr Ala Tyr Asp Gly Lys
130                 135                 140                 145 gat tac atc gcc ctg aac gag gac ctg cgc tcc tgg acc gcc gcg gac    537
Asp Tyr Ile Ala Leu Asn Glu Asp Leu Arg Ser Trp Thr Ala Ala Asp
                150                 155                 160 acg gcg gct cag atc acc cag cgc aag tgg gag gcg gcc cgt gag gcg    585
Thr Ala Ala Gln Ile Thr Gln Arg Lys Trp Glu Ala Ala Arg Glu Ala
            165                 170                 175 gag cag cgg aga gcc tac ctg gag ggc gag tgc gtg gag tgg ctc cgc    633
Glu Gln Arg Arg Ala Tyr Leu Glu Gly Glu Cys Val Glu Trp Leu Arg
        180                 185                 190 aga tac ctg gag aac ggg aag gac aag ctg gag cgc gct gac ccc cca    681
Arg Tyr Leu Glu Asn Gly Lys Asp Lys Leu Glu Arg Ala Asp Pro Pro
    195                 200                 205 aag aca cac gtg acc cac cac ccc atc tct gac cat gag gcc acc ctg    729
Lys Thr His Val Thr His His Pro Ile Ser Asp His Glu Ala Thr Leu
210                 215                 220                 225 agg tgc tgg gcc ctg ggt ttc tac cct gcg gag atc aca ctg acc tgg    777
Arg Cys Trp Ala Leu Gly Phe Tyr Pro Ala Glu Ile Thr Leu Thr Trp
                230                 235                 240 cag cgg gat ggc gag gac caa act cag gac act gag ctt gtg gag acc    825
Gln Arg Asp Gly Glu Asp Gln Thr Gln Asp Thr Glu Leu Val Glu Thr
            245                 250                 255 aga cca gca gga gat aga acc ttc cag aag tgg gca gct gtg gtg gtg    873
Arg Pro Ala Gly Asp Arg Thr Phe Gln Lys Trp Ala Ala Val Val Val
        260                 265                 270 cct tct gga gaa gag cag aga tac aca tgc cat gta cag cat gag ggg    921
Pro Ser Gly Glu Glu Gln Arg Tyr Thr Cys His Val Gln His Glu Gly
    275                 280                 285 ctg ccg aag ccc ctc acc ctg aga tgg gag ccg tct cca gtc acc    969
Leu Pro Lys Pro Leu Thr Leu Arg Trp Glu Pro Ser Ser Gln Ser Thr
290                 295                 300                 305 gtc ccc atc gtg ggc att gtt gct ggc ctg gct gtc cta gca gtt gtg   1017
Val Pro Ile Val Gly Ile Val Ala Gly Leu Ala Val Leu Ala Val Val
                310                 315                 320 gtc atc gga gct gtg gtc gct gct gtg atg tgt agg agg aag agt tca   1065
Val Ile Gly Ala Val Val Ala Ala Val Met Cys Arg Arg Lys Ser Ser
            325                 330                 335 ggt gga aaa gga ggg agc tac tct cag gct gcg tgc agc gac agt gcc   1113
Gly Gly Lys Gly Gly Ser Tyr Ser Gln Ala Ala Cys Ser Asp Ser Ala
        340                 345                 350 cag ggc tct gat gtg tct ctc aca gct tga aaagcctgag acagctgtct     1163
Gln Gly Ser Asp Val Ser Leu Thr Ala
    355                 360
```

-continued

```
tgtgagggac tgagatgcag gatttcttca cgcctcccct ttgtgacttc aagagcctct    1223
ggcatctctt tctgcaaagg cacctgaatg tgtctgcgtc cctgttagca taatgtgagg    1283
aggtggagag acagcccacc cttgtgtcca ctgtgacccc tgttcccatg ctgacctgtg    1343
tttcctcccc agtcatcttt cttgttccag agaggtgggg ctggatgtct ccatctctgt    1403
ctcaacttta cgtgcactga gctgcaactt cttacttccc tactgaaaat aagaatctga    1463
atataaattt gttttctcaa atatttgcta tgagaggttg atggattaat taaataagtc    1523
aattcctgga atttgagaga gcaaataaag acctgagaac cttccagaaa aaaaa         1578
```

<210> SEQ ID NO 6
<211> LENGTH: 362
<212> TYPE: PRT
<213> ORGANISM: Homo sapiens

<400> SEQUENCE: 6

```
Met Leu Val Met Ala Pro Arg Thr Val Leu Leu Leu Ser Ala Ala
1               5                   10                  15

Leu Ala Leu Thr Glu Thr Trp Ala Gly Ser His Ser Met Arg Tyr Phe
            20                  25                  30

Tyr Thr Ser Val Ser Arg Pro Gly Arg Gly Glu Pro Arg Phe Ile Ser
        35                  40                  45

Val Gly Tyr Val Asp Asp Thr Gln Phe Val Arg Phe Asp Ser Asp Ala
    50                  55                  60

Ala Ser Pro Arg Glu Glu Pro Arg Ala Pro Trp Ile Glu Gln Glu Gly
65                  70                  75                  80

Pro Glu Tyr Trp Asp Arg Asn Thr Gln Ile Tyr Lys Ala Gln Ala Gln
                85                  90                  95

Thr Asp Arg Glu Ser Leu Arg Asn Leu Arg Gly Tyr Tyr Asn Gln Ser
            100                 105                 110

Glu Ala Gly Ser His Thr Leu Gln Ser Met Tyr Gly Cys Asp Val Gly
        115                 120                 125

Pro Asp Gly Arg Leu Leu Arg Gly His Asp Gln Tyr Ala Tyr Asp Gly
    130                 135                 140

Lys Asp Tyr Ile Ala Leu Asn Glu Asp Leu Arg Ser Trp Thr Ala Ala
145                 150                 155                 160

Asp Thr Ala Ala Gln Ile Thr Gln Arg Lys Trp Glu Ala Ala Arg Glu
                165                 170                 175

Ala Glu Gln Arg Arg Ala Tyr Leu Glu Gly Glu Cys Val Glu Trp Leu
            180                 185                 190

Arg Arg Tyr Leu Glu Asn Gly Lys Asp Lys Leu Glu Arg Ala Asp Pro
        195                 200                 205

Pro Lys Thr His Val Thr His His Pro Ile Ser Asp His Glu Ala Thr
    210                 215                 220

Leu Arg Cys Trp Ala Leu Gly Phe Tyr Pro Ala Glu Ile Thr Leu Thr
225                 230                 235                 240

Trp Gln Arg Asp Gly Glu Asp Gln Thr Gln Asp Thr Glu Leu Val Glu
                245                 250                 255

Thr Arg Pro Ala Gly Asp Arg Thr Phe Gln Lys Trp Ala Ala Val Val
            260                 265                 270

Val Pro Ser Gly Glu Glu Gln Arg Tyr Thr Cys His Val Gln His Glu
        275                 280                 285

Gly Leu Pro Lys Pro Leu Thr Leu Arg Trp Glu Pro Ser Ser Gln Ser
    290                 295                 300
```

```
Thr Val Pro Ile Val Gly Ile Val Ala Gly Leu Ala Val Leu Ala Val
305                 310                 315                 320

Val Val Ile Gly Ala Val Val Ala Ala Val Met Cys Arg Arg Lys Ser
                325                 330                 335

Ser Gly Gly Lys Gly Gly Ser Tyr Ser Gln Ala Ala Cys Ser Asp Ser
                340                 345                 350

Ala Gln Gly Ser Asp Val Ser Leu Thr Ala
                355                 360

<210> SEQ ID NO 7
<211> LENGTH: 1586
<212> TYPE: DNA
<213> ORGANISM: Homo sapiens
<220> FEATURE:
<221> NAME/KEY: CDS
<222> LOCATION: (66)..(1166)

<400> SEQUENCE: 7
tccgcagtcc cggttctaaa gtccccagtc acccacccgg actcacattc tccccagagg    60 ccgag atg cgg gtc atg gcg ccc cga gcc ctc ctc ctg ctg ctc tcg gga   110
      Met Arg Val Met Ala Pro Arg Ala Leu Leu Leu Leu Leu Ser Gly
      1               5                   10                  15 ggc ctg gcc ctg acc gag acc tgg gcc tgc tcc cac tcc atg agg tat    158
Gly Leu Ala Leu Thr Glu Thr Trp Ala Cys Ser His Ser Met Arg Tyr
            20                  25                  30 ttc gac acc gcc gtg tcc cgg ccc ggc cgc gga gag ccc cgc ttc atc    206
Phe Asp Thr Ala Val Ser Arg Pro Gly Arg Gly Glu Pro Arg Phe Ile
        35                  40                  45 tca gtg ggc tac gtg gac gac acg cag ttc gtg cgg ttc gac agc gac    254
Ser Val Gly Tyr Val Asp Asp Thr Gln Phe Val Arg Phe Asp Ser Asp
    50                  55                  60 gcc gcg agt ccg aga ggg gag ccg cgg gcg ccg tgg gtg gag cag gag    302
Ala Ala Ser Pro Arg Gly Glu Pro Arg Ala Pro Trp Val Glu Gln Glu
65                  70                  75 ggg ccg gag tat tgg gac cgg gag aca cag aag tac aag cgc cag gca    350
Gly Pro Glu Tyr Trp Asp Arg Glu Thr Gln Lys Tyr Lys Arg Gln Ala
80                  85                  90                  95 cag gct gac cga gtg agc ctg cgg aac ctg cgc ggc tac tac aac cag    398
Gln Ala Asp Arg Val Ser Leu Arg Asn Leu Arg Gly Tyr Tyr Asn Gln
                100                 105                 110 agc gag gac ggg tct cac acc ctc cag agg atg tct ggc tgc gac ctg    446
Ser Glu Asp Gly Ser His Thr Leu Gln Arg Met Ser Gly Cys Asp Leu
            115                 120                 125 ggg ccc gac ggg cgc ctc ctc cgc ggg tat gac cag tcc gcc tac gac    494
Gly Pro Asp Gly Arg Leu Leu Arg Gly Tyr Asp Gln Ser Ala Tyr Asp
        130                 135                 140 ggc aag gat tac atc gcc ctg aac gag gac ctg cgc tcc tgg acc gcc    542
Gly Lys Asp Tyr Ile Ala Leu Asn Glu Asp Leu Arg Ser Trp Thr Ala
    145                 150                 155 gcg gac acc gcg gct cag atc acc cag cgc aag ttg gag gcg gcc cgt    590
Ala Asp Thr Ala Ala Gln Ile Thr Gln Arg Lys Leu Glu Ala Ala Arg
160                 165                 170                 175 gcg gcg gag cag ctg aga gcc tac ctg gag ggc acg tgc gtg gag tgg    638
Ala Ala Glu Gln Leu Arg Ala Tyr Leu Glu Gly Thr Cys Val Glu Trp
                180                 185                 190 ctc cgc aga tac ctg gag aac ggg aag gag acg ctg cag cgc gca gaa    686
Leu Arg Arg Tyr Leu Glu Asn Gly Lys Glu Thr Leu Gln Arg Ala Glu
            195                 200                 205 ccc cca aag aca cac gtg acc cac cac ccc ctc tct gac cat gag gcc    734
Pro Pro Lys Thr His Val Thr His His Pro Leu Ser Asp His Glu Ala
```

|  |  |  |  |  |  |  |  |  |  |  |  |  |  |  |  |
|---|---|---|---|---|---|---|---|---|---|---|---|---|---|---|---|
|  |  | 210 |  |  |  |  | 215 |  |  |  |  | 220 |  |  |  |

```
acc ctg agg tgc tgg gcc ctg ggc ttc tac cct gcg gag atc aca ctg      782
Thr Leu Arg Cys Trp Ala Leu Gly Phe Tyr Pro Ala Glu Ile Thr Leu
    225                 230                 235 acc tgg cag cgg gat ggg gag gac cag acc cag gac acc gag ctt gtg      830
Thr Trp Gln Arg Asp Gly Glu Asp Gln Thr Gln Asp Thr Glu Leu Val
240                 245                 250                 255 gag acc agg cca gca gga gat gga acc ttc cag aag tgg gca gct gtg      878
Glu Thr Arg Pro Ala Gly Asp Gly Thr Phe Gln Lys Trp Ala Ala Val
                260                 265                 270 gtg gtg cct tct gga caa gag cag aga tac acg tgc cat atg cag cac      926
Val Val Pro Ser Gly Gln Glu Gln Arg Tyr Thr Cys His Met Gln His
            275                 280                 285 gag ggg ctg caa gag ccc ctc acc ctg agc tgg gag cca tct tcc cag      974
Glu Gly Leu Gln Glu Pro Leu Thr Leu Ser Trp Glu Pro Ser Ser Gln
        290                 295                 300 ccc acc atc ccc atc atg ggc atc gtt gct ggc ctg gct gtc ctg gtt     1022
Pro Thr Ile Pro Ile Met Gly Ile Val Ala Gly Leu Ala Val Leu Val
    305                 310                 315 gtc cta gct gtc ctt gga gct gtg gtc acc gct atg atg tgt agg agg     1070
Val Leu Ala Val Leu Gly Ala Val Val Thr Ala Met Met Cys Arg Arg
320                 325                 330                 335 aag agc tca ggt gga aaa gga ggg agc tgc tct cag gct gcg tgc agc     1118
Lys Ser Ser Gly Gly Lys Gly Gly Ser Cys Ser Gln Ala Ala Cys Ser
                340                 345                 350 aac agt gcc cag ggc tct gat gag tct ctc atc act tgt aaa gcc tga     1166
Asn Ser Ala Gln Gly Ser Asp Glu Ser Leu Ile Thr Cys Lys Ala
            355                 360                 365 gacagctgcc tgtgtgggac tgagatgcag gatttcttca ccctctcct ttgtgacttc     1226 aagagcctct ggcatctctt tctgcaaagg cacctgaatg tgtctgcgtt cctgttagca     1286
taatgtgagg aggtggagag acagcccacc ccgtgtcca ccgtgacccc tgtccccaca     1346
ctgacctgtg ttccctcccc gatcatcttt cctgttccag agaggtgggg ctggatgtct     1406
ccatctctgt ctcaaattca tggtgcactg agctgcaact tcttacttcc ctaatgaagt     1466
taagaacctg aatataaatt tgtgttctca aatatttgct atgaagcgtt gatggattaa     1526
ttaaataagt caattcctag aagttgagag agcaaataaa gacctgagaa ccttccagaa     1586
```

<210> SEQ ID NO 8
<211> LENGTH: 366
<212> TYPE: PRT
<213> ORGANISM: Homo sapiens

<400> SEQUENCE: 8

```
Met Arg Val Met Ala Pro Arg Ala Leu Leu Leu Leu Leu Ser Gly Gly
1               5                   10                  15

Leu Ala Leu Thr Glu Thr Trp Ala Cys Ser His Ser Met Arg Tyr Phe
            20                  25                  30

Asp Thr Ala Val Ser Arg Pro Gly Arg Gly Glu Pro Arg Phe Ile Ser
        35                  40                  45

Val Gly Tyr Val Asp Asp Thr Gln Phe Val Arg Phe Asp Ser Asp Ala
    50                  55                  60

Ala Ser Pro Arg Gly Glu Pro Arg Ala Pro Trp Val Glu Gln Glu Gly
65                  70                  75                  80

Pro Glu Tyr Trp Asp Arg Glu Thr Gln Lys Tyr Lys Arg Gln Ala Gln
                85                  90                  95

Ala Asp Arg Val Ser Leu Arg Asn Leu Arg Gly Tyr Tyr Asn Gln Ser
```

```
                    100                 105                 110
Glu Asp Gly Ser His Thr Leu Gln Arg Met Ser Gly Cys Asp Leu Gly
            115                 120                 125

Pro Asp Gly Arg Leu Leu Arg Gly Tyr Asp Gln Ser Ala Tyr Asp Gly
            130                 135                 140

Lys Asp Tyr Ile Ala Leu Asn Glu Asp Leu Arg Ser Trp Thr Ala Ala
145                 150                 155                 160

Asp Thr Ala Ala Gln Ile Thr Gln Arg Lys Leu Glu Ala Ala Arg Ala
                165                 170                 175

Ala Glu Gln Leu Arg Ala Tyr Leu Glu Gly Thr Cys Val Glu Trp Leu
            180                 185                 190

Arg Arg Tyr Leu Glu Asn Gly Lys Glu Thr Leu Gln Arg Ala Glu Pro
            195                 200                 205

Pro Lys Thr His Val Thr His His Pro Leu Ser Asp His Glu Ala Thr
        210                 215                 220

Leu Arg Cys Trp Ala Leu Gly Phe Tyr Pro Ala Glu Ile Thr Leu Thr
225                 230                 235                 240

Trp Gln Arg Asp Gly Glu Asp Gln Thr Gln Asp Thr Glu Leu Val Glu
                245                 250                 255

Thr Arg Pro Ala Gly Asp Gly Thr Phe Gln Lys Trp Ala Ala Val Val
            260                 265                 270

Val Pro Ser Gly Gln Glu Gln Arg Tyr Thr Cys His Met Gln His Glu
        275                 280                 285

Gly Leu Gln Glu Pro Leu Thr Leu Ser Trp Glu Pro Ser Ser Gln Pro
    290                 295                 300

Thr Ile Pro Ile Met Gly Ile Val Ala Gly Leu Ala Val Leu Val Val
305                 310                 315                 320

Leu Ala Val Leu Gly Ala Val Val Thr Ala Met Met Cys Arg Arg Lys
                325                 330                 335

Ser Ser Gly Gly Lys Gly Gly Ser Cys Ser Gln Ala Ala Cys Ser Asn
            340                 345                 350

Ser Ala Gln Gly Ser Asp Glu Ser Leu Ile Thr Cys Lys Ala
        355                 360                 365

<210> SEQ ID NO 9
<211> LENGTH: 2679
<212> TYPE: DNA
<213> ORGANISM: Homo sapiens
<220> FEATURE:
<221> NAME/KEY: CDS
<222> LOCATION: (127)..(1203)

<400> SEQUENCE: 9
gcagactcag ttctcattcc caatgggtgt cgggtttcta gagaagccaa tcagcgtcgc      60
cacgactccc gactataaag tccccatccg gactcaagaa gttctcagga ctcagaggct     120 gggatc atg gta gat gga acc ctc ctt tta ctc ctc tcg gag gcc ctg        168
       Met Val Asp Gly Thr Leu Leu Leu Leu Leu Ser Glu Ala Leu
         1               5                  10 gcc ctt acc cag acc tgg gcg ggc tcc cac tcc ttg aag tat ttc cac       216
Ala Leu Thr Gln Thr Trp Ala Gly Ser His Ser Leu Lys Tyr Phe His
 15                  20                  25                  30 act tcc gtg tcc cgg ccc ggc cgc ggg gag ccc cgc ttc atc tct gtg       264
Thr Ser Val Ser Arg Pro Gly Arg Gly Glu Pro Arg Phe Ile Ser Val
                 35                  40                  45 ggc tac gtg gac gac acc cag ttc gtg cgc ttc gac aac gac gcc gcg       312
Gly Tyr Val Asp Asp Thr Gln Phe Val Arg Phe Asp Asn Asp Ala Ala
```

```
                    50                  55                  60
agt ccg agg atg gtg ccg cgg gcg ccg tgg atg gag cag gag ggg tca      360
Ser Pro Arg Met Val Pro Arg Ala Pro Trp Met Glu Gln Glu Gly Ser
         65                  70                  75 gag tat tgg gac cgg gag aca cgg agc gcc agg gac acc gca cag att      408
Glu Tyr Trp Asp Arg Glu Thr Arg Ser Ala Arg Asp Thr Ala Gln Ile
     80                  85                  90 ttc cga gtg aat ctg cgg acg ctg cgc ggc tac tac aat cag agc gag      456
Phe Arg Val Asn Leu Arg Thr Leu Arg Gly Tyr Tyr Asn Gln Ser Glu
 95                 100                 105                 110 gcc ggg tct cac acc ctg cag tgg atg cat ggc tgc gag ctg ggg ccc      504
Ala Gly Ser His Thr Leu Gln Trp Met His Gly Cys Glu Leu Gly Pro
                115                 120                 125 gac ggg cgc ttc ctc cgc ggg tat gaa cag ttc gcc tac gac ggc aag      552
Asp Gly Arg Phe Leu Arg Gly Tyr Glu Gln Phe Ala Tyr Asp Gly Lys
            130                 135                 140 gat tat ctc acc ctg aat gag gac ctg cgc tcc tgg acc gcg gtg gac      600
Asp Tyr Leu Thr Leu Asn Glu Asp Leu Arg Ser Trp Thr Ala Val Asp
        145                 150                 155 acg gcg gct cag atc tcc gag caa aag tca aat gat gcc tct gag gcg      648
Thr Ala Ala Gln Ile Ser Glu Gln Lys Ser Asn Asp Ala Ser Glu Ala
    160                 165                 170 gag cac cag aga gcc tac ctg gaa gac aca tgc gtg gag tgg ctc cac      696
Glu His Gln Arg Ala Tyr Leu Glu Asp Thr Cys Val Glu Trp Leu His
175                 180                 185                 190 aaa tac ctg gag aag ggg aag gag acg ctg ctt cac ctg gag ccc cca      744
Lys Tyr Leu Glu Lys Gly Lys Glu Thr Leu Leu His Leu Glu Pro Pro
                195                 200                 205 aag aca cac gtg act cac cac ccc atc tct gac cat gag gcc acc ctg      792
Lys Thr His Val Thr His His Pro Ile Ser Asp His Glu Ala Thr Leu
            210                 215                 220 agg tgc tgg gcc ctg ggc ttc tac cct gcg gag atc aca ctg acc tgg      840
Arg Cys Trp Ala Leu Gly Phe Tyr Pro Ala Glu Ile Thr Leu Thr Trp
        225                 230                 235 cag cag gat ggg gag ggc cat acc cag gac acg gag ctc gtg gag acc      888
Gln Gln Asp Gly Glu Gly His Thr Gln Asp Thr Glu Leu Val Glu Thr
    240                 245                 250 agg cct gca ggg gat gga acc ttc cag aag tgg gca gct gtg gtg gtg      936
Arg Pro Ala Gly Asp Gly Thr Phe Gln Lys Trp Ala Ala Val Val Val
255                 260                 265                 270 cct tct gga gag gag cag aga tac acg tgc cat gtg cag cat gag ggg      984
Pro Ser Gly Glu Glu Gln Arg Tyr Thr Cys His Val Gln His Glu Gly
                275                 280                 285 cta ccc gag ccc gtc acc ctg aga tgg aag ccg gct tcc cag ccc acc     1032
Leu Pro Glu Pro Val Thr Leu Arg Trp Lys Pro Ala Ser Gln Pro Thr
            290                 295                 300 atc ccc atc gtg ggc atc att gct ggc ctg gtt ctc ctt gga tct gtg     1080
Ile Pro Ile Val Gly Ile Ile Ala Gly Leu Val Leu Leu Gly Ser Val
        305                 310                 315 gtc tct gga gct gtg gtt gct gct gtg ata tgg agg aag aag agc tca     1128
Val Ser Gly Ala Val Val Ala Ala Val Ile Trp Arg Lys Lys Ser Ser
    320                 325                 330 ggt gga aaa gga ggg agc tac tct aag gct gag tgg agc gac agt gcc     1176
Gly Gly Lys Gly Gly Ser Tyr Ser Lys Ala Glu Trp Ser Asp Ser Ala
335                 340                 345                 350 cag ggg tct gag tct cac agc ttg taa agcctgagac agctgccttg           1223
Gln Gly Ser Glu Ser His Ser Leu
                355 tgtgcgactg agatgcacag ctgccttgtg tgcgactgag atgcaggatt tcctcacgcc   1283
```

```
tcccctatgt gtcttagggg actctggctt ctcttttgc aagggcctct gaatctgtct    1343
gtgtccctgt tagcacaatg tgaggaggta gagaaacagt ccacctctgt gtctaccatg    1403
accccttcc tcacactgac ctgtgttcct tccctgttct cttttctatt aaaaataaga    1463
acctgggcag agtgcggcag ctcatgcctg taatcccagc acttagggag gccgaggagg    1523
gcagatcacg aggtcaggag atcgaaacca tcctggctaa cacggtgaaa ccccgtctct    1583
actaaaaaat acaaaaaatt agctgggcgc agaggcacgg gcctgtagtc ccagctactc    1643
aggaggcgga ggcaggagaa tggcgtcaac ccgggaggcg gaggttgcag tgagccagga    1703
ttgtgcgact gcactccagc ctgggtgaca gggtgaaacg ccatctcaaa aaataaaaat    1763
tgaaaaataa aaaagaaacc tggatctcaa tttaattttt catattcttg caatgaaatg    1823
gacttgagga agctaagatc atagctagaa atacagataa ttccacagca catctctagc    1883
aaatttagcc tattcctatt ctctagccta ttccttacca cctgtaatct tgaccatata    1943
ccttggagtt gaatattgtt ttcatactgc tgtggtttga atgttccctc caacactcat    2003
gttgagactt aatccctaat gtggcaatac tgaaggtgg ggcctttgag atgtgattgg    2063
atcgtaaggc tgtgccttca ttcatgggtt aatggattaa tgggttatca caggaatggg    2123
actggtggct ttataagaag aggaaaagag aactgagcta gcatgcccag cccacagaga    2183
gcctccacta gagtgatgct aagtggaaat gtgaggtgca gctgccacag agggccccca    2243
ccagggaaat gtctagtgtc tagtggatcc aggccacagg agagagtgcc ttgtggagcg    2303
ctggagcag gacctgacca ccaccaggac cccagaactg tggagtcagt ggcagcatgc    2363
agcgccccct tgggaaagct ttaggcacca gcctgcaacc cattcgagca gccacgtagg    2423
ctgcacccag caaagccaca ggcacggggc tacctgaggc cttggggggcc caatccctgc    2483
tccagtgtgt ccgtgaggca gcacacgaag tcaaaagaga ttattctctt cccacagata    2543
cctttctct cccatgaccc tttaacagca tctgcttcat tcccctcacc ttcccaggct    2603
gatctgaggt aaactttgaa gtaaaataaa agctgtgttt gagcatcatt tgtatttcaa    2663
aaaaaaaaaa aaaaaa                                                    2679
```

<210> SEQ ID NO 10
<211> LENGTH: 358
<212> TYPE: PRT
<213> ORGANISM: Homo sapiens

<400> SEQUENCE: 10

Met Val Asp Gly Thr Leu Leu Leu Leu Ser Glu Ala Leu Ala Leu
1               5                   10                  15

Thr Gln Thr Trp Ala Gly Ser His Ser Leu Lys Tyr Phe His Thr Ser
                20                  25                  30

Val Ser Arg Pro Gly Arg Gly Glu Pro Arg Phe Ile Ser Val Gly Tyr
            35                  40                  45

Val Asp Asp Thr Gln Phe Val Arg Phe Asp Asn Asp Ala Ala Ser Pro
        50                  55                  60

Arg Met Val Pro Arg Ala Pro Trp Met Glu Gln Glu Gly Ser Glu Tyr
65                  70                  75                  80

Trp Asp Arg Glu Thr Arg Ser Ala Arg Asp Thr Ala Gln Ile Phe Arg
                85                  90                  95

Val Asn Leu Arg Thr Leu Arg Gly Tyr Tyr Asn Gln Ser Glu Ala Gly
            100                 105                 110

Ser His Thr Leu Gln Trp Met His Gly Cys Glu Leu Gly Pro Asp Gly

```
            115                 120                 125
Arg Phe Leu Arg Gly Tyr Glu Gln Phe Ala Tyr Asp Gly Lys Asp Tyr
    130                 135                 140

Leu Thr Leu Asn Glu Asp Leu Arg Ser Trp Thr Ala Val Asp Thr Ala
145                 150                 155                 160

Ala Gln Ile Ser Glu Gln Lys Ser Asn Asp Ala Ser Glu Ala Glu His
                165                 170                 175

Gln Arg Ala Tyr Leu Glu Asp Thr Cys Val Glu Trp Leu His Lys Tyr
            180                 185                 190

Leu Glu Lys Gly Lys Glu Thr Leu Leu His Leu Glu Pro Pro Lys Thr
        195                 200                 205

His Val Thr His His Pro Ile Ser Asp His Glu Ala Thr Leu Arg Cys
    210                 215                 220

Trp Ala Leu Gly Phe Tyr Pro Ala Glu Ile Thr Leu Thr Trp Gln Gln
225                 230                 235                 240

Asp Gly Glu Gly His Thr Gln Asp Thr Glu Leu Val Glu Thr Arg Pro
                245                 250                 255

Ala Gly Asp Gly Thr Phe Gln Lys Trp Ala Ala Val Val Val Pro Ser
            260                 265                 270

Gly Glu Glu Gln Arg Tyr Thr Cys His Val Gln His Glu Gly Leu Pro
        275                 280                 285

Glu Pro Val Thr Leu Arg Trp Lys Pro Ala Ser Gln Pro Thr Ile Pro
    290                 295                 300

Ile Val Gly Ile Ile Ala Gly Leu Val Leu Leu Gly Ser Val Val Ser
305                 310                 315                 320

Gly Ala Val Val Ala Ala Val Ile Trp Arg Lys Lys Ser Ser Gly Gly
                325                 330                 335

Lys Gly Gly Ser Tyr Ser Lys Ala Glu Trp Ser Asp Ser Ala Gln Gly
            340                 345                 350

Ser Glu Ser His Ser Leu
        355

<210> SEQ ID NO 11
<211> LENGTH: 1301
<212> TYPE: DNA
<213> ORGANISM: Homo sapiens
<220> FEATURE:
<221> NAME/KEY: CDS
<222> LOCATION: (125)..(1165)

<400> SEQUENCE: 11
tttctcactc ccattgggcg tcgcgtttct agagaagcca atcagtgtcg ccgcagttcc      60
caggttctaa agtcccacgc accccgcggg actcatattt ttcccagacg cggaggttgg     120 ggtc atg gcg ccc cga agc ctc ctc ctg ctg ctc tca ggg gcc ctg gcc     169
     Met Ala Pro Arg Ser Leu Leu Leu Leu Leu Ser Gly Ala Leu Ala
     1               5                   10                  15 ctg acc gat act tgg gcg ggc tcc cac tcc ttg agg tat ttc agc acc     217
Leu Thr Asp Thr Trp Ala Gly Ser His Ser Leu Arg Tyr Phe Ser Thr
             20                  25                  30 gct gtg tcg cgg ccc ggc cgc ggg gag ccc cgc tac atc gcc gtg gag     265
Ala Val Ser Arg Pro Gly Arg Gly Glu Pro Arg Tyr Ile Ala Val Glu
        35                  40                  45 tac gta gac gac acg caa ttc ctg cgg ttc gac agc gac gcc gcg att     313
Tyr Val Asp Asp Thr Gln Phe Leu Arg Phe Asp Ser Asp Ala Ala Ile
    50                  55                  60 ccg agg atg gag ccg cgg gag ccg tgg gtg gag caa gag ggg ccg cag     361
```

```
                Pro Arg Met Glu Pro Arg Glu Pro Trp Val Glu Gln Glu Gly Pro Gln
                        65                  70                  75 tat tgg gag tgg acc aca ggg tac gcc aag gcc aac gca cag act gac              409
Tyr Trp Glu Trp Thr Thr Gly Tyr Ala Lys Ala Asn Ala Gln Thr Asp
 80                  85                  90                  95 cga gtg gcc ctg agg aac ctg ctc cgc gcc tac aac cag agc gag gct              457
Arg Val Ala Leu Arg Asn Leu Leu Arg Arg Tyr Asn Gln Ser Glu Ala
                100                 105                 110 ggg tct cac acc ctc cag gga atg aat ggc tgc gac atg ggg ccc gac              505
Gly Ser His Thr Leu Gln Gly Met Asn Gly Cys Asp Met Gly Pro Asp
            115                 120                 125 gga cgc ctc ctc cgc ggg tat cac cag cac gcg tac gac ggc aag gat              553
Gly Arg Leu Leu Arg Gly Tyr His Gln His Ala Tyr Asp Gly Lys Asp
        130                 135                 140 tac atc tcc ctg aac gag gac ctg cgc tcc tgg acc gcg gcg gac acc              601
Tyr Ile Ser Leu Asn Glu Asp Leu Arg Ser Trp Thr Ala Ala Asp Thr
    145                 150                 155 gtg gct cag atc acc cag cgc ttc tat gag gca gag gaa tat gca gag              649
Val Ala Gln Ile Thr Gln Arg Phe Tyr Glu Ala Glu Glu Tyr Ala Glu
160                 165                 170                 175 gag ttc agg acc tac ctg gag ggc gag tgc ctg gag ttg ctc cgc aga              697
Glu Phe Arg Thr Tyr Leu Glu Gly Glu Cys Leu Glu Leu Leu Arg Arg
                180                 185                 190 tac ttg gag aat ggg aag gag acg cta cag cgc gca gat cct cca aag              745
Tyr Leu Glu Asn Gly Lys Glu Thr Leu Gln Arg Ala Asp Pro Pro Lys
            195                 200                 205 gca cac gtt gcc cac cac ccc atc tct gac cat gag gcc acc ctg agg              793
Ala His Val Ala His His Pro Ile Ser Asp His Glu Ala Thr Leu Arg
        210                 215                 220 tgc tgg gcc ctg ggc ttc tac cct gcg gag atc acg ctg acc tgg cag              841
Cys Trp Ala Leu Gly Phe Tyr Pro Ala Glu Ile Thr Leu Thr Trp Gln
    225                 230                 235 cgg gat ggg gag gaa cag acc cag gac aca gag ctt gtg gag acc agg              889
Arg Asp Gly Glu Glu Gln Thr Gln Asp Thr Glu Leu Val Glu Thr Arg
240                 245                 250                 255 cct gca ggg gat gga acc ttc cag aag tgg gcc gct gtg gtg gtg cct              937
Pro Ala Gly Asp Gly Thr Phe Gln Lys Trp Ala Ala Val Val Val Pro
                260                 265                 270 cct gga gag gaa cag aga tac aca tgc cat gtg cag cac gag ggg ctg              985
Pro Gly Glu Glu Gln Arg Tyr Thr Cys His Val Gln His Glu Gly Leu
            275                 280                 285 ccc cag ccc ctc atc ctg aga tgg gag cag tct ccc cag ccc acc atc             1033
Pro Gln Pro Leu Ile Leu Arg Trp Glu Gln Ser Pro Gln Pro Thr Ile
        290                 295                 300 ccc atc gtg ggc atc gtt gct ggc ctt gtt gtc ctt gga gct gtg gtc             1081
Pro Ile Val Gly Ile Val Ala Gly Leu Val Val Leu Gly Ala Val Val
    305                 310                 315 act gga gct gtg gtc gct gct gtg atg tgg agg aag aag agc tca gat             1129
Thr Gly Ala Val Val Ala Ala Val Met Trp Arg Lys Lys Ser Ser Asp
320                 325                 330                 335 aga aac aga ggg agc tac tct cag gct gca gtg tga gacagcttcc                  1175
Arg Asn Arg Gly Ser Tyr Ser Gln Ala Ala Val
                340                 345 ttgtgtggga ctgagaagca agatatcaat gtagcagaat tgcacttgtg cctcacgaac           1235
atacataaat tttaaaaata aagaataaaa atatatcttt ttatagataa aaaaaaaaa            1295 aaaaaa                                                                     1301

<210> SEQ ID NO 12
```

<211> LENGTH: 346
<212> TYPE: PRT
<213> ORGANISM: Homo sapiens

<400> SEQUENCE: 12

```
Met Ala Pro Arg Ser Leu Leu Leu Leu Ser Gly Ala Leu Ala Leu
1               5                   10                  15

Thr Asp Thr Trp Ala Gly Ser His Ser Leu Arg Tyr Phe Ser Thr Ala
            20                  25                  30

Val Ser Arg Pro Gly Arg Gly Glu Pro Arg Tyr Ile Ala Val Glu Tyr
        35                  40                  45

Val Asp Asp Thr Gln Phe Leu Arg Phe Asp Ser Asp Ala Ala Ile Pro
50                  55                  60

Arg Met Glu Pro Arg Glu Pro Trp Val Glu Gln Gly Pro Gln Tyr
65                  70                  75                  80

Trp Glu Trp Thr Thr Gly Tyr Ala Lys Ala Asn Ala Gln Thr Asp Arg
            85                  90                  95

Val Ala Leu Arg Asn Leu Leu Arg Arg Tyr Asn Gln Ser Glu Ala Gly
            100                 105                 110

Ser His Thr Leu Gln Gly Met Asn Gly Cys Asp Met Gly Pro Asp Gly
        115                 120                 125

Arg Leu Leu Arg Gly Tyr His Gln His Ala Tyr Asp Gly Lys Asp Tyr
130                 135                 140

Ile Ser Leu Asn Glu Asp Leu Arg Ser Trp Thr Ala Ala Asp Thr Val
145                 150                 155                 160

Ala Gln Ile Thr Gln Arg Phe Tyr Glu Ala Glu Tyr Ala Glu Glu
            165                 170                 175

Phe Arg Thr Tyr Leu Glu Gly Glu Cys Leu Glu Leu Leu Arg Arg Tyr
            180                 185                 190

Leu Glu Asn Gly Lys Glu Thr Leu Gln Arg Ala Asp Pro Pro Lys Ala
            195                 200                 205

His Val Ala His His Pro Ile Ser Asp His Glu Ala Thr Leu Arg Cys
        210                 215                 220

Trp Ala Leu Gly Phe Tyr Pro Ala Glu Ile Thr Leu Thr Trp Gln Arg
225                 230                 235                 240

Asp Gly Glu Glu Gln Thr Gln Asp Thr Glu Leu Val Glu Thr Arg Pro
                245                 250                 255

Ala Gly Asp Gly Thr Phe Gln Lys Trp Ala Ala Val Val Pro Pro
            260                 265                 270

Gly Glu Glu Gln Arg Tyr Thr Cys His Val Gln His Glu Gly Leu Pro
        275                 280                 285

Gln Pro Leu Ile Leu Arg Trp Glu Gln Ser Pro Gln Pro Thr Ile Pro
    290                 295                 300

Ile Val Gly Ile Val Ala Gly Leu Val Val Leu Gly Ala Val Val Thr
305                 310                 315                 320

Gly Ala Val Val Ala Ala Val Met Trp Arg Lys Lys Ser Ser Asp Arg
                325                 330                 335

Asn Arg Gly Ser Tyr Ser Gln Ala Ala Val
                340                 345
```

<210> SEQ ID NO 13
<211> LENGTH: 1578
<212> TYPE: DNA
<213> ORGANISM: Homo sapiens
<220> FEATURE:
<221> NAME/KEY: CDS

<222> LOCATION: (179)..(1195)

<400> SEQUENCE: 13

```
agtgtggtac tttgtcttga ggagatgtcc tggactcaca cggaaactta gggctacgga    60
atgaagttct cactcccatt aggtgacagg tttttagaga agccaatcag cgtcgccgcg   120
gtcctggttc taaagtcctc gctcacccac ccggactcat tctccccaga cgccaagg    178
```

| | | | | | | | | | | | | | | | | |
|---|---|---|---|---|---|---|---|---|---|---|---|---|---|---|---|---|
| atg | gtg | gtc | atg | gcg | ccc | cga | acc | ctc | ttc | ctg | ctg | ctc | tcg | ggg | gcc | 226 |
| Met | Val | Val | Met | Ala | Pro | Arg | Thr | Leu | Phe | Leu | Leu | Leu | Ser | Gly | Ala | |
| 1 | | | 5 | | | | | 10 | | | | | 15 | | | |

| ctg | acc | ctg | acc | gag | acc | tgg | gcg | ggc | tcc | cac | tcc | atg | agg | tat | ttc | 274 |
|---|---|---|---|---|---|---|---|---|---|---|---|---|---|---|---|---|
| Leu | Thr | Leu | Thr | Glu | Thr | Trp | Ala | Gly | Ser | His | Ser | Met | Arg | Tyr | Phe | |
| | | 20 | | | | | 25 | | | | | 30 | | | | |

| agc | gcc | gcc | gtg | tcc | cgg | ccc | ggc | cgc | ggg | gag | ccc | cgc | ttc | atc | gcc | 322 |
|---|---|---|---|---|---|---|---|---|---|---|---|---|---|---|---|---|
| Ser | Ala | Ala | Val | Ser | Arg | Pro | Gly | Arg | Gly | Glu | Pro | Arg | Phe | Ile | Ala | |
| 35 | | | | | 40 | | | | | 45 | | | | | | |

| atg | ggc | tac | gtg | gac | gac | acg | cag | ttc | gtg | cgg | ttc | gac | agc | gac | tcg | 370 |
|---|---|---|---|---|---|---|---|---|---|---|---|---|---|---|---|---|
| Met | Gly | Tyr | Val | Asp | Asp | Thr | Gln | Phe | Val | Arg | Phe | Asp | Ser | Asp | Ser | |
| | 50 | | | | | 55 | | | | | 60 | | | | | |

| gcg | tgt | ccg | agg | atg | gag | ccg | cgg | gcg | ccg | tgg | gtg | gag | cag | gag | ggg | 418 |
|---|---|---|---|---|---|---|---|---|---|---|---|---|---|---|---|---|
| Ala | Cys | Pro | Arg | Met | Glu | Pro | Arg | Ala | Pro | Trp | Val | Glu | Gln | Glu | Gly | |
| 65 | | | | 70 | | | | | 75 | | | | | 80 | | |

| ccg | gag | tat | tgg | gaa | gag | gag | aca | cgg | aac | acc | aag | gcc | cac | gca | cag | 466 |
|---|---|---|---|---|---|---|---|---|---|---|---|---|---|---|---|---|
| Pro | Glu | Tyr | Trp | Glu | Glu | Glu | Thr | Arg | Asn | Thr | Lys | Ala | His | Ala | Gln | |
| | | | | 85 | | | | | 90 | | | | | 95 | | |

| act | gac | aga | atg | aac | ctg | cag | acc | ctg | cgc | ggc | tac | tac | aac | cag | agc | 514 |
|---|---|---|---|---|---|---|---|---|---|---|---|---|---|---|---|---|
| Thr | Asp | Arg | Met | Asn | Leu | Gln | Thr | Leu | Arg | Gly | Tyr | Tyr | Asn | Gln | Ser | |
| | | | 100 | | | | | 105 | | | | | 110 | | | |

| gag | gcc | agt | tct | cac | acc | ctc | cag | tgg | atg | att | ggc | tgc | gac | ctg | ggg | 562 |
|---|---|---|---|---|---|---|---|---|---|---|---|---|---|---|---|---|
| Glu | Ala | Ser | Ser | His | Thr | Leu | Gln | Trp | Met | Ile | Gly | Cys | Asp | Leu | Gly | |
| | | 115 | | | | | 120 | | | | | 125 | | | | |

| tcc | gac | gga | cgc | ctc | ctc | cgc | ggg | tat | gaa | cag | tat | gcc | tac | gat | ggc | 610 |
|---|---|---|---|---|---|---|---|---|---|---|---|---|---|---|---|---|
| Ser | Asp | Gly | Arg | Leu | Leu | Arg | Gly | Tyr | Glu | Gln | Tyr | Ala | Tyr | Asp | Gly | |
| | 130 | | | | | 135 | | | | | 140 | | | | | |

| aag | gat | tac | ctc | gcc | ctg | aac | gag | gac | ctg | cgc | tcc | tgg | acc | gca | gcg | 658 |
|---|---|---|---|---|---|---|---|---|---|---|---|---|---|---|---|---|
| Lys | Asp | Tyr | Leu | Ala | Leu | Asn | Glu | Asp | Leu | Arg | Ser | Trp | Thr | Ala | Ala | |
| 145 | | | | 150 | | | | | 155 | | | | | 160 | | |

| gac | act | gcg | gct | cag | atc | tcc | aag | cgc | aag | tgt | gag | gcg | gcc | aat | gtg | 706 |
|---|---|---|---|---|---|---|---|---|---|---|---|---|---|---|---|---|
| Asp | Thr | Ala | Ala | Gln | Ile | Ser | Lys | Arg | Lys | Cys | Glu | Ala | Ala | Asn | Val | |
| | | | 165 | | | | | 170 | | | | | 175 | | | |

| gct | gaa | caa | agg | aga | gcc | tac | ctg | gag | ggc | acg | tgc | gtg | gag | tgg | ctc | 754 |
|---|---|---|---|---|---|---|---|---|---|---|---|---|---|---|---|---|
| Ala | Glu | Gln | Arg | Arg | Ala | Tyr | Leu | Glu | Gly | Thr | Cys | Val | Glu | Trp | Leu | |
| | | 180 | | | | | 185 | | | | | 190 | | | | |

| cac | aga | tac | ctg | gag | aac | ggg | aag | gag | atg | ctg | cag | cgc | gcg | gac | ccc | 802 |
|---|---|---|---|---|---|---|---|---|---|---|---|---|---|---|---|---|
| His | Arg | Tyr | Leu | Glu | Asn | Gly | Lys | Glu | Met | Leu | Gln | Arg | Ala | Asp | Pro | |
| | 195 | | | | | 200 | | | | | 205 | | | | | |

| ccc | aag | aca | cac | gtg | acc | cac | cac | cct | gtc | ttt | gac | tat | gag | gcc | acc | 850 |
|---|---|---|---|---|---|---|---|---|---|---|---|---|---|---|---|---|
| Pro | Lys | Thr | His | Val | Thr | His | His | Pro | Val | Phe | Asp | Tyr | Glu | Ala | Thr | |
| 210 | | | | 215 | | | | | 220 | | | | | | | |

| ctg | agg | tgc | tgg | gcc | ctg | ggc | ttc | tac | cct | gcg | gag | atc | ata | ctg | acc | 898 |
|---|---|---|---|---|---|---|---|---|---|---|---|---|---|---|---|---|
| Leu | Arg | Cys | Trp | Ala | Leu | Gly | Phe | Tyr | Pro | Ala | Glu | Ile | Ile | Leu | Thr | |
| 225 | | | | 230 | | | | | 235 | | | | | 240 | | |

| tgg | cag | cgg | gat | ggg | gag | gac | cag | acc | cag | gac | gtg | gag | ctc | gtg | gag | 946 |
|---|---|---|---|---|---|---|---|---|---|---|---|---|---|---|---|---|
| Trp | Gln | Arg | Asp | Gly | Glu | Asp | Gln | Thr | Gln | Asp | Val | Glu | Leu | Val | Glu | |
| | | | | 245 | | | | | 250 | | | | | 255 | | |

| acc | agg | cct | gca | ggg | gat | gga | acc | ttc | cag | aag | tgg | gca | gct | gtg | gtg | 994 |
|---|---|---|---|---|---|---|---|---|---|---|---|---|---|---|---|---|
| Thr | Arg | Pro | Ala | Gly | Asp | Gly | Thr | Phe | Gln | Lys | Trp | Ala | Ala | Val | Val | |
| | | | 260 | | | | | 265 | | | | | 270 | | | |

| gtg | cct | tct | gga | gag | gag | cag | aga | tac | acg | tgc | cat | gtg | cag | cat | gag | 1042 |
|---|---|---|---|---|---|---|---|---|---|---|---|---|---|---|---|---|

```
                                                                              -continued Val Pro Ser Gly Glu Glu Gln Arg Tyr Thr Cys His Val Gln His Glu
        275                 280                 285 ggg ctg ccg gag ccc ctc atg ctg aga tgg aag cag tct tcc ctg ccc        1090
Gly Leu Pro Glu Pro Leu Met Leu Arg Trp Lys Gln Ser Ser Leu Pro
    290                 295                 300 acc atc ccc atc atg ggt atc gtt gct ggc ctg gtt gtc ctt gca gct        1138
Thr Ile Pro Ile Met Gly Ile Val Ala Gly Leu Val Val Leu Ala Ala
305                 310                 315                 320 gta gtc act gga gct gcg gtc gct gct gtg ctg tgg aga aag aag agc        1186
Val Val Thr Gly Ala Ala Val Ala Ala Val Leu Trp Arg Lys Lys Ser
                325                 330                 335 tca gat tga aaaggaggga gctactctca ggctgcaatg tgaaacagct               1235
Ser Asp gccctgtgtg ggactgagtg gcaagtccct ttgtgacttc aagaaccctg actcctcttt     1295
gtgcagagac cagcccaccc ctgtgccac catgaccctc ttcctcatgc tgaactgcat      1355
tccttcccca atcaccttc ctgttccaga aaagggctg ggatgtctcc gtctctgtct       1415
caaatttgtg gtccactgag ctataactta cttctgtatt aaaattagaa tctgagtata    1475
aatttacttt ttcaaattat ttccaagaga gattgatggg ttaattaaag gagaagattc    1535
ctgaaatttg agagacaaaa taaatggaag acatgagaac ttt                       1578

<210> SEQ ID NO 14
<211> LENGTH: 338
<212> TYPE: PRT
<213> ORGANISM: Homo sapiens

<400> SEQUENCE: 14

Met Val Val Met Ala Pro Arg Thr Leu Phe Leu Leu Leu Ser Gly Ala
1               5                  10                 15

Leu Thr Leu Thr Glu Thr Trp Ala Gly Ser His Ser Met Arg Tyr Phe
                20                 25                 30

Ser Ala Ala Val Ser Arg Pro Gly Arg Gly Glu Pro Arg Phe Ile Ala
            35                 40                 45

Met Gly Tyr Val Asp Asp Thr Gln Phe Val Arg Phe Asp Ser Asp Ser
        50                 55                 60

Ala Cys Pro Arg Met Glu Pro Arg Ala Pro Trp Val Glu Gln Glu Gly
65              70                 75                 80

Pro Glu Tyr Trp Glu Glu Glu Thr Arg Asn Thr Lys Ala His Ala Gln
                85                 90                 95

Thr Asp Arg Met Asn Leu Gln Thr Leu Arg Gly Tyr Tyr Asn Gln Ser
            100                105                110

Glu Ala Ser Ser His Thr Leu Gln Trp Met Ile Gly Cys Asp Leu Gly
        115                120                125

Ser Asp Gly Arg Leu Leu Arg Gly Tyr Glu Gln Tyr Ala Tyr Asp Gly
    130                135                140

Lys Asp Tyr Leu Ala Leu Asn Glu Asp Leu Arg Ser Trp Thr Ala Ala
145             150                155                160

Asp Thr Ala Ala Gln Ile Ser Lys Arg Lys Cys Glu Ala Ala Asn Val
                165                170                175

Ala Glu Gln Arg Arg Ala Tyr Leu Glu Gly Thr Cys Val Glu Trp Leu
            180                185                190

His Arg Tyr Leu Glu Asn Gly Lys Glu Met Leu Gln Arg Ala Asp Pro
        195                200                205

Pro Lys Thr His Val Thr His His Pro Val Phe Asp Tyr Glu Ala Thr
    210                215                220
```

| | | | | | | | | | | | |
|---|---|---|---|---|---|---|---|---|---|---|---|
| Leu | Arg | Cys | Trp | Ala | Leu | Gly | Phe | Tyr | Pro | Ala | Glu | Ile | Ile | Leu | Thr |
| 225 | | | | 230 | | | | 235 | | | | 240 |

Leu Arg Cys Trp Ala Leu Gly Phe Tyr Pro Ala Glu Ile Ile Leu Thr
225                 230                 235                 240

Trp Gln Arg Asp Gly Glu Asp Gln Thr Gln Asp Val Glu Leu Val Glu
            245                 250                 255

Thr Arg Pro Ala Gly Asp Gly Thr Phe Gln Lys Trp Ala Ala Val Val
        260                 265                 270

Val Pro Ser Gly Glu Glu Gln Arg Tyr Thr Cys His Val Gln His Glu
    275                 280                 285

Gly Leu Pro Glu Pro Leu Met Leu Arg Trp Lys Gln Ser Ser Leu Pro
290                 295                 300

Thr Ile Pro Ile Met Gly Ile Val Ala Gly Leu Val Leu Ala Ala
305                 310                 315                 320

Val Val Thr Gly Ala Ala Val Ala Ala Val Leu Trp Arg Lys Lys Ser
                325                 330                 335

Ser Asp

<210> SEQ ID NO 15
<211> LENGTH: 9232
<212> TYPE: DNA
<213> ORGANISM: Artificial Sequence
<220> FEATURE:
<223> OTHER INFORMATION: Vector sequence for human B2M-HLA-A0201 fusion
      protein

<400> SEQUENCE: 15
ctcgaggagc ttggcccatt gcatacgttg tatccatatc ataatatgta catttatatt     60
ggctcatgtc caacattacc gccatgttga cattgattat tgactagtta ttaatagtaa    120
tcaattacgg ggtcattagt tcatagccca tatatggagt tccgcgttac ataacttacg    180
gtaaatggcc cgcctggctg accgcccaac gacccccgcc cattgacgtc aataatgacg    240
tatgttccca tagtaacgcc aatagggact ttccattgac gtcaatgggt ggagtattta    300
cgctaaactg cccacttggc agtacatcaa gtgtatcata tgccaagtac gccccctatt    360
gacgtcaatg acggtaaatg gcccgcctgg cattatgccc agtacatgac cttatgggac    420
tttcctactt ggcagtacat ctacgtatta gtcatcgcta ttaccatggt gatgcggttt    480
tggcagtaca tcaatgggcg tggatagcgg tttgactcac ggggatttcc aagtctccac    540
cccattgacg tcaatgggag tttgttttgg caccaaaatc aacgggactt tccaaaatgt    600
cgtaacaact ccgccccatt gacgcaaatg ggcggtaggc gtgtacggtg gaggtctat    660 ataagcagag cttctagatt gtacgggagc tcttcactac tcgctgcgtc gagagtgtac    720
gagactctcc aggtttggta agaaatattt tatattgtta taatgttact atgatccatt    780
aacactctgc ttatagattg taagggtgat tgcaatgctt tctgcataaa actttggttt    840
tcttgttaat caataaaccg acttgattcg agaacctact catatattat tgtctctttt    900
atactttatt aagtaaaagg atttgtatat tagccttgct aagggagaca tctagtgata    960
taagtgtgaa ctacacttat cttaaatgat gtaactcctt aggataatca atatacaaaa   1020
ttccatgaca attggcgccc aacgtggggc tcgaatataa gtcgggttta tttgtaaatt   1080
atccctaggg acctccgagc aagcgagcat agcgggaggc atataaaagc caatagacaa   1140
tggctagcag gaagtaatgt tgaagaatat gaacttgatg ttgaagctct ggttgtaatt   1200
ttaagagata gaaatatacc aagaaatcct ttacatggag aagttatagg tcttcgcctt   1260
actgaaggat ggtggggaca aattgagaga tttcagatgg tacgttgatc taaggctatg   1320

```
gatttggcca tgggacaaga atattagtt tatagtccca ttgtatctat gactaaaata   1380
caaaaaactc cactaccaga aagaaaagct ttacccatta gatggataac atggatgact   1440
tatttagaag atccaagaat ccaatttcat tatgataaaa ccttaccaga acttaagcat   1500
attccagatg tatatacatc tagtcagtct cctgttaaac atccttctca atatgaagga   1560
gtgttttata ctgatggctc ggccatcaaa agtcctgatc ctacaaaaag caataatgct   1620
ggcatgggaa tagtacatgc cacatacaaa cctgaatatc aagttttgaa tcaatggtca   1680
ataccactag gtaatcatac tgctcagatg gctgaaatag ctgcagttga atttgcctgt   1740
aaaaaagctt taaaaatacc tggtcctgta ttagttataa ctgatagttt ctatgtagca   1800
gaaagtgcta ataagaatt accatactgg aaatctaatg ggtttgttaa taataagaaa   1860
aagcctctta acatatctc caaatggaaa tctattgctg agtgtttatc tatgaaacca   1920
gacattacta ttcaacatga aaaggcatc agcctacaaa taccagtatt catactgaaa   1980
ggcaatgccc tagcagataa gcttgccacc aaggaagtt atgtggttaa ttgtaatacc   2040
aaaaaaccaa acctggatgc agagttggat caattattac agggtcatta tataaaagga   2100
tatcccaaac aatatacata tttttagaa gatggcaaag taaagttttc cagacctgaa   2160
ggggttaaaa ttattccccc tcagtcagac agacaaaaaa ttgtgcttca agcccacaat   2220
ttggctcaca ccggacgtga agccactctt ttaaaaattg ccaaccttta ttggtggcca   2280
aatatgagaa aggatgtggt taaacaacta ggacgctgtc aacagtgttt aatcacaaat   2340
gcttccaaca aagcctctgg tcctattcta agaccagata ggcctcaaaa acctttttgat   2400 aaattcttta ttgactatat tggaccttta ccaccttcac agggatacct atatgtatta   2460
gtagttgttg atggaatgac aggattcact tggttatacc ccactaaggc tccttctact   2520
agcgcaactg ttaaatctct caatgtactc actagtattg caattccaaa ggtgattcac   2580
tctgatcaag gtgcagcatt cacttcttca acctttgctg aatgggcaaa ggaaagaggt   2640
atacatttgg aattcagtac tccttatcac ccccaaagtg gtagtaaggt ggaaaggaaa   2700
aatagtgata taaaacgact tttaactaaa ctgctagtag aagacccac aaagtggtat   2760 gacctattgc ctgttgtaca acttgcttta aacaacacct atagccctgt attaaaatat   2820
actccacatc aactcttatt tggtatagat tcaaatactc catttgcaaa tcaagataca   2880
cttgacttga ccagagaaga agaacttttct cttttacagg aaattcgtac ttctttatac   2940
catccatcca ccccctccagc ctcctctcgt tcctggtctc ctgttgttgg ccaattggtc   3000
caggagaggg tggctaggcc tgcttctttg agacctcgtt ggcataaacc gtctactgta   3060
cttaaggtgt tgaatccaag gactgttgtt attttggacc atcttggcaa caacagaact   3120
gtaagtatag ataatttaaa acctacttct catcagaatg gcaccaccaa tgacactgca   3180
acaatggatc atttggaaaa aaatgaataa agcgcatgag gcacttcaaa atacaacaac   3240
tgtgactgaa cagcagaagg aacaaattat actggacatt caaaatgaag aagtacaacc   3300
aactaggaga gataaattta gatatctgct ttatacttgt tgtgctacta gctcaagagt   3360
attggcctgg atgtttttag tttgtatatt gttaatcatt gttttggttt catgctttgt   3420
gactatatcc agaatacaat ggaataagga tattcaggta ttaggacctg taatagactg   3480
gaatgttact caaagagctg tttatcaacc cttacagact agaaggattg cacgttccct   3540
tagaatgcag catcctgttc caaaatatgt ggaggtaaat atgactagta ttccacaagg   3600
tgtatactat gaaccccatc cggcctcgac ggtatcgatg gtaccggtat cgataagctt   3660
gataacctcg agagatctaa ttctaccggg taggggaggc gcttttccca aggcagtctg   3720
```

```
gagcatgcgc tttagcagcc ccgctggcac ttggcgctac acaagtggcc tctggcctcg    3780
cacacattcc acatccaccg gtagcgccaa ccggctccgt tctttggtgg ccccttcgcg    3840
ccacttctac tcctccccta gtcaggaagt ttcccccagc aagctcgcgt cgtgcaggac    3900
gtgacaaatg gaagtagcac gtctcactag tctcgtgcag atggacagca ccgctgagca    3960
atggaagcgg gtaggccttt ggggcagcgg ccaatagcag ctttgttcct tcgctttctg    4020
ggctcagagg ctgggaaggg gtgggtccgg gggcgggctc aggggcgggc tcaggggcgg    4080
gcgggcgccc gaaggtcctc ccgaggcccg gcattctgca cgcttcaaaa gcgcacgtct    4140
gccgcgctgt tctcctcttc ctcatctccg ggcctttcga cctgcagccc ggggatcga    4200 tcctaggtga tttaaatcca ccatgaccga gtacaagccc acggtgcgcc tcgccacccg    4260
cgacgacgtc ccccgggccg tacgcaccct cgccgccgcg ttcgccgact accccgccac    4320
gcgccacacc gtcgacccgg accgccacat cgagcgggtc accgagctgc aagaactctt    4380
cctcacgcgc gtcgggctcg acatcggcaa ggtgtgggtc gcggacgacg gcgccgcggt    4440
ggcggtctgg accacgccgg agagcgtcga agcggggcg gtgttcgccg agatcggccc    4500
gcgcatggcc gagttgagcg gttcccggct ggccgcgcag caacagatgg aaggcctcct    4560
ggcgccgcac cggcccaagg agcccgcgtg gttcctggcc accgtcggcg tctcgcccga    4620
ccaccagggc aagggtctgg gcagcgccgt cgtgctcccc ggagtggagg cggccgagcg    4680
cgccggggtg cccgccttcc tggagacctc cgcgccccgc aacctcccct tctacgagcg    4740
gctcggcttc accgtcaccg ccgacgtcga gtgcccgaag accgcgcga cctggtgcat    4800 gacccgcaag cccggtgcct gacggatcca tcgctccggt gccgtcagt gggcagagcg    4860 cacatcgccc acagtccccg agaagttggg gggaggggtc ggcaattgaa ccggtgccta    4920
gagaaggtgg cgcggggtaa actgggaaag tgatgtcgtg tactggctcc gccttttcc    4980 cgagggtggg ggagaaccgt atataagtgc agtagtcgcc gtgaacgttc tttttcgcaa    5040
cgggtttgcc gccagaacac agctgcggcc gcgccgccac catgtctcgc tccgtggcct    5100
tagctgtgct cgcgctactc tctctttctg gcctggaggc tatccagcgt actccaaaga    5160
ttcaggttta ctcacgtcat ccagcagaga atggaaagtc aaatttcctg aattgctatg    5220
tgtctgggtt tcatccatcc gacattgaag ttgacttact gaagaatgga gagagaattg    5280
aaaaagtgga gcattcagac ttgtctttca gcaaggactg tctttctat ctcttgtact    5340 acactgaatt cacccccact gaaaaagatg agtatgcctg ccgtgtgaac catgtgactt    5400
tgtcacagcc caagatagtt aagtgggatc gagacatggg cggaggcgga agcggggcg    5460 gcggatccgg cggaggcgga agcggcggcg ggggaagcgg ctctcactcc atgaggtatt    5520
tcttcacatc cgtgtcccgg cccggccgcg gggagcccg cttcatcgca gtgggctacg    5580
tggacgacac gcagttcgtg cggttcgaca gcgacgccgc gagccagagg atggagccgc    5640
gggcgccgtg gatagagcag gagggtccgg agtattggga cggggagaca cggaaagtga    5700
aggcccactc acagactcac cgagtggacc tggggaccct gcgcggctac tacaaccaga    5760
gcgaggccgg ttctcacacc gtccagagga tgtatggctg cgacgtgggg tcggactggc    5820
gcttcctccg cgggtaccac cagtacgcct acgacgcaa ggattacatc gccctgaaag    5880
aggacctgcg ctcttggacc gcggcggaca tggcagctca gaccaccaag cacaagtggg    5940
aggcggccca tgtggcggag cagttgagag cctacctgga gggcacgtgc gtggagtggc    6000
tccgcagata cctggagaac gggaaggaga cgctgcagcg cacggacgcc cccaaaacgc    6060
```

-continued

```
atatgactca ccacgctgtc tctgaccatg aagccaccct gaggtgctgg gccctgagct    6120
tctaccctgc ggagatcaca ctgacctggc agcgggatgg ggaggaccag acccaggaca    6180
cggagctcgt ggagaccagg cctgcagggg atggaacctt ccagaagtgg gcggctgtgg    6240
tggtgccttc tggacaggag cagagataca cctgccatgt gcagcatgag ggtttgccca    6300
agcccctcac cctgagatgg gagccgtctt cccagcccac catccccatc gtgggcatca    6360
ttgctggcct ggttctcttt ggagctgtga tcactggagc tgtggtcgct gctgtgatgt    6420
ggaggaggaa gagctcagat agaaaggag ggagctactc tcaggctgca agcagtgaca    6480
gtgcccaggg ctctgatgtg tctctcacag cttgtaaagt gtgagcggcc gcgactctag    6540
atcaggcgcg ccgttaccaa gcagctatgg aagcttatgg acctcagaga ggaagtaacg    6600
aggagagggt gtggtggaat gtcactagaa accaggaaaa acaaggagga gagtattaca    6660
gggaaggagg tgaagaacct cattacccaa atactcctgc tcctcataga cgtacctggg    6720
atgagagaca caaggttctt aaattgtcct cattcgctac tccctctgac atccaacgct    6780
gggctactaa ctctagattg tacgggagct ctcttcacta ctcgctgcgt cgagagtgta    6840
cgagactctc caggtttggt aagaaatatt ttatattgtt ataatgttac tatgatccat    6900
taacactctg cttatagatt gtaagggtga ttgcaatgct ttctgcataa aactttggtt    6960
ttcttgttaa tcaataaacc gacttgattc gagaacctac tcatatatta ttgtctcttt    7020
tatactttat taagtaaaag gatttgtata ttagccttgc taaggagac atctagtgat    7080 ataagtgtga actcacactta tcttaaatga tgtaactcct taggataatc aatatacaaa    7140
attccatgac aattggcgat accgtcgacc gttcagctgc attaatgaat cggccaacgc    7200
gcggggagag gcggtttgcg tattgggcgc tcttccgctt cctcgctcac tgactcgctg    7260
cgctcggtcg ttcggctgcg gcgagcggta tcagctcact caaaggcggt aatacggtta    7320
tccacagaat caggggataa cgcaggaaag aacatgtgag caaaaggcca gcaaaaggcc    7380
aggaaccgta aaaaggccgc gttgctggcg ttttttccata ggctccgccc ccctgacgag    7440
catcacaaaa atcgacgctc aagtcagagg tggcgaaacc cgacaggact ataaagatac    7500
caggcgtttc cccctggaag ctccctcgtg cgctctcctg ttccgaccct gccgcttacc    7560
ggatacctgt ccgcctttct cccttcggga agcgtggcgc tttctcaatg ctcacgctgt    7620
aggtatctca gttcggtgta ggtcgttcgc tccaagctgg gctgtgtgca cgaaccccc    7680 gttcagcccg accgctgcgc cttatccggt aactatcgtc ttgagtccaa cccggtaaga    7740
cacgacttat cgccactggc agcagccact ggtaacagga ttagcagagc gaggtatgta    7800
ggcggtgcta cagagttctt gaagtggtgg cctaactacg gctacactag aaggacagta    7860
tttggtatct gcgctctgct gaagccagtt accttcggaa aaagagttgg tagctcttga    7920
tccggcaaac aaaccaccgc tggtagcggt ggttttttg tttgcaagca gcagattacg    7980
cgcagaaaaa aaggatctca agaagatcct ttgatctttt ctacggggtc tgacgctcag    8040
tggaacgaaa actcacgtta agggattttg gtcatgagat tatcaaaaag gatcttcacc    8100
tagatccttt taaattaaaa atgaagtttt aaatcaatct aaagtatata tgagtaaact    8160
tggtctgaca gttaccaatg cttaatcagt gaggcaccta tctcagcgat ctgtctattt    8220
cgttcatcca tagttgcctg actccccgtc gtgtagataa ctacgatacg ggagggctta    8280
ccatctggcc ccagtgctgc aatgataccg cgagacccac gctcaccggc tccagattta    8340
tcagcaataa accagccagc cggaagggcc gagcgcagaa gtggtcctgc aactttatcc    8400
gcctccatcc agtctattaa ttgttgccgg gaagctagag taagtagttc gccagttaat    8460
```

```
agtttgcgca acgttgttgc cattgctaca ggcatcgtgg tgtcacgctc gtcgtttggt    8520
atggcttcat tcagctccgg ttcccaacga tcaaggcgag ttacatgatc ccccatgttg    8580
tgcaaaaaag cggttagctc cttcggtcct ccgatcgttg tcagaagtaa gttggccgca    8640
gtgttatcac tcatggttat ggcagcactg cataattctc ttactgtcat gccatccgta    8700
agatgctttt ctgtgactgg tgagtactca accaagtcat tctgagaata gtgtatgcgg    8760
cgaccgagtt gctcttgccc ggcgtcaata cgggataata ccgcgccaca tagcagaact    8820
ttaaaagtgc tcatcattgg aaaacgttct cgggggcgaa aactctcaag atcttaccg    8880 ctgttgagat ccagttcgat gtaacccact cgtgcaccca actgatcttc agcatctttt    8940
actttcacca gcgtttctgg gtgagcaaaa acaggaaggc aaaatgccgc aaaaaaggga    9000
ataagggcga cacggaaatg ttgaatactc atactcttcc ttttcaata ttattgaagc    9060 atttatcagg gttattgtct catgagcgga tacatatttg aatgtattta gaaaaataaa    9120
caaatagggg ttccgcgcac atttccccga aaagtgccac ctgacgtcta agaaaccatt    9180
attatcatga cattaaccta taaaaatagg cgtatcacga ggccctttcg tc            9232
```

<210> SEQ ID NO 16
<211> LENGTH: 480
<212> TYPE: PRT
<213> ORGANISM: Artificial Sequence
<220> FEATURE:
<223> OTHER INFORMATION: HLA-bBA0201 (human B2M-HLA-A0201 fusion peptide)

<400> SEQUENCE: 16

```
Met Ser Arg Ser Val Ala Leu Ala Val Leu Ala Leu Leu Ser Leu Ser
1               5                   10                  15

Gly Leu Glu Ala Ile Gln Arg Thr Pro Lys Ile Gln Val Tyr Ser Arg
            20                  25                  30

His Pro Ala Glu Asn Gly Lys Ser Asn Phe Leu Asn Cys Tyr Val Ser
        35                  40                  45

Gly Phe His Pro Ser Asp Ile Glu Val Asp Leu Leu Lys Asn Gly Glu
    50                  55                  60

Arg Ile Glu Lys Val Glu His Ser Asp Leu Ser Phe Ser Lys Asp Trp
65                  70                  75                  80

Ser Phe Tyr Leu Leu Tyr Tyr Thr Glu Phe Thr Pro Thr Glu Lys Asp
                85                  90                  95

Glu Tyr Ala Cys Arg Val Asn His Val Thr Leu Ser Gln Pro Lys Ile
            100                 105                 110

Val Lys Trp Asp Arg Asp Met Gly Gly Gly Ser Gly Gly Gly Gly
        115                 120                 125

Ser Gly Gly Gly Gly Ser Gly Gly Gly Gly Ser Gly Ser His Ser Met
    130                 135                 140

Arg Tyr Phe Phe Thr Ser Val Ser Arg Pro Gly Arg Gly Glu Pro Arg
145                 150                 155                 160

Phe Ile Ala Val Gly Tyr Val Asp Asp Thr Gln Phe Val Arg Phe Asp
                165                 170                 175

Ser Asp Ala Ala Ser Gln Arg Met Glu Pro Arg Ala Pro Trp Ile Glu
            180                 185                 190

Gln Glu Gly Pro Glu Tyr Trp Asp Gly Glu Thr Arg Lys Val Lys Ala
        195                 200                 205

His Ser Gln Thr His Arg Val Asp Leu Gly Thr Leu Arg Gly Tyr Tyr
    210                 215                 220
```

| Asn | Gln | Ser | Glu | Ala | Gly | Ser | His | Thr | Val | Gln | Arg | Met | Tyr | Gly | Cys |
| 225 | | | | 230 | | | | 235 | | | | 240 | | | |

Asp Val Gly Ser Asp Trp Arg Phe Leu Arg Gly Tyr His Gln Tyr Ala
                245                 250                 255

Tyr Asp Gly Lys Asp Tyr Ile Ala Leu Lys Glu Asp Leu Arg Ser Trp
            260                 265                 270

Thr Ala Ala Asp Met Ala Ala Gln Thr Thr Lys His Lys Trp Glu Ala
        275                 280                 285

Ala His Val Ala Glu Gln Leu Arg Ala Tyr Leu Glu Gly Thr Cys Val
    290                 295                 300

Glu Trp Leu Arg Arg Tyr Leu Glu Asn Gly Lys Glu Thr Leu Gln Arg
305                 310                 315                 320

Thr Asp Ala Pro Lys Thr His Met Thr His His Ala Val Ser Asp His
                325                 330                 335

Glu Ala Thr Leu Arg Cys Trp Ala Leu Ser Phe Tyr Pro Ala Glu Ile
            340                 345                 350

Thr Leu Thr Trp Gln Arg Asp Gly Glu Asp Gln Thr Gln Asp Thr Glu
        355                 360                 365

Leu Val Glu Thr Arg Pro Ala Gly Asp Gly Thr Phe Gln Lys Trp Ala
    370                 375                 380

Ala Val Val Val Pro Ser Gly Gln Glu Gln Arg Tyr Thr Cys His Val
385                 390                 395                 400

Gln His Glu Gly Leu Pro Lys Pro Leu Thr Leu Arg Trp Glu Pro Ser
                405                 410                 415

Ser Gln Pro Thr Ile Pro Ile Val Gly Ile Ile Ala Gly Leu Val Leu
            420                 425                 430

Phe Gly Ala Val Ile Thr Gly Ala Val Val Ala Ala Val Met Trp Arg
        435                 440                 445

Arg Lys Ser Ser Asp Arg Lys Gly Gly Ser Tyr Ser Gln Ala Ala Ser
    450                 455                 460

Ser Asp Ser Ala Gln Gly Ser Asp Val Ser Leu Thr Ala Cys Lys Val
465                 470                 475                 480

<210> SEQ ID NO 17
<211> LENGTH: 9224
<212> TYPE: DNA
<213> ORGANISM: Artificial Sequence
<220> FEATURE:
<223> OTHER INFORMATION: Vector sequence for HLA-gBE

<400> SEQUENCE: 17
ctcgaggagc ttggcccatt gcatacgttg tatccatatc ataatatgta catttatatt      60
ggctcatgtc caacattacc gccatgttga cattgattat tgactagtta ttaatagtaa     120
tcaattacgg ggtcattagt tcatagccca tatatggagt tccgcgttac ataacttacg     180
gtaaatggcc cgcctggctg accgcccaac gacccccgcc cattgacgtc aataatgacg     240
tatgttccca tagtaacgcc aatagggact ttccattgac gtcaatgggt ggagtattta     300
cgctaaactg cccacttggc agtacatcaa gtgtatcata tgccaagtac gccccctatt     360
gacgtcaatg acggtaaatg gcccgcctgg cattatgccc agtacatgac cttatgggac     420
tttcctactt ggcagtacat ctacgtatta gtcatcgcta ttaccatggt gatgcggttt     480
tggcagtaca tcaatgggcg tggatagcgg tttgactcac ggggatttcc aagtctccac     540
cccattgacg tcaatgggag tttgttttgg caccaaaatc aacgggactt tccaaaatgt     600

```
cgtaacaact ccgccccatt gacgcaaatg ggcggtaggc gtgtacggtg ggaggtctat    660
ataagcagag cttctagatt gtacgggagc tcttcactac tcgctgcgtc gagagtgtac    720
gagactctcc aggtttggta agaaatattt tatattgtta taatgttact atgatccatt    780
aacactctgc ttatagattg taagggtgat tgcaatgctt tctgcataaa actttggttt    840
tcttgttaat caataaaccg acttgattcg agaacctact catatattat tgtctctttt    900
atactttatt aagtaaaagg atttgtatat tagccttgct aagggagaca tctagtgata    960
taagtgtgaa ctacacttat cttaaatgat gtaactcctt aggataatca atatacaaaa   1020
ttccatgaca attggcgccc aacgtggggc tcgaatataa gtcgggttta tttgtaaatt   1080
atccctaggg acctccgagc atagcgggag gcatataaaa gccaatagac aatggctagc   1140
aggaagtaat gttgaagaat atgaacttga tgttgaagct ctggttgtaa ttttaagaga   1200
tagaaatata ccaagaaatc ctttacatgg agaagttata ggtcttcgcc ttactgaagg   1260
atggtgggga caaattgaga gatttcagat ggtacgttga tctaaggcta tggatttggc   1320
catgggacaa gaaatattag tttatagtcc cattgtatct atgactaaaa tacaaaaaac   1380
tccactacca gaaagaaaag ctttacccat tagatggata acatggatga cttatttaga   1440
agatccaaga atccaatttc attatgataa aaccttacca gaacttaagc atattccaga   1500
tgtatataca tctagtcagt ctcctgttaa acatccttct caatatgaag gagtgtttta   1560
tactgatggc tcggccatca aaagtcctga tcctacaaaa agcaataatg ctggcatggg   1620
aatagtacat gccacataca aacctgaata tcaagttttg aatcaatggt caataccact   1680
aggtaatcat actgctcaga tggctgaaat agctgcagtt gaatttgcct gtaaaaaagc   1740
tttaaaaata cctggtcctg tattagttat aactgatagt ttctatgtag cagaaagtgc   1800
taataaagaa ttaccatact ggaaatctaa tgggtttgtt ataataaga aaaagcctct   1860 taaacatatc tccaaatgga atctattgc tgagtgttta tctatgaaac cagacattac   1920
tattcaacat gaaaaaggca tcagcctaca aataccagta ttcatactga aaggcaatgc   1980
cctagcagat aagcttgcca cccaaggaag ttatgtggtt aattgtaata ccaaaaaacc   2040
aaacctggat gcagagttgg atcaattatt acagggtcat tatataaaag gatatcccaa   2100
acaatataca tatttttag aagatggcaa agtaaaagtt tccagacctg aagggggttaa   2160 aattattccc cctcagtcag acagacaaaa aattgtgctt caagcccaca atttggctca   2220
caccggacgt gaagccactc ttttaaaaat tgccaacctt tattggtggc caaatatgag   2280
aaaggatgtg gttaaacaac taggacgctg tcaacagtgt ttaatcacaa atgcttccaa   2340
caaagcctct ggtcctattc taagaccaga taggcctcaa aaaccttttg ataaattctt   2400
tattgactat attggacctt tgccaccttc acagggatac ctatatgtat tagtagttgt   2460
tgatggaatg acaggattca cttggttata ccccactaag gctccttcta ctagcgcaac   2520
tgttaaatct ctcaatgtac tcactagtat tgcaattcca aaggtgattc actctgatca   2580
aggtgcagca ttcacttctt caacctttgc tgaatgggca aggaaagag gtatacattt   2640 ggaattcagt actccttatc acccccaaag tggtagtaag gtggaaagga aaatagtga   2700 tataaaacga cttttaacta aactgctagt aggaagaccc acaaagtggt atgacctatt   2760
gcctgttgta caacttgctt taaacaacac ctatagccct gtattaaaat atactccaca   2820
tcaactctta tttggtatag attcaaatac tccatttgca aatcaagata cacttgactt   2880
gaccagagaa gaagaacttt ctcttttaca ggaaattcgt acttcttat accatccatc   2940 cacccctcca gcctcctctc gttcctggtc tcctgttgtt ggccaattgg tccaggagag   3000
```

```
ggtggctagg cctgcttctt tgagacctcg ttggcataaa ccgtctactg tacttaaggt    3060
gttgaatcca aggactgttg ttattttgga ccatcttggc aacaacagaa ctgtaagtat    3120
agataattta aaacctactt ctcatcagaa tggcaccacc aatgacactg caacaatgga    3180
tcatttggaa aaaaatgaat aaagcgcatg aggcacttca aaatacaaca actgtgactg    3240
aacagcagaa ggaacaaatt atactggaca ttcaaaatga agaagtacaa ccaactagga    3300
gagataaatt tagatatctg ctttatactt gttgtgctac tagctcaaga gtattggcct    3360
ggatgttttt agtttgtata ttgttaatca ttgttttggt ttcatgcttt gtgactatat    3420
ccagaataca atggaataag gatattcagg tattaggacc tgtaatagac tggaatgtta    3480
ctcaaagagc tgtttatcaa cccttacaga ctagaaggat tgcacgttcc cttagaatgc    3540
agcatcctgt tccaaaatat gtggaggtaa atatgactag tattccacaa ggtgtatact    3600
atgaacccca tccggcctcg acggtatcga tggtaccggt atcgataagc ttgataacct    3660
cgagagatct aattctaccg ggtaggggag gcgcttttcc caaggcagtc tggagcatgc    3720
gctttagcag ccccgctggc acttggcgct acacaagtgg cctctggcct cgcacacatt    3780
ccacatccac cggtagcgcc aaccggctcc gttctttggt ggcccttcg cgccacttct     3840 actcctcccc tagtcaggaa gtttccccca gcaagctcgc gtcgtgcagg acgtgacaaa    3900
tggaagtagc acgtctcact agtctcgtgc agatggacag caccgctgag caatggaagc    3960
gggtaggcct ttggggcagc ggccaatagc agctttgttc cttcgctttc tgggctcaga    4020
ggctgggaag gggtgggtcc ggggcgggc tcaggggcgg gctcaggggc gggcgggcgc    4080
ccgaaggtcc tcccgaggcc cggcattctg cacgcttcaa aagcgcacgt ctgccgcgct    4140
gttctcctct tcctcatctc cgggcctttc gacctgcagc ccggggatc gatcctaggt     4200 gatttaaatc caccatgacc gagtacaagc ccacggtgcg cctcgccacc cgcgacgacg    4260
tcccccgggc cgtacgcacc ctcgccgccg cgttcgccga ctaccccgcc acgcgccaca    4320
ccgtcgaccc ggaccgccac atcgagcggg tcaccgagct gcaagaactc ttcctcacgc    4380
gcgtcgggct cgacatcggc aaggtgtggg tcgcggacga cggcgccgcg gtggcggtct    4440
ggaccacgcc ggagagcgtc gaagcggggg cggtgttcgc cgagatcggc ccgcgcatgg    4500
ccgagttgag cggttcccgg ctggccgcgc agcaacagat ggaaggcctc ctggcgccgc    4560
accgccccaa ggagcccgcg tggttcctgg ccaccgtcgg cgtctcgccc gaccaccagg    4620
gcaagggtct gggcagcgcc gtcgtgctcc ccggagtgga ggcggccgag cgcgccgggg    4680
tgcccgcctt cctggagacc tccgcgcccc gcaacctccc cttctacgag cggctcggct    4740
tcaccgtcac cgccgacgtc gagtgcccga aggaccgcgc gacctggtgc atgacccgca    4800
agcccggtgc ctgacggatc catcgctccg gtgcccgtca gtgggcagag cgcacatcgc    4860
ccacagtccc cgagaagttg gggggagggg tcggcaattg aaccggtgcc tagagaaggt    4920
ggcgcggggt aaactgggaa agtgatgtcg tgtactggct ccgccttttt cccgagggtg    4980
ggggagaacc gtatataagt gcagtagtcg ccgtgaacgt tctttttcgc aacgggtttg    5040
ccgccagaac acagctgcgg ccgcgttaac catggtggtc atggcccctc gaactctgtt    5100
cctgctgctg agtgggggctc tgaccctgac agagtccgga atccagcgga cccccaagat    5160
tcaggtgtac agcagacacc ctgcagagaa cggcaaatcc aacttcctga attgctatgt    5220
gtctgggttt catcccagtg acatcgaagt cgatctgctg aagaatggcg agagaattga    5280
aaaagtcgag cactctgacc tgagcttctc caaggattgg tccttttacc tgctgtacta    5340
```

```
taccgagttt actccaaccg aaaaagacga gtatgcctgt agggtgaacc atgtcacact    5400
gagccagccc aagatcgtga atgggaccg cgatatgggc gggggaggct caggggagg      5460 cgggagcgga ggcgggggct ccggcggggg aggatccggt tctcactcct tgaagtattt    5520
ccacacttcc gtgtcccggc ccggccgcgg ggagccccgc ttcatctctg tgggctacgt    5580
ggacgacacc cagttcgtgc gcttcgacaa cgacgccgcg agtccgagga tggtgccgcg    5640
ggcgccgtgg atggagcagg aggggtcaga gtattgggac cgggagacac ggagcgccag    5700
ggacaccgca cagattttcc gagtgaatct gcggacgctg cgcggctact acaatcagag    5760
cgaggccggg tctcacaccc tgcagtggat gcatggctgc gagctggggc ccgacgggcg    5820
cttcctccgc gggtatgaac agttcgccta cgacggcaag gattatctca ccctgaatga    5880
ggacctgcgc tcctgaccg cggtggacac ggcggctcag atctccgagc aaaagtcaaa     5940
tgatgcctct gaggcggagc accagagagc ctacctggaa gacacatgcg tggagtggct    6000
ccacaaatac ctggagaagg ggaaggagac gctgcttcac ctggagcccc aaagacaca    6060 cgtgactcac caccccatct ctgaccatga ggccaccctg aggtgctggg ccctgggctt    6120
ctaccctgcg gagatcacac tgacctggca gcaggatggg gagggccata cccaggacac    6180
ggagctcgtg gagaccaggc ctgcagggga tggaaccttc cagaagtggg cagctgtggt    6240
ggtgccttct ggagaggagc agagatacac gtgccatgtg cagcatgagg gctacccga    6300 gcccgtcacc ctgagatgga gccggcttc ccagcccacc atccccatcg tgggcatcat    6360
tgctggcctg gttctccttg gatctgtggt ctctggagct gtggttgctg ctgtgatatg    6420
gaggaagaag agctcaggtg gaaaaggagg gagctactct aaggctgagt ggagcgacag    6480
tgcccagggg tctgagtctc acagcttgta atctagagcg ccgcgactc tagatcaggc    6540 gcgccgttac caagcagcta tggaagctta tggacctcag agaggaagta acgaggagag    6600
ggtgtggtgg aatgtcacta gaaaccaggg aaaacaagga ggagagtatt acagggaagg    6660
aggtgaagaa cctcattacc caaatactcc tgctcctcat agacgtacct gggatgagag    6720
acacaaggtt cttaaattgt cctcattcgc tactccctct gacatccaac gctggactac    6780
taactctaga ttgtacggga ggctcttcac tactcgctgc gtcgagagtg tacgagactc    6840
tccaggtttg gtaagaaata tttatattg ttataatgtt actatgatcc attaacactc     6900
tgcttataga ttgtaagggt gattgcaatg ctttctgcat aaaactttgg ttttcttgtt    6960
aatcaataaa ccgacttgat tcgagaacca actcctatat tattgtctct tttatacttt    7020
attaagtaaa aggatttgta tattagcctt gctaagggag acatctagtg atataagtgt    7080
gaactacact tatcttaaat gatgtaactc cttaggataa tcaatataca aaattccatg    7140
acaattggcg ataccgtcga ccgttcagct gcattaatga atcggccaac gcgcggggag    7200
aggcggtttg cgtattgggc gctcttccgc ttcctcgctc actgactcgc tgcgctcggt    7260
cgttcggctg cggcgagcgg tatcagctca ctcaaaggcg gtaatacggt tatccacaga    7320
atcaggggat aacgcaggaa agaacatgtg agcaaaaggc cagcaaaagg ccaggaaccg    7380
taaaaaggcc gcgttgctgg cgtttttcca taggctccgc cccctgacg agcatcacaa     7440 aaatcgacgc tcaagtcaga ggtggcgaaa cccgacagga ctataaagat accaggcgtt    7500
tccccctgga agctccctcg tgcgctctcc tgttccgacc ctgccgctta ccggatacct    7560
gtccgccttt ctcccttcgg gaagcgtggc gctttctcaa tgctcacgct gtaggtatct    7620
cagttcggtg taggtcgttc gctccaagct gggctgtgtg cacgaacccc cgttcagcc    7680 cgaccgctgc gccttatccg gtaactatcg tcttgagtcc aacccggtaa gacacgactt    7740
```

```
atcgccactg gcagcagcca ctggtaacag gattagcaga gcgaggtatg taggcggtgc   7800
tacagagttc ttgaagtggt ggcctaacta cggctacact agaaggacag tatttggtat   7860
ctgcgctctg ctgaagccag ttaccttcgg aaaagagtt ggtagctctt gatccggcaa    7920
acaaaccacc gctggtagcg gtggttttt tgtttgcaag cagcagatta cgcgcagaaa    7980
aaaaggatct caagaagatc ctttgatctt ttctacgggg tctgacgctc agtggaacga   8040
aaactcacgt taagggattt tggtcatgag attatcaaaa aggatcttca cctagatcct   8100
tttaaattaa aaatgaagtt ttaaatcaat ctaaagtata tatgagtaaa cttggtctga   8160
cagttaccaa tgcttaatca gtgaggcacc tatctcagcg atctgtctat ttcgttcatc   8220
catagttgcc tgactccccg tcgtgtagat aactacgata cgggagggct accatctgg    8280 ccccagtgct gcaatgatac cgcgagaccc acgctcaccg gctccagatt tatcagcaat   8340
aaaccagcca gccggaaggg ccgagcgcag aagtggtcct gcaactttat ccgcctccat   8400
ccagtctatt aattgttgcc gggaagctag agtaagtagt tcgccagtta atagtttgcg   8460
caacgttgtt gccattgcta caggcatcgt ggtgtcacgc tcgtcgtttg gtatggcttc   8520
attcagctcc ggttcccaac gatcaaggcg agttacatga tcccccatgt tgtgcaaaaa   8580
agcggttagc tccttcggtc ctccgatcgt tgtcagaagt aagttggccg cagtgttatc   8640
actcatggtt atggcagcac tgcataattc tcttactgtc atgccatccg taagatgctt   8700
ttctgtgact ggtgagtact caaccaagtc attctgagaa tagtgtatgc ggcgaccgag   8760
ttgctcttgc ccggcgtcaa tacgggataa taccgcgcca catagcagaa ctttaaaagt   8820
gctcatcatt ggaaaacgtt cttcggggcg aaaactctca aggatcttac cgctgttgag   8880
atccagttcg atgtaaccca ctcgtgcacc caactgatct tcagcatctt ttactttcac   8940
cagcgtttct gggtgagcaa aaacaggaag gcaaaatgcc gcaaaaaagg gaataagggc   9000
gacacggaaa tgttgaatac tcatactctt ccttttcaa tattattgaa gcatttatca    9060
gggttattgt ctcatgagcg gatacatatt tgaatgtatt tagaaaaata aacaaatagg   9120
ggttccgcgc acatttcccc gaaaagtgcc acctgacgtc taagaaacca ttattatcat   9180
gacattaacc tataaaaata ggcgtatcac gaggcccttt cgtc                    9224
```

<210> SEQ ID NO 18
<211> LENGTH: 476
<212> TYPE: PRT
<213> ORGANISM: Artificial Sequence
<220> FEATURE:
<223> OTHER INFORMATION: HLA-gBE

<400> SEQUENCE: 18

Met Ala Pro Arg Thr Leu Phe Leu Leu Ser Gly Ala Leu Thr Leu
1               5                   10                  15

Thr Glu Ser Gly Ile Gln Arg Thr Pro Lys Ile Gln Val Tyr Ser Arg
            20                  25                  30

His Pro Ala Glu Asn Gly Lys Ser Asn Phe Leu Asn Cys Tyr Val Ser
        35                  40                  45

Gly Phe His Pro Ser Asp Ile Glu Val Asp Leu Leu Lys Asn Gly Glu
    50                  55                  60

Arg Ile Glu Lys Val Glu His Ser Asp Leu Ser Phe Ser Lys Asp Trp
65                  70                  75                  80

Ser Phe Tyr Leu Leu Tyr Tyr Thr Glu Phe Thr Pro Thr Glu Lys Asp
                85                  90                  95

Glu Tyr Ala Cys Arg Val Asn His Val Thr Leu Ser Gln Pro Lys Ile
                100                 105                 110

Val Lys Trp Asp Arg Asp Met Gly Gly Gly Ser Gly Gly Gly Gly
    115                 120                 125

Ser Gly Gly Gly Ser Gly Gly Gly Ser Gly Ser His Ser Leu
    130                 135                 140

Lys Tyr Phe His Thr Ser Val Ser Arg Pro Gly Arg Gly Glu Pro Arg
145                 150                 155                 160

Phe Ile Ser Val Gly Tyr Val Asp Asp Thr Gln Phe Val Arg Phe Asp
                165                 170                 175

Asn Asp Ala Ala Ser Pro Arg Met Val Pro Arg Ala Pro Trp Met Glu
                180                 185                 190

Gln Glu Gly Ser Glu Tyr Trp Asp Arg Glu Thr Arg Ser Ala Arg Asp
                195                 200                 205

Thr Ala Gln Ile Phe Arg Val Asn Leu Arg Thr Leu Arg Gly Tyr Tyr
210                 215                 220

Asn Gln Ser Glu Ala Gly Ser His Thr Leu Gln Trp Met His Gly Cys
225                 230                 235                 240

Glu Leu Gly Pro Asp Gly Arg Phe Leu Arg Gly Tyr Glu Gln Phe Ala
                245                 250                 255

Tyr Asp Gly Lys Asp Tyr Leu Thr Leu Asn Glu Asp Leu Arg Ser Trp
                260                 265                 270

Thr Ala Val Asp Thr Ala Ala Gln Ile Ser Glu Gln Lys Ser Asn Asp
                275                 280                 285

Ala Ser Glu Ala Glu His Gln Arg Ala Tyr Leu Glu Asp Thr Cys Val
290                 295                 300

Glu Trp Leu His Lys Tyr Leu Glu Lys Gly Lys Glu Thr Leu Leu His
305                 310                 315                 320

Leu Glu Pro Pro Lys Thr His Val Thr His Pro Ile Ser Asp His
                325                 330                 335

Glu Ala Thr Leu Arg Cys Trp Ala Leu Gly Phe Tyr Pro Ala Glu Ile
                340                 345                 350

Thr Leu Thr Trp Gln Gln Asp Gly Glu Gly His Thr Gln Asp Thr Glu
                355                 360                 365

Leu Val Glu Thr Arg Pro Ala Gly Asp Gly Thr Phe Gln Lys Trp Ala
                370                 375                 380

Ala Val Val Val Pro Ser Gly Glu Glu Gln Arg Tyr Thr Cys His Val
385                 390                 395                 400

Gln His Glu Gly Leu Pro Glu Pro Val Thr Leu Arg Trp Lys Pro Ala
                405                 410                 415

Ser Gln Pro Thr Ile Pro Ile Val Gly Ile Ile Ala Gly Leu Val Leu
                420                 425                 430

Leu Gly Ser Val Val Ser Gly Ala Val Val Ala Ala Val Ile Trp Arg
                435                 440                 445

Lys Lys Ser Ser Gly Gly Lys Gly Gly Ser Tyr Ser Lys Ala Glu Trp
450                 455                 460

Ser Asp Ser Ala Gln Gly Ser Glu Ser His Ser Leu
465                 470                 475

<210> SEQ ID NO 19
<211> LENGTH: 9287
<212> TYPE: DNA
<213> ORGANISM: Artificial Sequence
<220> FEATURE:
<223> OTHER INFORMATION: Vector sequence for HLA-bGBE

<400> SEQUENCE: 19

```
ctcgaggagc ttggcccatt gcatacgttg tatccatatc ataatatgta catttatatt     60
ggctcatgtc caacattacc gccatgttga cattgattat tgactagtta ttaatagtaa    120
tcaattacgg ggtcattagt tcatagccca tatatggagt tccgcgttac ataacttacg    180
gtaaatggcc cgcctggctg accgcccaac gacccccgcc cattgacgtc aataatgacg    240
tatgttccca tagtaacgcc aatagggact ttccattgac gtcaatgggt ggagtattta    300
cgctaaactg cccacttggc agtacatcaa gtgtatcata tgccaagtac gccccctatt    360
gacgtcaatg acggtaaatg gcccgcctgg cattatgccc agtacatgac cttatgggac    420
tttcctactt ggcagtacat ctacgtatta gtcatcgcta ttaccatggt gatgcggttt    480
tggcagtaca tcaatgggcg tggatagcgg tttgactcac ggggatttcc aagtctccac    540
cccattgacg tcaatgggag tttgttttgg caccaaaatc aacgggactt tccaaaatgt    600
cgtaacaact ccgccccatt gacgcaaatg ggcggtaggc gtgtacggtg ggaggtctat    660
ataagcagag cttctagatt gtacgggagc tcttcactac tcgctgcgtc gagagtgtac    720
gagactctcc aggtttggta agaaatattt tatattgtta taatgttact atgatccatt    780
aacactctgc ttatagattg taagggtgat tgcaatgctt tctgcataaa actttggttt    840
tcttgttaat caataaaccg acttgattcg agaacctact catatattat tgtctctttt    900
atactttatt aagtaaaagg atttgtatat tagccttgct aagggagaca tctagtgata    960
taagtgtgaa ctacacttat cttaaatgat gtaactcctt aggataatca atatacaaaa   1020
ttccatgaca attggcgccc aacgtggggc tcgaatataa gtcgggttta tttgtaaatt   1080
atccctaggg acctccgagc atagcgggag gcatatataa gccaatagac aatggctagc   1140
aggaagtaat gttgaagaat atgaacttga tgttgaagct ctggttgtaa ttttaagaga   1200
tagaaatata ccaagaaatc ctttacatgg agaagttata ggtcttcgcc ttactgaagg   1260
atggtgggga caaattgaga gatttcagat ggtacgttga tctaaggcta tggatttggc   1320
catgggacaa gaaatattag tttatagtcc cattgtatct atgactaaaa tacaaaaaac   1380
tccactacca gaaagaaaag ctttacccat tagatggata acatggatga cttatttaga   1440
agatccaaga atccaatttc attatgataa aaccttacca gaacttaagc atattccaga   1500
tgtatataca tctagtcagt ctcctgttaa acatccttct caatatgaag gagtgtttta   1560
tactgatggc tcggccatca aaagtcctga tcctacaaaa agcaataatg ctggcatggg   1620
aatagtacat gccacataca aacctgaata tcaagttttg aatcaatggt caataccact   1680
aggtaatcat actgctcaga tggctgaaat agctgcagtt gaatttgcct gtaaaaaagc   1740
tttaaaaata cctggtcctg tattagttat aactgatagt ttctatgtag cagaaagtgc   1800
taataaagaa ttaccatact ggaaatctaa tgggtttgtt aataataaga aaaagcctct   1860
taaacatatc tccaaatgga aatctattgc tgagtgttta tctatgaaac cagacattac   1920
tattcaacat gaaaaaggca tcagcctaca aataccagta ttcatactga aggcaatgc    1980
cctagcagat aagcttgcca cccaaggaag ttatgtggtt aattgtaata ccaaaaaacc   2040
aaacctggat gcagagttgg atcaattatt acagggtcat tatataaaag gatatcccaa   2100
acaatataca tattttttag aagatggcaa agtaaaagtt tccagacctg aagggggtaa   2160
aattattccc cctcagtcag acagacaaaa aattgtgctc caagcccaca atttggctca   2220
caccggacgt gaagccactc ttttaaaaat tgccaacctt tattggtggc caaatatgag   2280
```

```
aaaggatgtg gttaaacaac taggacgctg tcaacagtgt ttaatcacaa atgcttccaa   2340
caaagcctct ggtcctattc taagaccaga taggcctcaa aaaccttttg ataaattctt   2400
tattgactat attggacctt tgccaccttc acagggatac ctatatgtat tagtagttgt   2460
tgatggaatg acaggattca cttggttata ccccactaag gctccttcta ctagcgcaac   2520
tgttaaatct ctcaatgtac tcactagtat tgcaattcca aaggtgattc actctgatca   2580
aggtgcagca ttcacttctt caacctttgc tgaatgggca aaggaaagag gtatacattt   2640
ggaattcagt actccttatc accccaaag tggtagtaag gtggaaagga aaatagtga    2700 tataaaacga cttttaacta aactgctagt aggaagaccc acaaagtggt atgacctatt   2760
gcctgttgta caacttgctt taaacaacac ctatagccct gtattaaaat atactccaca   2820
tcaactctta tttggtatag attcaaatac tccatttgca aatcaagata cacttgactt   2880
gaccagagaa gaagaacttt ctcttttaca ggaaattcgt acttctttat accatccatc   2940 caccccctcca gcctcctctc gttcctggtc tcctgttgtt ggccaattgg tccaggagag   3000
ggtggctagg cctgcttctt tgagacctcg ttggcataaa ccgtctactg tacttaaggt   3060
gttgaatcca aggactgttg ttattttgga ccatcttggc aacaacagaa ctgtaagtat   3120
agataattta aaacctactt ctcatcagaa tggcaccacc aatgacactg caacaatgga   3180
tcatttggaa aaaatgaat aaagcgcatg aggcacttca aaatacaaca actgtgactg    3240
aacagcagaa ggaacaaatt atactggaca ttcaaaatga agaagtacaa ccaactagga   3300
gagataaatt tagatatctg ctttatactt gttgtgctac tagctcaaga gtattggcct   3360
ggatgttttt agtttgtata ttgttaatca ttgttttggt ttcatgcttt gtgactatat   3420
ccagaataca atggaataag gatattcagg tattaggacc tgtaatagac tggaatgtta   3480
ctcaaagagc tgtttatcaa cccttacaga ctagaaggat tgcacgttcc cttagaatgc   3540
agcatcctgt tccaaaatat gtggaggtaa atatgactag tattccacaa ggtgtatact   3600
atgaacccca tccggcctcg acggtatcga tggtaccggt atcgataagc ttgataacct   3660
cgagagatct aattctaccg ggtaggggag gcgcttttcc caaggcagtc tggagcatgc   3720
gctttagcag ccccgctggc acttggcgct acacaagtgg cctctggcct cgcacacatt   3780
ccacatccac cggtagcgcc aaccggctcc gttctttggt ggccccttcg cgccacttct   3840
actcctcccc tagtcaggaa gtttccccca gcaagctcgc gtcgtgcagg acgtgacaaa   3900
tggaagtagc acgtctcact agtctcgtgc agatggacag caccgctgag caatggaagc   3960
gggtaggcct ttggggcagc ggccaatagc agctttgttc cttcgctttc tgggctcaga   4020
ggctgggaag gggtgggtcc ggggggcgggc tcaggggcgg gctcaggggc gggcgggcgc   4080
ccgaaggtcc tcccgaggcc cggcattctg cacgcttcaa aagcgcacgt ctgccgcgct   4140
gttctcctct tcctcatctc cgggcctttc gacctgcagc ccgggggatc gatcctaggt   4200
gatttaaatc caccatgacc gagtacaagc ccacggtgcg cctcgccacc cgcgacgacg   4260 tccccgggc cgtacgcacc ctcgccgccg cgttcgccga ctaccccgcc acgcgccaca   4320
ccgtcgaccc ggaccgccac atcgagcggg tcaccgagct gcaagaactc ttcctcacgc   4380
gcgtcgggct cgacatcggc aaggtgtggg tcgcggacga cggcgccgcg gtggcggtct   4440
ggaccacgcc ggagagcgtc gaagcggggg cggtgttcgc cgagatcggc ccgcgcatgg   4500
ccgagttgag cggttcccgg ctggccgcgc agcaacagat ggaaggcctc ctggcgccgc   4560
accgccccaa ggagcccgcg tggttcctgg ccaccgtcgg cgtctcgccc gaccaccagg   4620
gcaagggtct gggcagcgcc gtcgtgctcc ccggagtgga ggcggccgag cgcgccgggg   4680
```

```
tgcccgcctt cctggagacc tccgcgcccc gcaacctccc cttctacgag cggctcggct    4740
tcaccgtcac cgccgacgtc gagtgcccga aggaccgcgc gacctggtgc atgacccgca    4800
agcccggtgc ctgacggatc catcgctccg gtgcccgtca gtgggcagag cgcacatcgc    4860
ccacagtccc cgagaagttg gggggagggg tcggcaattg aaccggtgcc tagagaaggt    4920
ggcgcggggt aaactgggaa agtgatgtcg tgtactggct ccgccttttt cccgagggtg    4980
ggggagaacc gtatataagt gcagtagtcg ccgtgaacgt tcttttttcgc aacgggtttg    5040
ccgccagaac acagctgcgg ccgcgttaac catgagccga tccgtggcac tggctgtcct    5100
ggctctgctg tctctgagtg gcctggaagc agtgatggcc cctagaacac tgttcctggg    5160
cggaggcggc tccggaggag agggtctgg aggcggggga agtatccagc ggactcccaa    5220
gattcaggtc tacagcagac accctgccga aaacgggaaa tccaacttcc tgaattgcta    5280
tgtgtcaggc tttcatccca gcgacatcga ggtcgatctg ctgaagaatg gcgagcggat    5340
tgaaaaagtg gagcactctg acctgtcatt cagcaaggat tggagctttt acctgctgta    5400
ctatactgag tttaccccaa cagaaaaaga cgagtatgcc tgtagggtga accatgtcac    5460
cctgagtcag cccaagatcg tgaaatggga ccgcgtatatg ggcgggggag gctccggggg    5520
aggcggctcc ggcggcgggg gaagtggcgg gggaggatcc ggttctcact ccttgaagta    5580
tttccacact tccgtgtccc ggcccggccg cggggagccc cgcttcatct ctgtgggcta    5640
cgtggacgac acccagttcg tgcgcttcga caacgacgcc gcgagtccga ggatggtgcc    5700
gcgggcgccg tggatggagc aggaggggtc agagtattgg gacccgggaga cacggagcgc    5760
cagggacacc gcacagattt tccgagtgaa tctgcggacg ctgcgcggct actacaatca    5820
gagcgaggcc gggtctcaca ccctgcagtg gatgcatggc tgcgagctgg gcccgacgg    5880
gcgcttcctc cgcgggtatg aacagttcgc ctacgacggc aaggattatc tcaccctgaa    5940
tgaggacctg cgctcctgga ccgcggtgga cacggcggct cagatctccg agcaaaagtc    6000
aaatgatgcc tctgaggcgg agcaccagag agcctacctg gaagacacat gcgtggagtg    6060
gctccacaaa tacctggaga aggggaagga gacgctgctt cacctggagc ccccaaagac    6120
acacgtgact caccacccca tctctgacca tgaggccacc ctgaggtgct gggcctggg    6180
cttctacacct gcggagatca cactgacctg gcagcaggat ggggaaggg ctacccccaga    6240
cacggagctc gtggagacca ggcctgcagg ggatggaacc ttccagaagt gggcagctgt    6300
ggtggtgcct tctggagagg agcagagata cacgtgccat gtgcagcatg aggggctacc    6360
cgagcccgtc accctgagat ggaagccggc ttcccagccc accatcccca tcgtgggcat    6420
cattgctggc ctggttctcc ttggatctgt ggtctctgga gctgtggttg ctgctgtgat    6480
atggaggaag aagagctcag gtggaaaagg agggagctac tctaaggctg agtgagcga    6540
cagtgcccag gggtctgagt ctcacagctt gtaatctaga gcggccgcga ctctagatca    6600
ggcgcgccgt taccaagcag ctatggaagc ttatggacct cagagaggaa gtaacgagga    6660
gagggtgtgg tggaatgtca ctagaaacca gggaaaacaa ggaggagagt attcagggga    6720
aggaggtgaa gaacctcatt acccaaatac tcctgctcct catagacgta cctgggatga    6780
gagacacaag gttcttaaat tgtcctcatt cgctactccc tctgacatcc aacgctggac    6840
tactaactct agattgtacg ggaggctctt cactactcgc tgcgtcgaga gtgtacgaga    6900
ctctccaggt ttggtaagaa atattttata ttgttataat gttactatga tccattaaca    6960
ctctgcttat agattgtaag ggtgattgca atgctttctg cataaaactt tggtttctt     7020
```

| | |
|---|---|
| gttaatcaat aaaccgactt gattcgagaa ccaactccta tattattgtc tcttttatac | 7080 |
| tttattaagt aaaaggattt gtatattagc cttgctaagg gagacatcta gtgatataag | 7140 |
| tgtgaactac acttatctta aatgatgtaa ctccttagga taatcaatat acaaaattcc | 7200 |
| atgacaattg gcgataccgt cgaccgttca gctgcattaa tgaatcggcc aacgcgcggg | 7260 |
| gagaggcggt ttgcgtattg ggcgctcttc cgcttcctcg ctcactgact cgctgcgctc | 7320 |
| ggtcgttcgg ctgcggcgag cggtatcagc tcactcaaag gcggtaatac ggttatccac | 7380 |
| agaatcaggg gataacgcag gaaagaacat gtgagcaaaa ggccagcaaa aggccaggaa | 7440 |
| ccgtaaaaag gccgcgttgc tggcgttttt ccataggctc cgcccccctg acgagcatca | 7500 |
| caaaaatcga cgctcaagtc agaggtggcg aaacccgaca ggactataaa gataccaggc | 7560 |
| gtttccccct ggaagctccc tcgtgcgctc tcctgttccg accctgccgc ttaccggata | 7620 |
| cctgtccgcc tttctccctt cgggaagcgt ggcgctttct caatgctcac gctgtaggta | 7680 |
| tctcagttcg gtgtaggtcg ttcgctccaa gctgggctgt gtgcacgaac cccccgttca | 7740 |
| gcccgaccgc tgcgccttat ccggtaacta tcgtcttgag tccaacccgg taagacacga | 7800 |
| cttatcgcca ctggcagcag ccactggtaa caggattagc agagcgaggt atgtaggcgg | 7860 |
| tgctacagag ttcttgaagt ggtggcctaa ctacggctac actagaagga cagtatttgg | 7920 |
| tatctgcgct ctgctgaagc cagttacctt cggaaaaaga gttggtagct cttgatccgg | 7980 |
| caaacaaacc accgctggta gcggtggttt ttttgtttgc aagcagcaga ttacgcgcag | 8040 |
| aaaaaaagga tctcaagaag atcctttgat cttttctacg gggtctgacg ctcagtggaa | 8100 |
| cgaaaactca cgttaaggga ttttggtcat gagattatca aaaaggatct tcacctagat | 8160 |
| ccttttaaat taaaaatgaa gttttaaatc aatctaaagt atatatgagt aaacttggtc | 8220 |
| tgacagttac caatgcttaa tcagtgaggc acctatctca gcgatctgtc tatttcgttc | 8280 |
| atccatagtt gcctgactcc ccgtcgtgta gataactacg atacgggagg gcttaccatc | 8340 |
| tggccccagt gctgcaatga taccgcgaga cccacgctca ccggctccag atttatcagc | 8400 |
| aataaaccag ccagccggaa gggccgagcg cagaagtggt cctgcaactt tatccgcctc | 8460 |
| catccagtct attaattgtt gccgggaagc tagagtaagt agttcgccag ttaatagttt | 8520 |
| gcgcaacgtt gttgccattg ctacaggcat cgtggtgtca cgctcgtcgt ttggtatggc | 8580 |
| ttcattcagc tccggttccc aacgatcaag gcgagttaca tgatccccca tgttgtgcaa | 8640 |
| aaaagcggtt agctccttcg gtcctccgat cgttgtcaga agtaagttgg ccgcagtgtt | 8700 |
| atcactcatg gttatggcag cactgcataa ttctcttact gtcatgccat ccgtaagatg | 8760 |
| cttttctgtg actggtgagt actcaaccaa gtcattctga atagtgta tgcggcgacc | 8820 |
| gagttgctct tgcccggcgt caatacggga taataccgcg ccacatagca gaactttaaa | 8880 |
| agtgctcatc attggaaaac gttcttcggg gcgaaaactc tcaaggatct taccgctgtt | 8940 |
| gagatccagt tcgatgtaac ccactcgtgc acccaactga tcttcagcat cttttacttt | 9000 |
| caccagcgtt tctgggtgag caaaaacagg aaggcaaaat gccgcaaaaa agggaataag | 9060 |
| ggcgacacgg aaatgttgaa tactcatact cttcctttt caatattatt gaagcattta | 9120 |
| tcagggttat tgtctcatga gcggatacat atttgaatgt atttagaaaa ataaacaaat | 9180 |
| aggggttccg cgcacatttc cccgaaaagt gccacctgac gtctaagaaa ccattattat | 9240 |
| catgacatta acctataaaa ataggcgtat cacgaggccc tttcgtc | 9287 |

<210> SEQ ID NO 20
<211> LENGTH: 500

<212> TYPE: PRT
<213> ORGANISM: Artificial Sequence
<220> FEATURE:
<223> OTHER INFORMATION: HLA-bGBE

<400> SEQUENCE: 20

```
Met Ser Arg Ser Val Ala Leu Ala Val Leu Ala Leu Leu Ser Leu Ser
1               5                   10                  15

Gly Leu Glu Ala Val Met Ala Pro Arg Thr Leu Phe Leu Gly Gly Gly
            20                  25                  30

Gly Ser Gly Gly Gly Ser Gly Gly Gly Ser Ile Gln Arg Thr
        35                  40                  45

Pro Lys Ile Gln Val Tyr Ser Arg His Pro Ala Glu Asn Gly Lys Ser
    50                  55                  60

Asn Phe Leu Asn Cys Tyr Val Ser Gly Phe His Pro Ser Asp Ile Glu
65                  70                  75                  80

Val Asp Leu Leu Lys Asn Gly Glu Arg Ile Glu Lys Val Glu His Ser
                85                  90                  95

Asp Leu Ser Phe Ser Lys Asp Trp Ser Phe Tyr Leu Leu Tyr Tyr Thr
            100                 105                 110

Glu Phe Thr Pro Thr Glu Lys Asp Glu Tyr Ala Cys Arg Val Asn His
        115                 120                 125

Val Thr Leu Ser Gln Pro Lys Ile Val Lys Trp Asp Arg Asp Met Gly
130                 135                 140

Gly Gly Gly Ser Gly Gly Gly Gly Ser Gly Gly Gly Ser Gly Gly
145                 150                 155                 160

Gly Gly Ser Gly Ser His Ser Leu Lys Tyr Phe His Thr Ser Val Ser
            165                 170                 175

Arg Pro Gly Arg Gly Glu Pro Arg Phe Ile Ser Val Gly Tyr Val Asp
        180                 185                 190

Asp Thr Gln Phe Val Arg Phe Asp Asn Asp Ala Ala Ser Pro Arg Met
    195                 200                 205

Val Pro Arg Ala Pro Trp Met Glu Gln Glu Gly Ser Glu Tyr Trp Asp
    210                 215                 220

Arg Glu Thr Arg Ser Ala Arg Asp Thr Ala Gln Ile Phe Arg Val Asn
225                 230                 235                 240

Leu Arg Thr Leu Arg Gly Tyr Tyr Asn Gln Ser Glu Ala Gly Ser His
            245                 250                 255

Thr Leu Gln Trp Met His Gly Cys Glu Leu Gly Pro Asp Gly Arg Phe
        260                 265                 270

Leu Arg Gly Tyr Glu Gln Phe Ala Tyr Asp Gly Lys Asp Tyr Leu Thr
    275                 280                 285

Leu Asn Glu Asp Leu Arg Ser Trp Thr Ala Val Asp Thr Ala Ala Gln
    290                 295                 300

Ile Ser Glu Gln Lys Ser Asn Asp Ala Ser Glu Ala Glu His Gln Arg
305                 310                 315                 320

Ala Tyr Leu Glu Asp Thr Cys Val Glu Trp Leu His Lys Tyr Leu Glu
            325                 330                 335

Lys Gly Lys Glu Thr Leu Leu His Leu Glu Pro Pro Lys Thr His Val
        340                 345                 350

Thr His His Pro Ile Ser Asp His Glu Ala Thr Leu Arg Cys Trp Ala
    355                 360                 365

Leu Gly Phe Tyr Pro Ala Glu Ile Thr Leu Thr Trp Gln Gln Asp Gly
    370                 375                 380
```

```
Glu Gly His Thr Gln Asp Thr Glu Leu Val Glu Thr Arg Pro Ala Gly
385                 390                 395                 400

Asp Gly Thr Phe Gln Lys Trp Ala Ala Val Val Pro Ser Gly Glu
            405                 410                 415

Glu Gln Arg Tyr Thr Cys His Val Gln His Glu Gly Leu Pro Glu Pro
                420                 425                 430

Val Thr Leu Arg Trp Lys Pro Ala Ser Gln Pro Thr Ile Pro Ile Val
            435                 440                 445

Gly Ile Ile Ala Gly Leu Val Leu Leu Gly Ser Val Val Ser Gly Ala
        450                 455                 460

Val Val Ala Ala Val Ile Trp Arg Lys Lys Ser Ser Gly Gly Lys Gly
465                 470                 475                 480

Gly Ser Tyr Ser Lys Ala Glu Trp Ser Asp Ser Ala Gln Gly Ser Glu
                485                 490                 495

Ser His Ser Leu
            500

<210> SEQ ID NO 21
<211> LENGTH: 7159
<212> TYPE: DNA
<213> ORGANISM: Artificial Sequence
<220> FEATURE:
<223> OTHER INFORMATION: Vector sequence for pA2-B2METKNpA

<400> SEQUENCE: 21
```

| | | |
|---|---|---|
| ctgcgcgctc gctcgctcac tgaggccgcc cgggcaaagc ccgggcgtcg ggcgaccttt | 60 |
| ggtcgcccgg cctcagtgag cgagcgagcg cgcagagagg gagtggccaa ctccatcact | 120 |
| aggggttcct gcggccgcga tgcagtccaa actctcacta aaattgccga gccctttgtc | 180 |
| ttccagtgtc taaatattta atgtcaatgg aatcaggcca gagtttgaat tctagtctct | 240 |
| tagcctttgt ttcccctgtc cataaaatga atggggtaa ttctttcctc ctacagttta | 300 |
| tttatatatt cactaattca ttcattcatc catccattcg ttcattcggt ttactgagta | 360 |
| cctactatgt gccagcccct gttctagggt ggaaactaag agaatgatgt acctagaggg | 420 |
| cgctggaagc tctaaagccc tagcagttac tgcttttact attagtggtc gttttttct | 480 |
| ccccccgcc ccccgacaaa tcaacagaac aaagaaaatt acctaaacag caaggacata | 540 |
| gggaggaact tcttggcaca gaactttcca acacttttt cctgaaggga tacaagaagc | 600 |
| aagaaaggta ctcttcact aggaccttct ctgagctgtc ctcaggatgc ttttgggact | 660 |
| atttttctta cccagagaat ggagaaaccc tgcaggaat tcccaagctg tagttataaa | 720 |
| cagaagttct ccttctgcta ggtagcattc aaagatctta atcttctggg tttccgtttt | 780 |
| ctcgaatgaa aaatgcaggt ccgagcagtt aactggctgg ggcaccatta gcaagtcact | 840 |
| tagcatctct ggggccagtc tgcaaagcga gggggcagcc ttaatgtgcc tccagcctga | 900 |
| agtcctagaa tgagcgcccg gtgtcccaag ctggggcgcg caccccagat cggagggcgc | 960 |
| cgatgtacag acagcaaact cacccagtct agtgcatgcc ttcttaaaca tcacgagact | 1020 |
| ctaagaaaag gaaactgaaa acgggaaagt ccctctctct aacctggcac tgcgtcgctg | 1080 |
| gcttggagac aggtgacggt ccctgcgggc cttgtcctga ttggctgggc acgcgtttaa | 1140 |
| tataagtgga ggcgtcgcgc tggcgggcat tcctgaagct gacagcattc gggccgagat | 1200 |
| ctagataact tcgtataatg tatgctatac gaagttatgg atccatcgat tctgcgatcg | 1260 |
| ctccggtgcc cgtcagtggg cagagcgcac atcgcccaca gtcccgaga agttgggggg | 1320 |
| aggggtcggc aattgaaccg gtgcctagag aaggtggcgc ggggtaaact gggaaagtga | 1380 |

```
tgtcgtgtac tggctccgcc ttttcccga gggtggggga gaaccgtata taagtgcagt    1440
agtcgccgtg aacgttcttt ttcgcaacgg gtttgccgcc agaacacagc tgaagcttcc    1500
accatgccca cgctactgcg ggtttatata cggtcccc acgggatggg gaaaaccacc     1560
accacgcaac tgctggtggc cctgggttcg cgcgacgata tcgtctacgt acccgagccg    1620
atgacttact ggcgggtgct gggggcttcc gagacaatcg cgaacatcta caccacacaa    1680
caccgcctcg accagggtga gatatcggcc ggggacgcgg cggtggtaat gacaagcgcc    1740
cagataacaa tgggcatgcc ttatgccgtg accgacgccg ttctggctcc tcatatcggg    1800
ggggaggctg ggagctcaca tgccccgccc ccggccctca ccctcatctt cgaccgccat    1860
cccatcgccg ccctcctgtg ctacccggcc gcgcggtacc ttatgggcag catgaccccc    1920
caggccgtgc tggcgttcgt ggccctcatc ccgccgacct gcccggcac caacatcgtg    1980
cttggggccc ttccggagga cagacacatc gaccgcctgg ccaaacgcca gcgccccggc    2040
gagcggctgg acctggctat gctgctgcg attcgccgcg tttacgggct acttgccaat    2100
acggtgcggt atctgcagtg cggcgggtcg tggcgggagg actggggaca gctttcgggg    2160
acggccgtgc cgccccaggg tgccgagccc cagagcaacg cgggcccacg accccatatc    2220
ggggacacgt tatttaccct gtttcgggcc cccgagttgc tggcccccaa cggcgacctg    2280
tataacgtgt tgcctgggc cttggacgtc ttggccaaac gcctccgttc catgcacgtc    2340
tttatcctgg attacgacca atcgcccgcc ggctgccggg acgccctgct gcaacttacc    2400
tccgggatgg tccagaccca cgtcaccacc cccggctcca taccgacgat atgcgacctg    2460
gcgcgcacgt ttgcccggga gatgggatcg gccattgaac aagatggatt gcacgcaggt    2520
tctccggccg cttgggtgga gaggctattc ggctatgact gggcacaaca gacaatcggc    2580
tgctctgatg ccgccgtgtt ccggctgtca gcgcaggggc gcccggttct ttttgtcaag    2640
accgacctgt ccggtgccct gaatgaactg caggacgagg cagcgcgct atcgtggctg    2700
gccacgacgg gcgttccttg cgcagctgtg ctcgacgttg tcactgaagc gggaagggac    2760
tggctgctat gggcgaagt gccggggcag gatctcctgt catctcacct tgctcctgcc    2820
gagaaagtat ccatcatggc tgatgcaatg cggcggctgc atacgcttga tccggctacc    2880
tgcccattcg accaccaagc gaaacatcgc atcgagcgag cacgtactcg gatggaagcc    2940
ggtcttgtcg atcaggatga tctggacgaa gagcatcagg ggctcgcgcc agccgaactg    3000
ttcgccaggc tcaaggcgcg catgcccgac ggcgaggatc tcgtcgtgac ccatggcgat    3060
gcctgcttgc cgaatatcat ggtggaaaat ggccgctttt ctggattcat cgactgtggc    3120
cggctgggtg tggcggaccg ctatcaggac atagcgttgg ctacccgtga tattgctgaa    3180
gagcttggcg gcgaatgggc tgaccgcttc ctcgtgcttt acggtatcgc cgctcccgat    3240
tcgcagcgca tcgccttcta tcgccttctt gacgagttct tctgagggtc tctagcataa    3300
cttcgtataa tgtatgctat acgaagttat aataaaagat ccttattttc attggatctg    3360
tgtgttggtt ttttgtgtgg gatccgtcga taccgtcgac tgtctcgctc cgtggcctta    3420
gctgtgctcg cgctactctc tctttctggc ctggaggcta tccagcgtga gtctctccta    3480
ccctcccgct ctggtccttc ctctcccgct ctgcaccctc tgtggccctc gctgtgctct    3540
ctcgctccgt gacttccctt ctccaagttc tccttggtgg cccgccgtgg ggctagtcca    3600
gggctggatc tcggggaagc ggcggggtgg cctgggagtg gggaaggggg tgcgcacccg    3660
ggacgcgcgc tacttgcccc tttcggcggg gagcagggga gacctttggc ctacggcgac    3720
```

```
gggagggtcg ggacaaagtt tagggcgtcg ataagcgtca gagcgccgag gttggggag      3780 ggtttctctt ccgctctttc gcggggcctc tggctccccc agcgcagctg gagtggggga      3840
cgggtaggct cgtcccaaag gcgcggcgct gaggtttgtg aacgcgtgga ggggcgcttg      3900
gggtctgggg gaggcgtcgc ccgggtaagc ctgtctgctg cggctctgct tcccttagac      3960
tggagagctg tggacttcgt ctaggcgccc gctaagttcg catgtcctag cacctctggg      4020
tctatgtggg gccacaccgt ggggaggaaa cagcacgcga cgtttgtaga atgcttggct      4080
gtgatacaaa gcggtttcga ataattaact tatttgttcc catcacatgt cacttttaaa      4140
aaattataag aactacccgt tattgacatc tttctgtgtg ccaaggactt tatgtgcttt      4200
gcgtcattta attttgaaaa cagttatctt ccgccataga taactactat ggttatcttc      4260
tgcctctcac agatgaagaa actaaggcac cgagatttta agaaacttaa ttacacaggg      4320
gataaatggc agcaatcgag attgaagtca agcctaacca gggcttttgc gggagcgcat      4380
gccttttggc tgtaattcgt gcgcggccgc aggaacccct agtgatggag ttggccactc      4440
cctctctgcg cgctcgctcg ctcactgagg ccgggcgacc aaaggtcgcc cgacgcccgg      4500
gctttgcccg gcggcctca gtgagcgagc gagcgcgcag ctgcctgcag gggcgcctga      4560
tgcggtattt tctccttacg catctgtgcg gtatttcaca ccgcatacgt caaagcaacc      4620
atagtacgcg ccctgtagcg gcgcattaag cgcggcgggt gtggtggtta cgcgcagcgt      4680
gaccgctaca cttgccagcg ccctagcgcc cgctcctttc gctttcttcc cttcctttct      4740
cgccacgttc gccggctttc cccgtcaagc tctaaatcgg gggctcccctt tagggttccg      4800 atttagtgct ttacggcacc tcgacccaa aaaacttgat tgggtgatg gttcacgtag      4860 tgggccatcg ccctgataga cggttttttcg ccctttgacg ttggagtcca cgttctttaa      4920
tagtggactc ttgttccaaa ctggacaac actcaaccct atctcgggct attcttttga      4980
tttataaggg attttgccga tttcggccta ttggttaaaa aatgagctga tttaacaaaa      5040
atttaacgcg aattttaaca aaatattaac gtttacaatt ttatggtgca ctctcagtac      5100
aatctgctct gatgccgcat agttaagcca gccccgacac ccgccaacac ccgctgacgc      5160
gccctgacgg gcttgtctgc tcccggcatc cgcttacaga caagctgtga ccgtctccgg      5220
gagctgcatg tgtcagaggt tttcaccgtc atcaccgaaa cgcgcgagac gaaagggcct      5280
cgtgatacgc ctatttttat aggttaatgt catgataata atggtttctt agacgtcagg      5340
tggcactttt cggggaaatg tgcgcggaac ccctatttgt ttatttttct aaatacattc      5400
aaatatgtat ccgctcatga gacaataacc ctgataaatg cttcaataat attgaaaaag      5460
gaagagtatg agtattcaac atttccgtgt cgcccttatt cccttttttg cggcattttg      5520
ccttcctgtt tttgctcacc cagaaacgct ggtgaaagta aaagatgctg aagatcagtt      5580
gggtgcacga gtgggttaca tcgaactgga tctcaacagc ggtaagatcc ttgagagttt      5640
tcgccccgaa gaacgttttc caatgatgag cacttttaaa gttctgctat gtggcgcggt      5700
attatcccgt attgacgccg ggcaagagca actcggtcgc cgcatacact attctcagaa      5760
tgacttggtt gagtactcac cagtcacaga aaagcatctt acggatggca tgacagtaag      5820
agaattatgc agtgctgcca taaccatgag tgataacact gcggccaact tacttctgac      5880
aacgatcgga ggaccgaagg agctaaccgc ttttttgcac aacatggggg atcatgtaac      5940
tcgccttgat cgttgggaac cggagctgaa tgaagccata ccaaacgacg agcgtgacac      6000
cacgatgcct gtagcaatgg caacaacgtt gcgcaaacta ttaactggcg aactacttac      6060
tctagcttcc cggcaacaat taatagactg gatggaggcg gataaagttg caggaccact      6120
```

-continued

```
tctgcgctcg gcccttccgg ctggctggtt tattgctgat aaatctggag ccggtgagcg    6180
tgggtctcgc ggtatcattg cagcactggg gccagatggt aagccctccc gtatcgtagt    6240
tatctacacg acgggagtc aggcaactat ggatgaacga aatagacaga tcgctgagat    6300
aggtgcctca ctgattaagc attggtaact gtcagaccaa gtttactcat atatacttta    6360
gattgattta aaacttcatt tttaatttaa aaggatctag gtgaagatcc ttttgataa    6420
tctcatgacc aaaatccctt aacgtgagtt ttcgttccac tgagcgtcag accccgtaga    6480
aaagatcaaa ggatcttctt gagatccttt ttttctgcgc gtaatctgct gcttgcaaac    6540
aaaaaaacca ccgctaccag cggtggtttg tttgccggat caagagctac caactctttt    6600
tccgaaggta actggcttca gcagagcgca gataccaaat actgtccttc tagtgtagcc    6660
gtagttaggc caccacttca agaactctgt agcaccgcct acatacctcg ctctgctaat    6720
cctgttacca gtggctgctg ccagtggcga taagtcgtgt cttaccgggt tggactcaag    6780
acgatagtta ccggataagg cgcagcggtc gggctgaacg gggggttcgt gcacacagcc    6840
cagcttggag cgaacgacct acaccgaact gagatacct cagcgtgagc tatgagaaag    6900
cgccacgctt cccgaaggga gaaaggcgga caggtatccg gtaagcggca gggtcggaac    6960
aggagagcgc acgagggagc ttccaggggg aaacgcctgg tatctttata gtcctgtcgg    7020
gtttcgccac ctctgacttg agcgtcgatt tttgtgatgc tcgtcagggg gcggagcct    7080
atggaaaaac gccagcaacg cggccttttt acggttcctg gccttttgct ggccttttgc    7140
tcacatgtcc tgcaggcag                                                 7159
```

<210> SEQ ID NO 22
<211> LENGTH: 7199
<212> TYPE: DNA
<213> ORGANISM: Artificial Sequence
<220> FEATURE:
<223> OTHER INFORMATION: Vector sequence for pA2-B2MEHyTKpA

<400> SEQUENCE: 22

```
cctgcaggca gctgcgcgct cgctcgctca ctgaggccgc ccgggcaaag cccgggcgtc      60
gggcgacctt tggtcgcccg gcctcagtga gcgagcgagc gcgcagagag ggagtggcca     120
actccatcac tagggtccc tgcggccgcg aaactaagag aatgatgtac ctagagggcg     180
ctggaagctc taaagcccta gcagttactg ctttttactat tagtggtcgt tttttctcc     240
cccccgcccc ccgacaaatc aacagaacaa agaaaattac ctaaacagca aggacatagg     300
gaggaacttc ttggcacaga actttccaaa cacttttttcc tgaagggata caagaagcaa     360
gaaaggtact ctttcactag gaccttctct gagctgtcct caggatgctt tgggactat     420
ttttcttacc cagagaatgg agaaaccctg cagggaattc ccaagctgta gttataaaca     480
gaagttctcc ttctgctagg tagcattcaa agatcttaat cttctgggtt tccgttttct     540
cgaatgaaaa atgcaggtcc gagcagttaa ctggctgggg caccattagc aagtcactta     600
gcatctctgg ggccagtctg caaagcgagg gggcagcctt aatgtgcctc agcctgaag     660
tcctagaatg agcgcccggt gtcccaagct gggcgcgca cccagatcg gagggcgccg     720
atgtacagac agcaaactca cccagtctag tgcatgcctt cttaaacatc acgagactct     780
aagaaaagga aactgaaaac gggaaagtcc ctctctctaa cctggcactg cgtcgctggc     840
ttggagacag gtgacggtcc ctgcgggcct tgtcctgatt ggctgggcac gcgtttaata     900
taagtggagg cgtcgcgctg gcgggcattc ctgaagctga cagcattcgg gccgagatct     960
```

-continued

```
agataacttc gtataatgta tgctatacga agttatggat ccatcgattc tgcgatcgct    1020
ccggtgcccg tcagtgggca gagcgcacat cgcccacagt ccccgagaag ttgggggag    1080
gggtcggcaa ttgaaccggt gcctagagaa ggtggcgcgg ggtaaactgg gaaagtgatg   1140
tcgtgtactg gctccgcctt tttcccgagg gtggggagaa accgtatata agtgcagtag   1200
tcgccgtgaa cgttcttttt cgcaacgggt ttgccgccag aacacagctg aagcttccac   1260
catgaaaaag cctgaactca ccgcgacgtc tgtcgagaag tttctgatcg aaaagttcga   1320
cagcgtctcc gacctgatgc agctctcgga gggcgaagaa tctcgtgctt tcagcttcga   1380
tgtaggaggg cgtggatatg tcctgcgggt aaatagctgc gccgatggtt tctacaaaga   1440
tcgttatgtt tatcggcact ttgcatcggc cgcgctcccg attccggaag tgcttgacat   1500
tgggaattc agcgagagcc tgacctattg catctcccgc cgtgcacagg gtgtcacgtt    1560
gcaagacctg cctgaaaccg aactgcccgc tgttctgcag ccggtcgcgg aggccatgga   1620
tgcgatcgct gcggccgatc ttagccagac gagcgggttc ggcccattcg gaccgcaagg   1680
aatcggtcaa tacactacat ggcgtgattt catatgcgcg attgctgatc cccatgtgta   1740
tcactggcaa actgtgatgg acgacaccgt cagtgcgtcc gtcgcgcagg ctctcgatga   1800
gctgatgctt tgggccgagg actgccccga agtccgcac ctcgtgcacg cggatttcgg    1860
ctccaacaat gtcctgacgg acaatggccg cataacagcg gtcattgact ggagcgaggc   1920
gatgttcggg gattcccaat acgaggtcgc caacatcttc ttctggaggc cgtggttggc   1980
ttgtatggag cagcagacgc gctacttcga gcggaggcat ccggagcttg caggatcgcc   2040
gcggctccgg gcgtatatgc tccgcattgg tcttgaccaa ctctatcaga gcttggttga   2100
cggcaatttc gatgatgcag cttgggcgca gggtcgatgc gacgcaatcg tccgatccgg   2160
agccgggact gtcgggcgta cacaaatcgc ccgcagaagc gcggccgtct ggaccgatgg   2220
ctgtgtagaa gtcgcgtctg cgttcgacca ggctgcgcgt tctcgcggcc atagcaaccg   2280
acgtacggcg ttgcgccctc gccggcagca agaagccacg gaagtccgcc cggagcagaa   2340
aatgcccacg ctactgcggg tttatataga cggtccccac gggatgggga aaaccaccac   2400
cacgcaactg ctggtggccc tgggttcgcg cgacgatatc gtctacgtac ccgagccgat   2460
gacttactgg cgggtgctgg gggcttccga gacaatcgcg aacatctaca ccacacaaca   2520
ccgcctcgac cagggtgaga tatcggccgg ggacgcggcg gtggtaatga caagcgccca   2580
gataacaatg ggcatgcctt atgccgtgac cgacgccgtt ctggctcctc atatcggggg   2640
ggaggctggg agctcacatg ccccgccccc ggccctcacc ctcatcttcg accgccatcc   2700
catcgccgcc ctcctgtgct accggccgc gcggtaccct atgggcagca tgaccccca    2760
ggccgtgctg gcgttcgtgg ccctcatccc gccgaccttg cccggcacca acatcgtgct   2820
tggggccctt ccggaggaca gacacatcga ccgcctggcc aaacgccagc gccccggcga   2880
gcggctggac ctggctatgc tggctgcgat tcgccgcgtt tacgggctac ttgccaatac   2940
ggtgcggtat ctgcagtgcg gcgggtcgtg gcggaggac tggggacagc tttcggggac    3000
ggccgtgccg ccccagggtg ccgagcccca gagcaacgcg ggcccacgac cccatatcgg   3060
ggacacgtta tttaccctgt ttcggggccc cgagttgctg gccccaacg gcgacctgta    3120
taacgtgttt gcctgggcct tggacgtctt ggccaaacgc ctccgttcca tgcacgtctt   3180
tatcctggat tacgaccaat cgcccgccgg ctgccgggac gccctgctgc aacttacctc   3240
cgggatggtc cagaccacg tcaccacccc cggctcccata ccgacgatat gcgacctggc   3300
gcgcacgttt gcccgggaga tgggggaggc taactgaggt ctctagcata acttcgtata   3360
```

```
atgtatgcta tacgaagtta taataaaaga tccttatttt cattggatct gtgtgttggt    3420
ttttttgtgtg ggatccgtcg ataccgtcga ctgtctcgct ccgtggcctt agctgtgctc   3480
gcgctactct ctctttctgg cctggaggct atccagcgtg agtctctcct accctcccgc   3540
tctggtcctt cctctcccgc tctgcaccct ctgtggccct cgctgtgctc tctcgctccg   3600
tgacttccct tctccaagtt ctccttggtg cccgccgtg gggctagtcc agggctggat    3660
ctcggggaag cggcggggtg gcctgggagt ggggaagggg gtgcgcaccc gggacgcgcg   3720
ctacttgccc ctttcggcgg ggagcagggg agacctttgg cctacggcga cgggagggtc   3780
gggacaaagt ttagggcgtc gataagcgtc agagcgccga ggttgggga gggtttctct    3840
tccgctcttt cgcggggcct ctggctcccc cagcgcagct ggagtggggg acgggtaggc   3900
tcgtcccaaa ggcgcggcgc tgaggtttgt gaacgcgtgg aggggcgctt ggggtctggg   3960
ggaggcgtcg cccgggtaag cctgtctgct gcggctctgc ttcccttaga ctggagagct   4020
gtggacttcg tctaggcgcc cgctaagttc gcatgtccta gcacctctgg gtctatgtgg   4080
ggccacaccg tggggaggaa acagcacgcg acgtttgtag aatgcttggc tgtgatacaa   4140
agcggtttcg aataattaac ttatttgttc ccatcacatg tcacttttaa aaaattataa   4200
gaactacccg ttattgacat cttttctgtgt gccaaggact ttatgtgctt tgcgtcattt   4260
aattttgaaa acagttatct tccgccatag ataactacta tggttatctt ctgcctctca   4320
cagatgaaga aactaaggca ccgagatttt aagaaactta attacacagg ggataaatgg   4380
cagcaatcga gattgaagtc aagcctaacc agggcttttg cgggagcgca tgcctttggg   4440
ctgtaattcg tgcgcggccg caggaacccc tagtgatgga gttggccact ccctctctgc   4500
gcgctcgctc gctcactgag gccgggcgac caaaggtcgc ccgacgcccg gctttgccc    4560
gggcggcctc agtgagcgag cgagcgcgca gctgcctgca gggcgcctg atgcggtatt    4620
ttctccttac gcatctgtgc ggtatttcac accgcatacg tcaaagcaac catagtacgc   4680
gccctgtagc ggcgcattaa gcgcggcggg tgtggtggtt acgcgcagcg tgaccgctac   4740
acttgccagc gccctagcgc ccgctccttt cgctttcttc ccttcctttc tcgccacgtt   4800
cgccggcttt ccccgtcaag ctctaaatcg ggggctccct ttagggttcc gatttagtgc   4860
tttacggcac ctcgacccca aaaaacttga tttgggtgat ggttcacgta gtgggccatc   4920
gccctgatag acgttttttc gcccttttgac gttggagtcc acgttcttta atagtggact   4980
cttgttccaa actggaacaa cactcaaccc tatctcgggc tattcttttg atttataagg   5040
gattttgccg atttcggcct attggttaaa aaatgagctg atttaacaaa aatttaacgc   5100
gaattttaac aaaatattaa cgtttacaat tttatggtgc actctcagta caatctgctc   5160
tgatgccgca tagttaagcc agccccgaca cccgccaaca cccgctgacg cgccctgacg   5220
ggcttgtctg ctcccggcat ccgcttacag acaagctgtg accgtctccg ggagctgcat   5280
gtgtcagagg ttttcaccgt catcaccgaa acgcgcgaga cgaaagggcc tcgtgatacg   5340
cctatttta taggttaatg tcatgataat aatggtttct tagacgtcag gtggcacttt    5400
tcggggaaat gtgcgcggaa cccctatttg tttattttc taaatacatt caaatatgta    5460
tccgctcatg agacaataac cctgataaat gcttcaataa tattgaaaaa ggaagagtat   5520
gagtattcaa catttccgtg tcgcccttat tcccttttt gcggcatttt gccttcctgt    5580
ttttgctcac ccagaaacgc tggtgaaagt aaaagatgct gaagatcagt tgggtgcacg   5640
agtgggttac atcgaactgg atctcaacag cggtaagatc cttgagagtt ttcgccccga   5700
```

```
agaacgtttt ccaatgatga gcacttttaa agttctgcta tgtggcgcgg tattatcccg     5760
tattgacgcc gggcaagagc aactcggtcg ccgcatacac tattctcaga atgacttggt     5820
tgagtactca ccagtcacag aaaagcatct tacggatggc atgacagtaa gagaattatg     5880
cagtgctgcc ataaccatga gtgataacac tgcggccaac ttacttctga caacgatcgg     5940
aggaccgaag gagctaaccg cttttttgca caacatgggg gatcatgtaa ctcgccttga     6000 tcgtttgggaa ccggagctga atgaagccat accaaacgac gagcgtgaca ccacgatgcc     6060
tgtagcaatg gcaacaacgt tgcgcaaact attaactggc gaactactta ctctagcttc     6120
ccggcaacaa ttaatagact ggatggaggc ggataaagtt gcaggaccac ttctgcgctc     6180
ggcccttccg gctggctggt ttattgctga taaatctgga gccggtgagc gtgggtctcg     6240
cggtatcatt gcagcactgg ggccagatgg taagccctcc cgtatcgtag ttatctacac     6300
gacggggagt caggcaacta tggatgaacg aaatagacag atcgctgaga taggtgcctc     6360
actgattaag cattggtaac tgtcagacca agtttactca tatatacttt agattgattt     6420
aaaacttcat ttttaattta aaaggatcta ggtgaagatc ctttttgata atctcatgac     6480
caaaatccct taacgtgagt tttcgttcca ctgagcgtca cccccgtag aaaagatcaa     6540 aggatcttct tgagatcctt ttttttctgcg cgtaatctgc tgcttgcaaa caaaaaaacc     6600
accgctacca gcggtggttt gtttgccgga tcaagagcta ccaactcttt ttccgaaggt     6660
aactggcttc agcagagcgc agataccaaa tactgtcctt ctagtgtagc cgtagttagg     6720
ccaccacttc aagaactctg tagcaccgcc tacatacctc gctctgctaa tcctgttacc     6780
agtggctgct gccagtggcg ataagtcgtg tcttaccggg ttggactcaa gacgatagtt     6840
accggataag gcgcagcggt cgggctgaac ggggggttcg tgcacacagc ccagcttgga     6900
gcgaacgacc tacaccgaac tgagatacct acagcgtgag ctatgagaaa gcgccacgct     6960
tcccgaaggg agaaaggcgg acaggtatcc ggtaagcggc agggtcggaa caggagagcg     7020
cacgagggag cttccagggg gaaacgcctg gtatctttat agtcctgtcg ggtttcgcca     7080
cctctgactt gagcgtcgat ttttgtgatg ctcgtcaggg gggcggagcc tatggaaaaa     7140
cgccagcaac gcggcctttt tacggttcct ggccttttgc tggccttttg ctcacatgt     7199
```

<210> SEQ ID NO 23
<211> LENGTH: 29
<212> TYPE: PRT
<213> ORGANISM: Artificial Sequence
<220> FEATURE:
<223> OTHER INFORMATION: HLA-G peptide

<400> SEQUENCE: 23

Met Ala Pro Arg Thr Leu Phe Leu Gly Gly Gly Gly Ser Gly Gly Gly
1               5                   10                  15

Gly Ser Gly Gly Gly Gly Ser Ile Gln Arg Thr Pro Lys
            20                  25

<210> SEQ ID NO 24
<211> LENGTH: 15
<212> TYPE: PRT
<213> ORGANISM: Artificial Sequence
<220> FEATURE:
<223> OTHER INFORMATION: Synthetic

<400> SEQUENCE: 24

Gly Gly Gly Gly Ser Gly Gly Gly Gly Ser Gly Gly Gly Gly Ser
1               5                   10                  15

BETA-2 MICROGLOBULIN-DEFICIENT CELLS

This application is a Continuation of U.S. patent application Ser. No. 14/111,837, filed Dec. 18, 2013, which is U.S. national phase of International Application No. PCT/US2012/034051, filed on Apr. 18, 2012, which claims priority to U.S. Provisional Application No. 61/477,474, filed Apr. 20, 2011, all of which are incorporated by reference herein in their entirety.

This invention was made with government support under Grant nos. R01 GM086497 and R01 DK055759 awarded by the National Institutes of Health. The government has certain rights in the invention.

A computer readable form of the Sequence Listing is filed with this application by electronic submission and is incorporated into this application by reference in its entirety. The Sequence Listing is contained in the file created on Jul. 19, 2022 having the file name "11-442-PCT.txt" and is 128,904 bytes in size

BACKGROUND OF THE INVENTION

Human pluripotent stem cells have the potential to treat diseases affecting almost every organ system. However, the clinical use of human pluripotent stem cells and their derivatives has a major limitation—rejection of transplanted cells by the recipient due to differences in the major histocompatibility complex.

The major histocompatibility complex (MHC) is a cell surface multi-component molecule found in all vertebrates that mediates interactions of leukocytes with other leukocytes or other cells. The MHC gene family is divided into three groups: class I, class II and class III. In humans, MHC is referred to as human leukocyte antigen (HLA). The HLA class I (HLA-I) protein is expressed on all nucleated cells and consists of an HLA class I heavy chain (or α chain) and β-2 microglobulin (B2M). HLA class I protein presents peptides on the cell surface to CD8+ cytotoxic T cells. Six HLA class I α chains have been identified to date, including three classical (HLA-A, HLA-B and HLA-C) and three non-classical (HLA-E, HLA-F and HLA-G) α chains. The specificity for peptide binding on the HLA class I molecule peptide binding cleft is determined by the α chain. Recognition by CD8+ T cells of the peptides presented by the HLA class I molecule mediates cellular immunity.

The HLA class I protein itself from an allogeneic source constitutes a foreign antigen in the context of transplantation. The recognition of non-self HLA class I protein is a major hurdle in using pluripotent cells for transplantation or replacement therapies. The first two clinical trials of human embryonic stem cells (ESCs) have been conducted that delivered ESCs to immune-privileged sites (such as spinal cord and eye) where allogeneic cells might survive. However, even these immune-privileged sites can eventually reject allogeneic cells, and most potential clinical applications do not involve immune-privileged sites. Alternatively, HLA-matched or partially matched cells from HLA-typed stem cell banks or pluripotent stem cell (iPSC) lines derived from each patient can be developed for transplantation. However, the development of individually matched cell line requires significant costs, months of cell culture, highly trained personnel, and extensive validation of the final product, all of which must be done with the approval of regulatory agencies. Furthermore, each cell line will likely behave somewhat differently in gene expression patterns, culture characteristics, differentiation potentials, and genetic variations.

Thus, although individualized stem cell preparations or HLA-diverse stem cell banks may address the current problem of transplantation, they require that multiple cell lines be characterized, differentiated into therapeutic cell products, and approved for human administration. This time-consuming, technically difficult, and expensive process is a major factor preventing stem cell-based therapies from entering clinical trials. Thus, there exists a need for a more effective and less expensive cell-based therapies that are not impeded by rejection.

SUMMARY OF THE INVENTION

In accordance with the present invention, in one aspect the invention provides an isolated primate cell comprising a genetically engineered disruption in a beta-2 microglobulin (B2M) gene. In certain particular embodiments, the cell comprises genetically engineered disruptions of all copies of the B2M gene.

In certain other embodiments, the cell further comprises one or more recombinant immunomodulatory genes. Suitable immunomodulatory genes include without limitation a gene encoding a viral protein that inhibits antigen presentation, a microRNA gene, and a gene that encodes a single chain (SC) fusion human leukocyte antigen (HLA) class I protein as described below. In certain preferred embodiments, the primate cell is a human cell.

In certain preferred embodiments, the one or more immunomodulatory genes comprise a polynucleotide capable of encoding a single chain fusion HLA class I protein. In certain particular embodiments, the single chain fusion HLA class I protein comprises at least a portion of B2M covalently linked to at least a portion of an HLA class I α chain selected from the group consisting of HLA-A, HLA-B, HLA-C, HLA-E, HLA-F and HLA-G. In certain preferred embodiments, the single chain fusion HLA class I protein comprises at least a portion of B2M and at least a portion of an HLA class I α chain selected from the group consisting of HLA-C, HLA-E and HLA-G. In certain other preferred embodiments, the single chain fusion HLA class I protein comprises at least a portion of B2M and at least a portion of an HLA class I α chain selected from the group consisting of HLA-A, HLA-E and HLA-G. In certain particular embodiments, the single chain fusion HLA class I protein comprises at least a portion of B2M and at least a portion of HLA-A0201 (e.g., SEQ ID NO:16). In certain other particular embodiments, the single chain fusion HLA class I protein comprises at least a portion of B2M and at least a portion of HLA-E (e.g., SEQ ID NOs:18 and 20).

In yet other particular embodiments, the cell has a normal karyotype. In certain other particular embodiments, the cell is a non-transformed cell. In particular, the cell can be a stem cell selected from the group consisting of a hematopoietic stem cell, an embryonic stem cell, an induced pluripotent stem cell, a liver stem cell, a neural stem cell, a pancreatic stem cell and a mesenchymal stem cell. In certain further embodiments, the cell further comprises one or more recombinant genes capable of encoding a suicide gene product. In certain particular embodiments, the suicide gene product comprises a protein selected from the group consisting of thymidine kinase and an apoptotic signaling protein.

In certain preferred embodiments, the stem cell is a pluripotent stem cell that expresses a single chain fusion HLA class I protein comprising at least a portion of B2M and at least a portion of an HLA class I α chain selected from the group consisting of HLA-A, HLA-B, HLA-C, HLA-E, HLA-F and HLA-G. In certain particular embodiments, the single chain fusion HLA class I protein comprises at least a portion of B2M and at least a portion of HLA-A0201.

In certain other particular embodiments, the stem cell is a differentiated cell. In certain embodiments, the differentiated cell is selected from the group consisting of a dendritic cell, a pancreatic islet cell, a liver cell, a muscle cell, a keratinocyte, a neuronal cell, a hematopoietic cell, a lymphocyte, a red blood cell, a platelet, a skeletal muscle cell, an ocular cell, a mesenchymal cell, a fibroblast, a lung cell, a GI tract cell, a vascular cell, en endocrine cell, an adipocyte and a cardiomyocyte. In certain preferred embodiments, the differentiated cell is a human cell expressing a single chain fusion HLA class I protein comprising at least a portion of B2M and at least a portion of an HLA class I α chain selected from the group consisting of HLA-A, HLA-B, HLA-C, HLA-E, HLA-F and HLA-G. In certain particular embodiments, the single chain fusion HLA class I protein comprises at least a portion of B2M and at least a portion of HLA-A0201.

In certain other embodiments, the cell further expresses a target peptide antigen that is presented by the single chain fusion HLA class I protein on the cell surface. In certain particular embodiments, the target peptide antigen is covalently linked to the single chain fusion HLA class I protein. In certain preferred embodiments, the target peptide antigen is derived from a protein of a pathogen or a cancer cell. Thus, in a related aspect, the invention provides a vaccine comprising the B2M–/– cells of the invention, wherein the vaccine is capable of eliciting in a primate an immune response specific for the target peptide antigen. In certain particular embodiments, the vaccine comprises a cell of the invention that is a differentiated dendritic cell. In certain other embodiments, the cell is a human cell of the invention, wherein the cell expresses a cytokine that further enhances the immune response. In certain preferred embodiments, the cytokine is IL2. In certain other preferred embodiments, the cytokine is IFN-γ. In certain embodiments, the immune response comprises a humoral immune response; while in other embodiments, the immune response comprises a cellular immune response. In a further related aspect, the invention provides a kit comprising a vaccine that comprises the isolated cells of the invention and an immune adjuvant. In certain embodiments, the cell is a human cell.

In yet another aspect, the invention provides a method of transplantation in a patient in need thereof comprising the step of administering to the patient an effective amount of the isolated cell of the invention. In certain embodiments, the patient is immune competent. In certain particular embodiments, the patient is a primate and preferably a human. In certain preferred embodiments, the patient is a human and the cell is a human cell. In further embodiments the cell is a stem cell or a differentiated cell, optionally expressing a single chain fusion HLA class I protein.

In yet a further aspect, the invention provides a method of treating a disease condition in a patient in need thereof comprising the step of administering to the patient an effective amount of the B2M–/– cells of the invention, wherein the disease condition includes without limitation an endocrine disorder, diabetes, an autoimmune disease, cancer, infection, anemia, a platelet disorder, immunodeficiency, cytopenia, myocardial infarction, heart failure, liver failure, skeletal or joint condition, a neurological condition, stroke, paralysis, blindness or another visual disorder, muscular dystrophy, osteogenesis imperfecta, pulmonary disease, skin condition, or burns. In certain embodiments, the patient is immune competent. In certain particular embodiments, the patient is a primate and preferably a human. In certain preferred embodiments, the patient is a human and the cell is a human cell. In further embodiments the cell is a stem cell or a differentiated cell, optionally expressing a single chain fusion HLA class I protein. In certain particular embodiments, the disease condition is diabetes and the cell is a differentiated pancreatic islet cell. In further embodiments the differentiated pancreatic islet cell expresses a single chain fusion HLA class I protein.

In another aspect, the invention provides a kit comprising the isolated primate cells, preferably human cells, of the invention. In certain embodiments, the kit is for use in transplantation or for use in treating a disease condition. In certain other embodiments, the kit comprises an implant comprising the isolated primate cells, preferably human cells, of the invention.

Specific embodiments of the present invention will become evident from the following more detailed description of certain preferred embodiments and the claims.

BRIEF DESCRIPTION OF THE DRAWINGS

FIG. 1A-1C: Creation of B2M–/– ESCs. FIG. 1A is an illustration of the AAV B2M targeting vectors with exons shown in large boxes. FIG. 1B presents Southern blots showing the results of gene targeting and Cre-mediated transgene excision (Cre-out). FIG. 1C presents results of flow cytometry showing a lack of HLA class I expression after gene targeting (with isotype controls).

FIG. 3A-3D: Single chain fusion HLA class I constructs. FIG. 3A shows the foamy viral vector design for expressing single chain fusion HLA class I proteins. FIG. 3B illustrates the linear protein structure of single chain fusion HLA class I proteins. Sequences for exemplary single chain fusion HLA class I proteins are provided for HLA-bGBE (SEQ ID NOs:19 and 20, DNA and protein sequences, respectively), HLA-gBE (SEQ ID NOs:17 and 18), HLA-bBA0201 (SEQ ID NOs:15 and 16), and (G4S)$_3$ (SEQ ID NO: 24). FIG. 3C presents results of flow cytometry showing single chain fusion HLA-E expression in B2M–/– ESCs (isotype controls). FIG. 3D presents results of flow cytometry showing single chain fusion HLA-A0201 expression in B2M–/– ESCs (isotype controls).

DETAILED DESCRIPTION OF THE INVENTION

Figure 2:
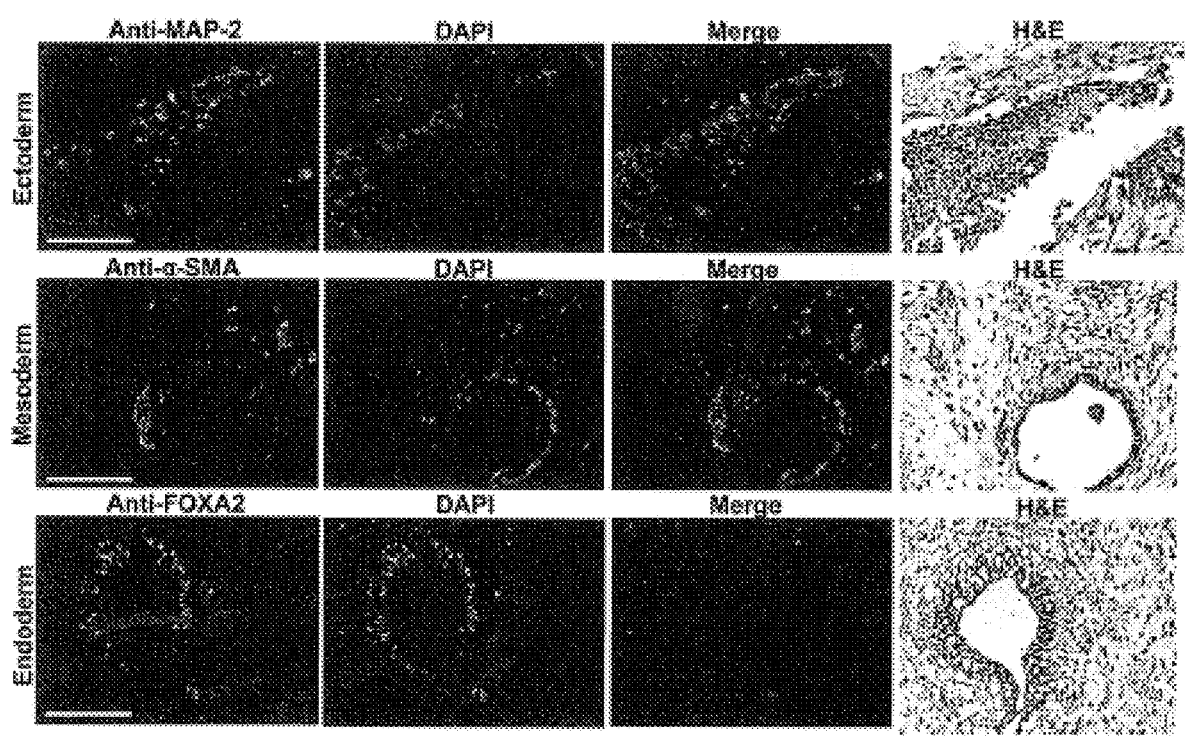
FIG. 2: Tissue sections of teratoma developed from B2M–/– Cre-out human ESCs transplanted in immune-deficient mice. The sections were stained with DAPI, hematoxylin and eosin, or lineage-specific markers MAP-2 (microtubule associated protein-2) for ectoderm, α-SAM (α-smooth muscle actin) for mesoderm or FoxA2 (forkhead box protein A2) for endoderm. Scale bar=100 microns.

All publications, patents and patent applications cited herein are hereby expressly incorporated by reference for all purposes.

Within this application, unless otherwise stated, the techniques utilized may be found in any of several well-known references such as: *Molecular Cloning: A Laboratory Manual* (Sambrook, et al., 1989, Cold Spring Harbor Laboratory Press) and *PCR Protocols: A Guide to Methods and Applications* (Innis, et al. 1990. Academic Press, San Diego, CA).

As used herein, the singular forms "a", "an" and "the" include plural referents unless the context clearly dictates otherwise. For example, reference to "an isolated cell" means one or more isolated cells.

All embodiments disclosed herein can be combined unless the context clearly dictates otherwise.

In one aspect, the invention provides B2M deficient cells. In particular, the invention provides isolated primate cells, preferably human cells, comprising a genetically engineered disruption in a B2M gene. In certain preferred embodiments, the cell is a human cell comprising a genetically engineered disruption in the B2M gene. In a related aspect, the cell comprises genetically engineered disruptions of all copies of the B2M gene. In certain embodiments, the genetic disruptions in the B2M gene result in defective or no expression of the B2M protein. Since B2M is a common component of all HLA class I proteins, the disruptions preclude the expression of all natural HLA class I proteins on the cell surface. The B2M coding sequence is shown in SEQ ID NO:1 (GenBank Accession Number NM 004048) and the B2M protein sequence is shown in SEQ ID NO:2. There may be many single nucleotide polymorphisms (SNPs) in the gene; as will be understood by those of skill in the art, the human cells and methods of the invention are applicable to any such B2M gene and SNPs.

The cells of these embodiments of the invention can be used, for example, as donor cells for transplantation in a recipient in need thereof. B2M deficient cells encompass cells that comprise a B2M−/− genetic background (referred to as B2M−/− cells). The term "B2M−/− cells" refers to primate cells, preferably human cells, that comprise genetically engineered disruptions in all copies of the B2M gene. The B2M−/− cells can serve as "universal donor cells" in that they are immunologically compatible to all or a significant percentage of recipients in a population. As used herein, a recipient or patient refers to a primate, and preferably a human. In certain particular embodiments, the cell is a human cell and the patient is a human.

The cells of the invention can be engineered to disrupt the B2M gene such that no functional endogenous B2M protein is produced from the disrupted genetic loci. In certain embodiments, the disruption results in expression of non-functional B2M proteins, including but not limited to truncations, deletions, point mutations and insertions. In other embodiments, the disruption results in no protein expression from the B2M gene.

Cells deficient in B2M expression are unable to express HLA class I proteins on the cell surface. HLA class I-deficiency provides further benefits; for example, cells without HLA class I expression cannot present auto-antigens that would otherwise prevent successful cell therapies for autoimmune diseases such as diabetes and rheumatoid arthritis. Similarly, therapeutic gene products introduced by the inventive cell therapies (e.g., dystrophin) that are missing in patients with certain genetic diseases (e.g., muscular dystrophy) will not be presented and recognized by the immune system as neo-antigens in replacement therapies.

Any suitable technique for disrupting one, two or all copies of the B2M gene can be used; exemplary techniques are disclosed throughout the application and are within the level of skill in the art based on the teachings herein and the teachings known in the art. Exemplary other techniques can be found, for example, in U.S. Patent Application Publication Number US2008/0219956, published Sep. 11, 2008, and incorporated by reference herein in its entirety. These techniques may optionally include steps to remove non-human DNA sequences from the cells after B2M gene disruption.

An exemplary embodiment of this method is as disclosed throughout the application, using an adeno-associated virus gene targeting vector, optionally including removing the transgene used for targeting via techniques such as those described below, or by removing the transgene used for targeting by Cre-mediated loxP recombination, or other suitable recombination techniques. See Khan et al. 2011, Protocol, 6:482-501, which is incorporated by reference in its entirety. Exemplary targeting vectors and exemplary vector diagrams are also disclosed herein. It is within the level of those of skill in the art, based on the teachings herein and known in the art, to utilize a variety of techniques for making the B2M−/− cells, preferably human cells, of the invention.

In certain embodiments, the cell genome of the B2M−/− cells may comprise no more than 100, no more than 50 or no more than 30 nucleotides of non-human DNA sequences. In certain other embodiments, the cell genome may comprise 6, 5, 4, 3, 2, 1, or 0 nucleotides of non-human DNA sequences. An exemplary technique for removing any non-human DNA introduced in disrupting the B2M gene is provided in FIG. 1A. The non-human DNA sequences can be removed by a second round of targeting to delete the HyTK or TKNeo transgenes in the first vectors or by the Cre-mediated loxP recombination.

In other embodiments, the cells instead can be engineered to recombinantly express a single chain fusion HLA class I protein in a B2M−/− genetic background. Thus, the B2M−/− cells as used herein also encompass primate, preferably human, cells that express one or more single chain fusion HLA class I proteins in a B2M−/− genetic background. The B2M−/− cells recombinantly expressing a single chain fusion HLA class I protein are nevertheless deficient in normal B2M function in that the cells do not express wild type B2M protein that form a non-covalently associated heterodimer with any HLA class I α chain on the cell surface.

The term "single chain fusion HLA class I protein," "single chain fusion HLA class I molecule" or "single chain fusion HLA class I antigen" refers to a fusion protein comprising at least a portion of the B2M protein covalently linked, either directly or via a linker sequence, to at least a portion of an HLA-I α chain. On the other hand, the term "HLA class I protein," "HLA class I molecule" or "HLA class I antigen" refers to a non-covalently associated heterodimer of B2M and an HLA α chain expressed on the surface of a wild type cell.

As used herein, the term "HLA class I α chain" or "HLA-I heavy chain" refers to the α chain of the HLA class I heterodimer. HLA class I heavy chain includes without limitation HLA class I α chains HLA-A, HLA-B, HLA-C, HLA-E, HLA-F, and HLA-G. Representative DNA and protein sequences are provided for HLA-A (GenBank No. K02883.1, SEQ ID NO:3; UniProt No. P01892, SEQ ID NO:4), HLA-B (NM_005514, SEQ ID NO:5; NP_005505; SEQ ID NO:6), HLA-C(NM_002117, SEQ ID NO:7; NP_002108, SEQ ID NO:8), HLA-E (NM_005516, SEQ ID NO:9; NP_005507, SEQ ID NO:10), HLA-F (NM_018950, SEQ ID NO:11; NP_061823, SEQ ID NO:12), and HLA-G (NM_002127, SEQ ID NO:13; NP_002118, SEQ ID NO:14).

In addition, although the term "HLA class I protein/molecule" is known to refer to the MEW class I protein/ molecule in human, the terms HLA and MEW are sometimes used interchangeably throughout this application: for example, the term HLA class I protein can also be used to refer to the primate equivalent to the HLA class I protein in a primate. One of skill in the art will be able to discern the meaning of the term based on the content.

The term B2M−/− cells as used herein also encompasses cells having genetically engineered disruptions in all copies of the B2M gene, wherein one B2M allele is genetically engineered to express, instead of the wild type B2M protein, a single chain fusion HLA class I protein (i.e., genetically targeted knockin in one B2M allele). B2M−/− cells with such genetic background express B2M only in the context of the single chain fusion HLA class I protein from a B2M genetic locus. In certain advantageous embodiments, the expression of the single chain fusion HLA class I protein is regulated by the endogenous B2M regulatory sequence located at the B2M locus.

In related embodiments, B2M−/− cells further encompass cells having genetically engineered disruptions in all copies of the B2M gene, wherein all B2M alleles are genetically engineered to express, instead of the wild type B2M protein, single chain fusion HLA class I proteins (i.e., genetically targeted knockin in all B2M alleles). B2M−/− cells with such genetic disruptions express B2M only in the context of single chain fusion HLA class I proteins from the genetic loci of all the alleles of the B2M gene. In certain embodiments, the cells are genetically engineered to express the same type of single chain fusion HLA class I protein from the genetic loci of all alleles of the B2M gene; while in other embodiments, the cells are genetically engineered to express different types of single chain fusion HLA class I proteins from different genetic loci of different alleles of the B2M gene.

Throughout the application, the "cells of the invention," "isolated cells of the invention," "B2M−/− cells," "B2M−/− cells of the invention" or "stem cells or differentiated cells of the invention" sometimes can be used interchangeably to encompass all the B2M−/− cells described herein. In certain particular embodiments, the B2M−/− cells of the invention express a single chain fusion HLA class I protein as defined herein, in a B2M−/− background. The B2M−/− cells can be genetically engineered to express a single chain HLA class I protein either from the B2M locus or from other location of the genome. In certain particular embodiments, the cells of the invention comprise genetically engineered disruptions in all alleles of the B2M gene that preclude the expression of wild type B2M protein, and nevertheless express a single chain fusion HLA class I protein from a B2M genetic locus. In certain other particular embodiments, the cells of the invention comprise genetically engineered disruptions in all alleles of the B2M gene that preclude the expression of wild type B2M protein, and nevertheless express single chain fusion HLA class I proteins from all B2M genetic loci. The term "gene," "allele," and "genetic locus" may be used interchangeably throughout the application.

The "isolated cell" can be any suitable cell type for a given purpose. For example, the cell can be a pluripotent stem cell or a differentiated cell. "A stem cell" broadly encompasses any cells that are capable of further differentiation. "A pluripotent stem cell" refers to a stem cell that has the potential to differentiate into any of the three germ layers: endoderm, mesoderm or ectoderm. "An adult stem cell," on the other hand, is multipotent in that it can produce only a limited number of cell types. "An embryonic stem (ES) cell" refers to a pluripotent stem cell derived from the inner cell mass of the blastocyst, an early-stage embryo. "Induced pluripotent stem cells (iPS cells)" are pluripotent stem cell artificially derived from a non-pluripotent cell, typically an adult somatic cell, by artificially inducing expression of certain genes.

In certain embodiments, the single chain fusion HLA class I protein comprises at least a portion of B2M and at least a portion of HLA-A, HLA-B, HLA-C, HLA-E, HLA-F or HLA-G (also referred to as a dimeric construct). In certain preferred embodiments, the HLA α chain contained in the single chain fusion HLA class I protein does not contain the leader sequence (or signal sequence) of the HLA class I α chain (leaderless HLA α chain). In certain other embodiments, the single chain fusion HLA class I protein comprises at least a portion of B2M and at least a portion of HLA-C, HLA-E or HLA-G. In certain further embodiments, the single chain fusion HLA class I protein comprises at least a portion of B2M and at least a portion of HLA-A, HLA-E or HLA-G. In certain preferred embodiments, the single chain fusion HLA class I protein comprises a leader sequence (or signal peptide) covalently linked to the at least a portion of B2M and at least a portion of an HLA α chain to ensure proper folding of the single chain fusion on the cell surface. The leader sequence can be the leader sequence of the B2M protein, the leader sequence of an HLA α chain protein or the leader sequence of other secretary proteins. In certain particular embodiments, the single chain fusion HLA class I protein comprises a B2M protein with its leader sequence removed. In certain other particular embodiments, the single chain fusion HLA class I protein comprises an HLA α chain protein with its leader sequence removed. Certain HLA class I α chains are highly polymorphic. As will be understood by those of skill in the art, the human cells and methods of the invention are applicable to any such HLA α chains and polymorphism thereof.

Single chain fusion HLA class I proteins comprising sequence variants and fragments of B2M and/or HLA α chains are contemplated by the instant invention, wherein such single chain fusion constructs nevertheless possess normal HLA class I functions, e.g., forming proper secondary structure of the heterodimer on the cell surface, presenting peptides in the peptide binding cleft and engaging the inhibitory receptors on the surface of NK cells. In certain embodiments, the variants share at least 75%, 80%, 81%, 85%, 88%, 90%, 91%, 92%, 93%, 94%, 95%, 96%, 97%, 98%, 99%, or complete sequence homology with the naturally occurring HLA heavy chains and B2M sequences, wherein the variants possess normal HLA class I functions. In certain other embodiments, the variants share at least 75%, 80%, 81%, 85%, 88%, 90%, 91%, 92%, 93%, 94%, 95%, 96%, 97%, 98%, 99%, or complete sequence homology with the sequences of B2M or HLA heavy chains as shown in SEQ ID NOs:2, 4, 6, 8, 10, 12 or 14.

In certain particular embodiments, the HLA-A variants share at least 85%, 88,%, 90%, 91%, 92%, 93%, 94%, 95%, 96%, 97%, 98%, 99%, or complete sequence homology with SEQ ID NO:4. In certain other particular embodiments, the HLA-B variants share at least 81%, 83%, 85%, 88,%, 90%, 91%, 92%, 93%, 94%, 95%, 96%, 97%, 98%, 99%, or complete sequence homology with SEQ ID NO:6. In certain further embodiments, the HLA-C variants share at least 90%, 91%, 92%, 93%, 94%, 95%, 96%, 97%, 98%, 99%, or complete sequence homology with SEQ ID NO:8. In yet other embodiments, the HLA-E variants share at least 97%, 98%, 99%, or complete sequence homology with SEQ ID NO:10. In certain particular embodiments, the HLA-F variants share at least 99%, or complete sequence homology with SEQ ID NO:12. In certain other embodiments, the HLA-G variants share at least 98%, 99%, or complete sequence homology with SEQ ID NO:14.

In certain other embodiments, the single chain fusion HLA class I protein comprises a full length B2M (including its leader sequence) and an HLA α chain without the leader sequence (leaderless HLA α chain); while in certain other embodiments, the single chain fusion HLA class I protein comprises a B2M protein without the leader sequence. It is understood that B2M−/− cells expressing two, three or more different types of single chain fusion HLA class I protein in any combination, for example, expressing SC fusion comprising HLA-A (or a leaderless HLA-A) and SC fusion comprising HLA-C (or a leaderless HLA-C), expressing SC fusion comprising HLA-A (or a leaderless HLA-A) and SC fusion comprising HLA-E (or a leaderless HLA-E), or expressing SC fusion comprising HLA-B (or a leaderless HLA-B), SC fusion comprising HLA-E (or a leaderless HLA-E) and SC fusion comprising HLA-G (or a leaderless HLA-G), etc., are all contemplated by the invention.

Natural killer (NK) cells are part of the innate immune response. Several pathogens can down regulate HLA class I protein expression in infected cells. The NK cells monitor infection by recognizing and inducing apoptosis in cells that do not express HLA class I proteins. The inhibitory receptors on the NK cell surface recognize HLA class I α chain alleles thereby preventing NK-medicated apoptosis in uninfected normal cells. Thus, in certain particular embodiments, the single chain fusion HLA-I protein inhibits NK cell-mediated killing of cells that do not express endogenous HLA class I proteins by binding to the inhibitory receptors on the NK cells. For example, HLA-E is a ligand for the CD94/NKG2 receptor of NK cells that inhibits NK cell-mediated apoptosis. Thus, in certain particular embodiments, the B2M−/− cell expresses the single chain fusion HLA class I protein comprising at least a portion of B2M and at least a portion of HLA-E. In addition, HLA-G is normally expressed on the surface of placental cytotrophoblasts that do not express HLA-A, B or C, and it protects these cells from NK cell-mediated lysis by interacting with the inhibitory ILT2 (LIR1) receptor on NK cells (Pazmany et al., 1996, Science 274, 792-795). Thus, in certain other preferred embodiments, the B2M−/− cell expresses the single chain fusion HLA class I protein comprising at least a portion of B2M and at least a portion of HLA-G.

In certain particular embodiments, the single chain fusion HLA class I protein comprises at least a portion of B2M and at least a portion of HLA-A0201, an allele of HLA-A. HLA-A0201 (SEQ ID NO:4) is a common HLA class I allele found in a large percentage of the population in the United States. Thus, in certain advantageous embodiments, the isolated cell expresses the single chain fusion HLA class I protein comprising at least a portion of B2M and at least a portion of HLA-A0201 in a B2M−/− genetic background, wherein the isolated cell is immune compatible with a large percentage of the human population in the United States. Other suitable common alleles that can be used include without limitation HLA-A0101, HLA-A0301, HLA-B0702, HLA-B0801, HLA-00401, HLA-00701, and HLA-00702. In certain preferred embodiments, the HLA allele comprises at least a portion of HLA-A0201 (SEQ ID NO:4), HLA-B0702 (SEQ ID NO:6) or HLA-00401 (SEQ ID NO:8).

In certain further embodiments, the single chain fusion HLA class I protein also comprises a specific peptide antigen that occupies the peptide binding cleft of the single chain fusion HLA class I protein, wherein the peptide antigen is covalently linked to the single chain fusion HLA class I protein (also referred to as a trimeric construct). An example of the trimeric construct is shown in FIG. 3B. The HLA-bGBE construct of FIG. 3B comprises B2M and HLA-E covalently linked to a peptide antigen (such as, but not limited to, the HLA-G peptide antigen as illustrated in the figure) (SEQ ID NO:23) designed to occupy the peptide binding cleft of the single chain fusion HLA class I protein. In certain other embodiments, the covalently linked peptide antigen is cleaved via a built in protease cleavage site, and the cleaved peptide antigen can bind to the peptide binding cleft of the single chain fusion HLA-I protein for presentation. In certain alternative embodiments, the peptide antigen occupying the peptide binding cleft of the single chain fusion HLA class I protein is produced by the intracellular antigen processing pathway, in which the peptide antigen is produced by proteasome, transported to and loaded onto the single chain fusion HLA class I protein in the endoplasmic reticulum. In certain particular embodiments, the peptide antigen comprises a peptide of a tumor antigen. In certain other embodiments, the peptide antigen comprises a peptide of a protein from a pathogen including without limitation a bacterium, a virus, a fungus and a parasite. In further embodiments, the peptide antigen comprises a peptide of a tumor antigen. In certain particular embodiments, the B2M−/− cell expresses a single chain fusion HLA class I protein that is covalently linked to a peptide that does not comprise an auto-antigen or neo-antigen to the patient. It is within the ability of a skilled person to design the single chain fusion HLA class I protein and the peptide antigen presented thereon to modulate the immune response that may be elicited in a recipient.

The isolated B2M−/− cell expressing a single chain fusion HLA class I protein comprising a specific peptide antigen either covalently or non-covalently bound to the single chain fusion HLA class I protein can be used, for example, for administration to a recipient to elicit an immune response. Accordingly, in a related aspect, the invention provides a vaccine comprising the isolated cell of the invention, wherein the vaccine is capable of eliciting in a recipient an immune response specific for the target peptide antigen. The immune response includes without limitation a cellular immune response and/or a humoral immune response. The vaccine may comprise a stem cell or a differentiated cell; in certain particular embodiments, the cell is a differentiated dendritic cell. In certain other embodiments, the cell further expresses a cytokine. Any suitable cytokine can be used; in certain particular embodiments, the cytokine is IL2 or IFN-γ. In certain preferred embodiments, the cell is a human cell and the recipient is a human.

The single chain fusion HLA class I protein can be expressed from an expression vector that allows either transient or more preferably, stable expression of the protein in a B2M−/− cell. Exemplary suitable expression vectors are known in the art. One such example is a retroviral vector, which is capable of integrating into the cellular genome to provide long-term, stable expression of an exogenous gene. In certain particular embodiments, the viral vector is derived from human foamy virus, a type of retrovirus. Other suitable viral vectors include without limitation vectors derived from retrovirus, adenoviral virus, adeno-associated virus, lentivirus, herpes simplex virus, vaccinia virus, and pox virus.

In certain preferred embodiments, the polynucleotide capable of encoding a single chain fusion HLA class I protein is integrated into the chromosome of the cells, preferably into the B2M or the HLA loci, for stable expression. Thus, in certain preferred embodiments, the B2M loci are disrupted by inserting in the B2M loci the polynucleotide capable of encoding a single chain fusion HLA class I protein to replace the expression of the endogenous wild type B2M protein. The result of such gene targeting disrupts normal B2M expression and precludes formation of wild type HLA class I proteins but permits expression of a predetermined single chain fusion HLA class I protein of choice on the surface of the otherwise B2M deficient cells. Other expression vectors are also contemplated and the selection of suitable expression vector is within the ability of one ordinary skill in the art.

According to the vector design, the polynucleotide capable of expressing a single chain fusion HLA class I protein is delivered to a cell by viral infection (when a viral vector is used) or by other delivery methods including without limitation transfection, electroporation, gene targeting or liposome-mediated DNA delivery.

Any immune effects of the single chain fusion HLA class I protein expressing B2M–/– cells can be studied by various means. For example, B2M–/– cells expressing a SC fusion HLA class I protein can be differentiated into antigen-presenting dendritic cells (iDCs). Suppression of NK cell-mediated lysis can be measured by chromium release assays after incubating iDCs with normal human NK cells and NKL cell lines. A variety of controls (untransduced B2M–/– iDCs, B2M+/+ iDCs, the 721.221 class I-negative cell line, and anti-receptor and anti-HLA antibodies) can be used to establish the specificity of the interactions. Additional characterization can be done with Elispot assays by incubating the cells with T cells.

In a related aspect, the invention provides an HLA class I-typed B2M–/– cell bank, wherein the cells of the cell bank comprise a B2M–/– genetic background and are engineered to express one or more types of single chain fusion HLA class I proteins in which the HLA α chain is selected from the group consisting of HLA-A, HLA-B, HLA-C, HLA-E, HLA-F and HLA-G. In certain embodiments, the cell bank comprises a population of cells that expresses a single chain fusion HLA class I protein in which the HLA α chain comprises HLA-A. In certain other embodiments, the cell bank comprises a population of cells that expresses a single chain fusion HLA class I protein in which the HLA α chain comprises HLA-B. In certain further embodiments, the cell bank comprises a population of cells that expresses a single chain fusion HLA class I protein in which the HLA α chain comprises HLA-C. In yet other embodiments, the cell bank comprises a population of cells that expresses a single chain fusion HLA class I protein in which the HLA α chain comprises HLA-E. In certain other embodiments, the cell bank comprises a population of cells that expresses a single chain fusion HLA class I protein in which the HLA α chain comprises HLA-F. In certain particular embodiments, the cell bank comprises a population of cells that expresses a single chain fusion HLA class I protein in which the HLA α chain comprises HLA-G. In certain particular embodiments, the cell bank comprises the above-described one or more or preferably all populations of cells.

The cells of the cell bank can be pluripotent stem cells or differentiated cells. In certain particular embodiments, the cell bank comprises different types of differentiated cells, such as skin cells, pancreatic beta islet cells, etc., that express the same single chain fusion HLA class I protein. While in other particular embodiments, the cell bank comprises different types of differentiated cells, such as skin cells, pancreatic beta islet cells, etc., that each express different single chain fusion HLA class I proteins. It can be determined by a skilled researcher or clinician to choose suitable donor cells from the cell bank for a given patient. In certain other embodiments, some of the cells of the cell bank express the HLA class I allele that matches the HLA class I allele of the patient to whom the cells are administered. In certain preferred embodiments, the cell is a human cell and the patient is a human. In certain particular embodiments, the cells express a single chain fusion HLA class I protein comprising B2M and HLA-A0201 that matches the HLA allele of a large portion of the population in the United States.

In another aspect, the invention provides a method of transplantation in a patient in need thereof comprising the step of administering to the patient an effective amount of the cells of the invention for transplantation. Because the B2M–/– cells do not express wild type HLA class I protein on the cell surface, the cells when administered to a patient elicit minimal or no immune responses in the patient. Thus, transplantation using the B2M–/– cells limits the need for taking immune suppressant therapies. Thus, in certain preferred embodiments, the patient is immune competent. In certain other embodiments, the cell is an isogeneic cell; while in other embodiments, the cell is an allogeneic cell.

In certain further embodiments, the cells of the invention are pluripotent stem cells; while in other embodiments, the cells of the invention are differentiated cells. In certain preferred embodiments, the cell is a human cell and the patient is a human patient. In certain particular embodiments, the method of transplantation comprises administering to a human an effective amount of the pluripotent stem cells or differentiated cells. In certain preferred embodiments, the cells of the invention further express one or more engineered single chain fusion HLA class I proteins. In certain other embodiments, the cells are able to escape NK cell-mediated killing and elicit minimal or no immune response in the recipient after transplantation.

Transplantation therapy, replacement therapy or regenerative therapy refers to therapies for a disease condition by administering to a patient cells or tissues to replenish or replace defective cellular functions in a target organ. In certain particular embodiments, the need for transplantation arises as a result of physical or pathological injuries to a tissue or organ. In certain other particular embodiments, the need for transplantation arises as a result of one or more genetic defect or mutation in the patient and the transplantation of the cells of the invention replenishes or replaces defective cellular functions in the patient without the need for gene therapy to correct the underlying genetic mutation of the patient. In certain further embodiments, the transplantation includes without limitation hematopoietic stem cell transplantation, or transplantation of cells that are incorporated into an organ such as liver, kidney, pancreas, lung, brain, muscle, heart, gastrointestinal tract, nervous system, skin, bones, bone marrow, fat, connective tissue, immune system, or blood vessels. In certain particular embodiments, the target organ is a solid organ.

In certain particular embodiments, the cells administered to the recipient may or may not be incorporated into an organ in need of such therapy. In certain embodiments, the cells of the invention are differentiated into the desired cell type, either before or after transplantation, and provide the necessary cellular function without itself being incorporated into the tissue at the site of transplantation. For example, in certain embodiments for treating diabetes, the cells of the invention either as pluripotent stem cells or differentiated pancreatic beta islet cells are transplanted to a diabetic patient. The transplanted cells need not reconstitute a functioning pancreas: they just need to secrete insulin in response to glucose levels. In certain particular embodiments, the cells are transplanted into an ectopic location and are not fully incorporated into the pancreas. Transplantation of pluripotent cells of the invention, differentiated cells of the invention, or a tissue differentiated and developed ex vivo from the cells of the invention are all contemplated by the invention. In certain preferred embodiments, the cell is a human cell and the patient is a human patient. In certain other preferred embodiments, the cells of the invention express one or more single chain fusion HLA class I proteins.

In a further aspect, the invention provides a method of treating a disease condition in a patient in need thereof comprising the step of administering to the patient an effective amount of the cell of the invention to treat the disease condition, wherein the disease condition is diabetes, an autoimmune disease, cancer, infection, anemia, cytopenia, myocardial infarction, heart failure, skeletal or joint condition, osteogenesis imperfecta or burns. In certain particular embodiments, the disease condition results from pathological or physical injuries to a tissue or organ. In certain embodiments, the cells of the invention are stem cells; while in other embodiments, the cells of the invention are differentiated cells. In certain preferred embodiments, the cell is a human cell and the patient is a human patient. In certain particular embodiments, the human cell is a differentiated cell. Transplantation of a tissue developed ex vivo from the cells of the invention is also contemplated by the invention. In certain preferred embodiments, the cells of the invention further express one or more single chain fusion HLA class I proteins. In certain embodiments, the cell is an isogeneic cell; while in other embodiments, the cell is an allogeneic cell.

In certain particular embodiments, the cell is a differentiated cell including without limitation a dendritic cell, lymphocyte, red blood cell, platelet, hematopoietic cell, pancreatic islet cell, liver cell, muscle cell, keratinocyte, cardiomyocyte, neuronal cell, skeletal muscle cell, ocular cell, mesenchymal cell, fibroblast, lung cell, GI tract cell, vascular cell, endocrine cell and adipocyte. In certain other particular embodiments, the invention provides a method of treating a disease condition in a solid organ. In certain embodiments, the cells of the invention used in treating a disease condition express one or more single chain fusion HLA class I proteins.

"Treating" a patient having a disease or disorder means accomplishing one or more of the following: (a) reducing the severity of the disease; (b) arresting the development of the disease or disorder; (c) inhibiting worsening of the disease or disorder; (d) limiting or preventing recurrence of the disease or disorder in patients that have previously had the disease or disorder; (e) causing regression of the disease or disorder; (f) improving or eliminating the symptoms of the disease or disorder; and (f) improving survival. In certain preferred embodiments, the disease or disorder is a disease or disorder that can be treated by transplantation of tissues or cells.

The effective amount of the isolated cells of the invention for transplantation or for treating a disease condition depends on a number of factors, such as the type of tissue, the severity of the disease condition, the transplantation reaction, the reason for transplantation, and the age and general health of the patient. The effective amount can be determined by a skilled researcher or clinician by routine practice. Due to the reduced immunogenicity of the transplanted cells, relative large amount of cells can be tolerated by a patient to achieve the desired therapeutic effects. Alternatively, the cells can be repeatedly transplanted at intervals until a desired therapeutic effect is achieved.

The route for administration of the cells of the invention is not limited in any particular way. Exemplary delivery routes include without limitation intravenous, intramuscular, subdermal, intraperitoneal, transcutaneous, intracutaneous, and subcutaneous route. The cells of the present invention can also be administered topically by injection. For example, the cells can be injected into an injured joint, a fractured bone, an infarct site, an ischemic site or their periphery.

In certain particular embodiments, the cells are administered via a delivery device including without limitation a syringe. For example, the cells can be suspended in a solution or a pharmaceutical composition contained in such a delivery device. The "solution" or "pharmaceutical composition" comprises a physiological compatible buffer and optionally a pharmaceutically acceptable carrier or diluent in which the cells of the invention remain viable. The use of such carriers and diluents is well known in the art. The solution includes without limitation physiologically compatible buffers such as Hank's solution, Ringer' solution, or physiologically buffered saline. The cells can be kept in the solution or pharmaceutical composition for short term storage without losing viability. In certain particular embodiments, the cells are frozen for long term storage without losing viability according to cryopreservation methods well-known in the art.

Aqueous injection suspensions may contain substances which increase the viscosity of the suspension, such as sodium carboxymethyl cellulose, sorbitol, or dextran, but still fluid to the extent that can be easily delivered by syringe injection. The solution is preferably sterile, stable under the conditions of manufacture and storage and is free of microorganism contamination through the use of, for example, parabens, chlorobutanol, phenol, ascorbic acid, thimerosal, and the like. The cells contained in the solution can be stem cells or differentiated cells as described herein, in a pharmaceutically acceptable carrier or diluent and, as required, other ingredients indicated above.

The cells may be administered systemically (e.g., intravenously) or locally (e.g., directly into a myocardial defect under the guidance of echocardiogram, or by direct application to damaged tissues or organs accessible during open surgery). For injections, the cells may be in an injectable liquid suspension preparation or in a biocompatible medium which is injectable in liquid form and becomes semi-solid at the site of damaged tissue. A syringe, a controllable endoscopic delivery device or other similar devises can be used so long as the needle lumen is of sufficient diameter (e.g. at least 30 gauge or larger) to avoid physical damages to the cells during delivery.

In certain other embodiments, the cells can be transplanted via a solid support, e.g., a planar surface or three-dimensional matrix. The matrix or planar surface is surgically implanted into the appropriate site in a patient. For example, a patient needing a pancreatic graft can have differentiated cells on a solid support surgically implanted in the pancreas tissue. Exemplary solid support includes without limitation a patch, a gel matrix (such as GELFOAM® from Pharmacia-Upjohn), polyvinyl alcohol sponge (PVA)-collagen gel implants (such as IVALON, Unipoint Industries, High Point, NC) and other similar or equivalent devices. A variety of other encapsulation technologies can be used with the cells of the invention, for example, WO 91/10470; WO 91/10425; U.S. Pat. Nos. 5,837,234; 5,011,472; 4,892,538).

Figure 4:
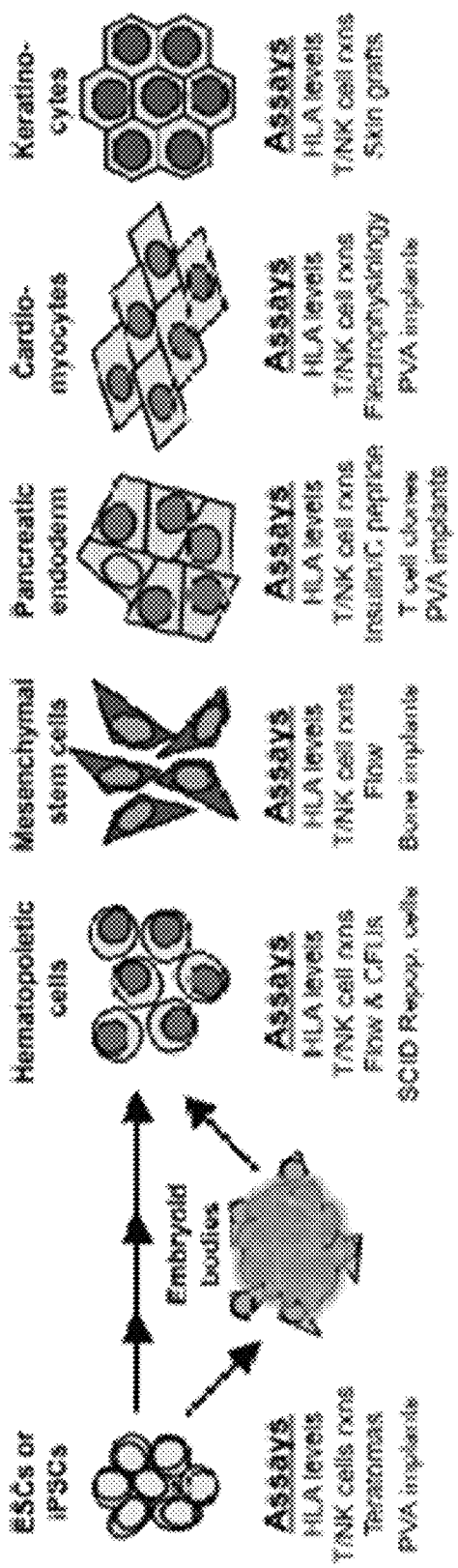
FIG. 4: outlines the experimental design for each differentiated cell type.

The cells of the invention can be differentiated into various cell types of all three lineages, including without limitation hematopoietic, mesenchymal, pancreatic endoderm, cardiac and keratinocytes cells. In certain embodiments, the differentiated cell further expresses a single chain fusion HLA class I protein. In general, each cell type can be analyzed for HLA class I protein expression, reactivity with human T cells and NK cells, appropriate differentiation markers, and xenotransplantation in immunodeficient mice to examine in vivo developmental potential. See FIG. 4. A brief discussion of each differentiated cell type follows.

In certain embodiments, the cells of the invention can be differentiated to hematopoietic cells for treating various hematopoietic diseases currently treated by bone marrow transplantation. Patients receiving transfusion can become refractory to platelet transfusions due to HLA mismatches. Anemic or cytopenic patients can be treated by delivering the cells of the invention-derived erythrocytes, platelets or neutrophils to treat bleeding or infection.

Further, stem cells of the invention-derived dendritic cells are antigen-presenting cells that can be used as cellular vaccines when properly engineered. In certain embodiments, the cells of the invention engineered to express a single chain fusion HLA class I protein and a unique peptide antigen are used to vaccinate against specific pathogen or tumor antigens. In certain other embodiments, differentiated B2M−/− cytotoxic lymphocytes with HLA-restricted reactivity against specific antigens are used to eliminate infected cells or tumor cells.

To obtain hematopoietic cells, the pluripotent cells are first allowed to form embryoid bodies, thereafter non-adherent cells were cultured in the presence of hematopoietic cytokines to develop into specific cell lineages. The differentiation of hematopoietic cells from the cells of the invention that express a single chain fusion HLA class I protein expressers can be analyzed by flow cytometry and colony assays. The different cell populations are sorted based on their surface markers, and used to monitor the expression of HLA genes and reactivity with human NK cells and T cells as measured by Elispot, mixed lymphocyte reactions, and cytotoxicity assays. The effectiveness of the single chain fusion HLA constructs on suppression of NK cell-mediated killing can be examined at different stages of differentiation and transplantation. See Bix et al., 1991, Nature 349, 329-331. The hematopoietic stem cells can also be assayed using xenotransplantation models in, for example, immunodeficient mice (SCID-repopulating cells or SRCs).

The cells of the invention can be differentiated into hematopoietic cell either before or after the cells are administered to a patient. In certain preferred embodiments, the cell is a human cell and the patient is a human. In vitro hematopoietic differentiation can be performed according to established protocols. See for example, Slukvin et al., 2006, J Immunol 176:2924-32, and Chang et al., 2006, Blood 108:1515-23.

In certain other embodiments, the cells of the invention can be differentiated into mesenchymal stem cells. In certain embodiments, the cells of the invention express one or more single chain fusion HLA class I proteins. MSCs have the potential to form several differentiated cell types, including marrow stromal cells, adipocytes, osteoblasts, and chondrocytes. Thus, inducing pluripotent stem cells to form MSCs (iMSCs) is useful in treating skeletal and joint conditions. The iMSCs can be further differentiated into osteoblasts and formed bone in vivo. Deyle et al., 2012, Mol Ther. 20(1): 204-13. Cellular responses of T cells and NK cells to ESCs, iMSCs, and their more terminally differentiated derivatives such as osteoblasts can be examined.

In certain particular embodiments, the mesenchymal stem cells are capable of differentiating into non-limiting examples of cell types such as marrow stromal cells, adipocytes, osteoblasts, osteocytes and chondrocytes. The cells of the invention are differentiated into mesenchymal stem cells either before or after the cells are administered to a patient. In certain preferred embodiments, the cell is a human cell and the patient is a human. In vitro mesenchymal differentiation can be performed according to established protocols. See for example, Deyle et al., supra.

In yet other particular embodiments, the cells of the invention can be differentiated into insulin-producing pancreatic islet cells. In certain embodiments, the cells of the invention express one or more single chain fusion HLA class I proteins. The cells of the invention can be used to treat insulin-dependent diabetes mellitus. Advantageously, the transplanted cells do not need to reconstitute a functioning pancreas: they just need to secrete insulin in response to glucose levels. Therefore the treatment can succeed with different cell doses, with cells that are not perfectly differentiated into adult cell types, and when cells are transplanted into an ectopic location. Specific auto-antigens such as those derived from GAD65 or Insulin can cause autoimmune destruction of β cells in diabetes (Di Lorenzo et al., 2007, Clin Exp Immunol 148, 1-16). Thus, B2M−/− cells or B2M−/− cells expressing a single chain fusion HLA class I protein presenting a predetermined peptide antigen provide additional advantages in that they do not present these auto-antigens and can avoid autoimmune rejection and prevent a relapse of diabetes after transplantation.

The cells of the invention can be differentiated into pancreatic cells as described previously, which employs exposure of cells to different cytokines and drugs to promote sequential formation of mesendoderm, definitive endoderm, and pancreatic progenitors (Kroon et al., 2008, Nat Biotechnol 26, 443-452). These cells can be further cultured in implants in immunodeficient mice. The cells of the invention with or without expressing a single chain fusion HLA class I protein and wild-type cell lines can be analyzed at different developmental stages for their reactivity with T cells and NK cells.

The cells of the invention are differentiated into pancreatic islet cell either before or after patient administration. In certain preferred embodiments, the cell is a human cell and the patient is a human. In vitro hematopoietic differentiation can be performed according to established protocols. See for example, Kroon et al., 2008, Nat Biotechnol 26, 443-452.

In certain other particular embodiments, the cells of the invention can be differentiated into cardiomyocytes. In certain embodiments, the cells of the invention further express one or more single chain fusion HLA class I proteins. The common clinical problems of myocardial infarction and congestive heart failure can be treated by transplanting healthy stem cell-derived cardiomyocytes that engraft and re-establish functional myocardium. The cells of the invention-derived cardiomyocytes allow these treatments to proceed with pre-packaged cells and avoid the immunosuppression currently required for allogeneic heart transplants. Physiologically relevant tests can be performed on the cardiomyocytes derived from the cells of the invention, such as electrical conduction and contraction studies. B2M−/− stem cells or differentiated cardiomyocytes with or without expressing a single chain fusion HLA class I protein can be tested to determine their immunological reactivity when expressing cardiomyocyte genes, and to establish which HLA modifications minimize these immune responses.

The cells of the invention can be differentiated into cardiomyocytes either before or after the cells are administered to a patient. In certain preferred embodiments, the cell is a human cell and the patient is a human. In certain embodiments, the cells of the invention are differentiated into cardiomyocytes for treating diseases including without limitation myocardial infarction and congestive heart failure. In vitro cardiomyocyte differentiation can be performed according to established protocols. See for example, Laflamme et al., 2007, Nat Biotechnol 25, 1015-1024.

Figure 5:
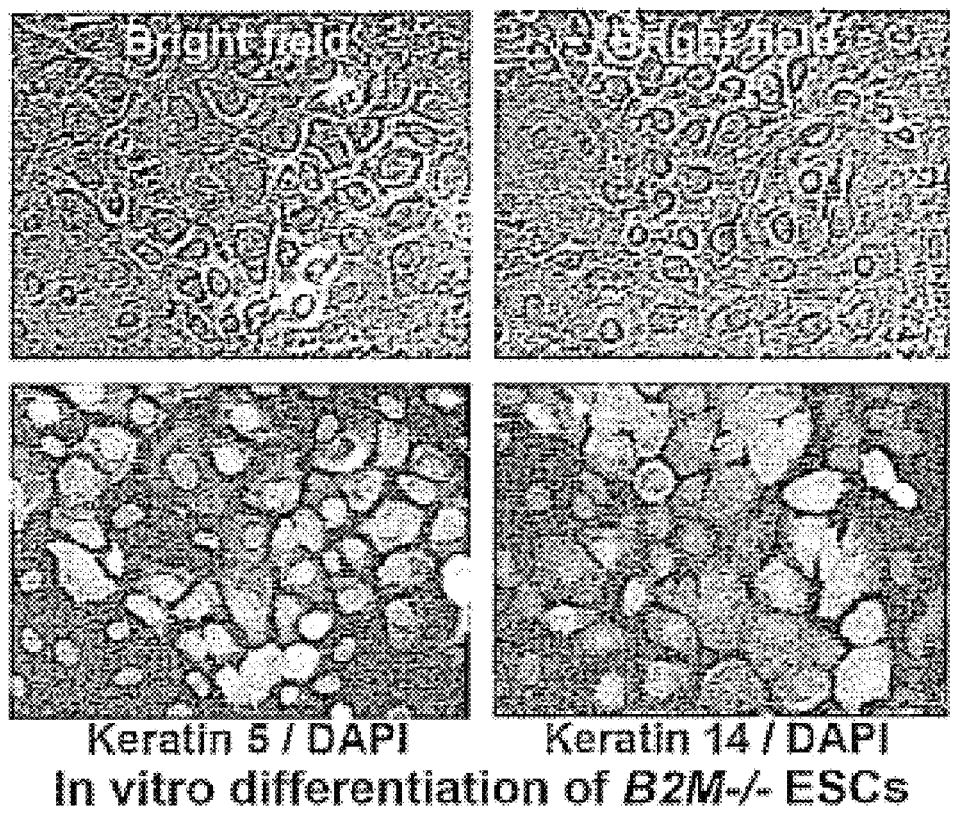
FIG. 5: shows differentiation of keratinocytes from B2M–/– ESCs.

In yet other particular embodiments, the cells of the invention can be differentiated into keratinocytes. In certain embodiments, the cells of the invention used for differentiation into keratinocytes express one or more single chain fusion HLA class I proteins. Severe burns and genetic skin conditions require treatment with skin grafts, and this is currently done with a variety of cell sources such as porcine skin grafts and cultured autologous human keratinocytes. Keratinocytes derived from the cells of the invention can provide a major clinical advance, since burns could be treated as an emergency with pre-packaged cells, and genetic diseases such as epidermolysis bullosum can be treated with normal cells (albeit with the B2M−/− background in the cellular chromosome) that do not require correction of the responsible genetic mutations. In many cases the cells only need to engraft long enough for neighboring host cells to repopulate the affected area. FIG. 5 shows in vitro differentiation of Keratin 5+ and Keratin 14+ keratinocyte colonies from the cells of the invention. The cells of the invention were cultured in matrigel cultures, followed by expansion in serum-free keratinocyte medium containing all-trans retinoic acid and BMP4 as described previously (Itoh et al., 2011, PNAS USA 108, 8797-8802). For in vivo differentiation, the cells of the invention can be embedded in polyvinyl alcohol sponge (PVA)-collagen gel implants for transplantation into a recipient. The cells of the invention can be differentiated into keratinocytes either before or after transplantation. In certain preferred embodiments, the cell is a human cell and the patient is a human.

In yet another aspect, the invention provides a use of the cells of the invention for the preparation for a medicament for transplantation. In a related aspect, the invention provides a use of the cells of the invention for the preparation for a medicament for treating a disease condition.

Further, the cells of the invention can serve as a research tool to provide a system for studying the functions of immunoregulatory proteins in a B2M−/− genetic background. In certain embodiments, the cells of the invention further express one or more single chain fusion HLA class I proteins. Accordingly, in a related aspect, the invention provides a method of determining the function of an immunoregulatory protein comprising the steps of introducing one or more immunoregulatory genes into the cells of the invention of the invention and assaying for the activities of the immunoregulatory genes. In certain preferred embodiments, the cell is a human cell. For example, the cells of the invention can be used to study the function of an immune regulatory gene, or to study an immune response, in the absence of unwanted class I antigens. In certain embodiments, the cells of the invention express HLA-F or a single chain fusion HLA class I protein comprising B2M and HLA-F, wherein the function of the HLA-F can be studied in the B2M−/− background. In a further related aspect, the invention provides a method of identifying a compound or molecule that modulates the function of the immunoregulatory protein comprising the steps of contacted the B2M−/− cells comprising the one or more immunoregulatory genes with a compound or molecule of interest and assaying for the activities of the immunoregulatory genes. In certain preferred embodiments, the cell is a human cell.

In yet another related aspect, the invention provides an in vivo research tool in a mammal, particular in a non-human primate, that are administered the cells of the invention, for studying the functions of immunoregulatory genes, or identifying a compound that modulates the function of an immunoregulatory gene in the administered cells in a B2M−/− genetic background. In certain embodiments, the cells of the invention further express one or more single chain fusion HLA class I proteins.

Mice, especially immune deficient mice, have been used as a model system for studying human cells in vivo. Human stem cells can behave differently in mice. In addition, the mouse and human immune systems have different NK cell receptors and non-classical MHC class I genes (e.g. HLA-E, F and G). Therefore, a *Macaca nemestrina* (Mn, pigtailed macaque) model can be developed to study the cells of the invention. The *Macaca mulatta* genome has been sequenced, which is highly homologous to the *nemestrina* genome. Further, the organization of macaque MHC loci is similar to human HLA, including the non-classical genes. Homologs of the human HLA-E and HLA-G genes have been identified in macaques. The macaque MHC loci also contain homologs of many human NK cell receptors. Human B2M−/− ESCs as well as Mn B2M−/− ESCs can be used for transplantation in macaques.

MHC class I-deficient (B2M−/−) macaque ESCs can be developed using the same AAV-mediated gene targeting strategy described for human cells. Mn versions of the single-chain HLA class I fusion proteins are expressed in the B2M−/− macaques ESCs using the analogous viral vectors as described above.

Cells can be expanded in vitro and labeled with a vector expressing GFP for subsequent identification of transplanted cells. The cells can be embedded in polyvinyl alcohol sponge (PVA)-collagen gel implants, and placed subdermally into macaques. The implants can be harvested, sectioned and stained to determine the cell types that are present. Specific antibodies can be used to identify the differentiated cell types formed by the transplanted cells.

Any and every embodiment described above applies to any and every aspect of the invention, unless the context clearly indicates otherwise. All embodiments within and between different aspects can be combined unless the context clearly dictates otherwise.

The Examples, which follow, are illustrative of specific embodiments of the invention, and various uses thereof. They are set forth for explanatory purposes only, and are not to be taken as limiting the invention.

EXAMPLES

Example 1 Construction of Human Pluripotent Stem Cells with Knockout Mutations in B2M Genes Human pluripotent stem cells were created with knockout mutations in both alleles of the beta-2 microglobulin (B2M) genes that encodes the common subunit required for surface expression of all HLA class I heterodimers (HLA-A, B, C, E, F and G). Adeno-associated virus (AAV) gene targeting vectors were used to construct B2M−/− (class I-negative) H1 human ESCs (University of Wisconsin). Human pluripotent stem cells were infected with AAV gene targeting vectors and the B2M gene was inactivated by homologous recombination. AAV mediated gene targeting methodology has been described previously in for example, Khan et al., 2011, Protocol, 482:482-501 and Khan et al., 1990, Science 248:1227-30. These references are hereby incorporated by reference in their entirety.

FIG. 1 describes the construction of HLA class I-negative human H1 ESCs cells using the adeno-associated virus (AAV) gene targeting vectors. The two AAV vectors used contain homologous arms surrounding exon 1 of the human B2M gene, and are designed to insert either a TKNeo or HyTK fusion gene encoding G418 or hygromycin resistance respectively into exon 1 (FIG. 1A). The H1 ESCs were infected with the AAV-B2M-ETKNpA vector and 30% of G418-resistant cells were targeted at one B2M allele based on Southern blot analysis. One of these clones was then infected with the AAV-B2M-EHyTKpA vector and 10% of hygromycin-resistant cells were targeted at B2M. Southern blot analysis of a representative clone that had deletions in both B2M alleles (B2M-/-) is shown in FIG. 1B (HyTK/TKN). None of the targeted clones analyzed contained random integrants. The sequences of the targeting vector plasmid pA2-B2METKMpA and pA2-B2MEHuTKpA are shown in SEQ ID NO:21 and SEQ ID NO:22, respectively.

Cre recombinase was then used to remove the foxed TKNeo and HyTK transgenes from the B2M loci. Cre was delivered transiently by a non-integrating foamy virus vector, which is a type of retroviral vector previously described that efficiently infects human ESCs. See Deyle, et al., 2010, J. Virol 84, 9341-9 and Gharwan et al., 2007, Mol Ther 15, 1827-1833. Four clones lacking the TKNeo and HyTK transgenes were selected by gancyclovir section that kills cells expressing thymidine kinase (TK). The results shown by Southern blot analysis demonstrated transgene-free double knockouts (FIG. 1B).

Karyotypes were checked on two of these clones and found to be normal (data not shown), and teratoma assays conducted in immunodeficient mice showed that these cells had trilineage developmental potential (FIG. 2). Flow cytometry with antibodies against B2M (anti-B2M-01-PE from SantaCruz Biotechnology) and pan-HLA class I antigens (W6/32 from Sigma-Aldrich) confirmed that these cells did not express HLA class I proteins on the cell surface (FIG. 1C).

Example 2 Expression of Single Chain Fusion HLA Class I Proteins in B2M Knockout Cells In mice, HLA class I-negative cells can be destructed by Natural Killer (NK) cells through the "missing self" mechanism. Bix et al., 1991, Nature 349, 329-331. Human NK cells have different receptors, but an analogous inhibition of NK cell killing is mediated through interactions of NK cell receptors with HLA-C, E and G. The "missing self" phenomenon has largely been described for class I-deficient hematopoietic cells, and the mouse transplantation data reported previously showing that many types of B2M-/- organs survived in B2M+/+ hosts suggests that it may be less important when transplanting cells form solid organs. However, given that it could significantly affect donor cell survival in some settings, specific HLA class I genes as single chain fusion proteins that suppress NK cell killing were introduced to the B2M-/- cells.

The strategy for expressing specific HLA class I genes in a B2M-/- background is shown in FIG. 3. The B2M chain was fused to the specific HLA class I heavy chain, thereby allowing surface expression of the class I chain even in B2M-/- cells. Integrating foamy virus vectors were used to express these single chain fusion proteins. Foamy virus vectors are a type of retroviral vector with a large packaging capacity that can efficiently infect human pluripotent stem cells (Gharwan at al., supra). One such representative single chain fusion HLA class I protein foamy virus construct is shown in FIG. 3A. The ΔΦ-EGP-PHLA-SC foamy vectors included a GFP-euro fusion protein gene driven by an EF1 alpha promoter to allow for puromycin selection and GFP expression in transduced cells, and a separate expression cassette with a ubiquitously expressed PGK promoter driving an HLA single chain fusion (HLA-SC) construct (FIG. 3A). The vector design produced constitutive expression of both transgenes, but many other vector designs and internal promoters can also be used. For example, the GFP-Pur gene can be driven by the pGK promoter, and the EF1alpha promoter controls the expression of the SC HLA gene.

As shown in FIG. 3B, the HLA-bGBE trimeric single chain fusion construct included a covalently attached HLA-G peptide (SEQ ID NO:23) in the HLA-E peptide binding cleft, while the HLA-gBE dimeric construct included an HLA-G signal peptide that was cleaved off but still bound non-covalently to the HLA-E molecule. See Crew et al., 2005, Mol Immunol 42, 1205-1214. B2M-/- cells were transduced with these vectors. Puromycin-resistant clones were selected and HLA-E surface expression was analyzed by flow cytometry in pluripotent cells expressing these constructs (FIG. 3C).

Further, a specific classical HLA class I allele single chain fusion protein was constructed and expressed in B2M-/- H1 ESCs to create a "semi-universal" donor cell to facilitate compatibility with recipients. For example, in the U.S. the HLA-A0201 allele is present in 48% of Caucasians, 46% of Hispanics, and 24% of African-Americans, all of which should accept HLA-A0201+ stem cells. See www.allelfrequencies.net and Storkus et al., 1989, PNAS USA 86:2361-2364. The HLA-bBA0201 dimeric single chain fusion construct was introduced in B2M-/- H1 ESCs by foamy virus vectors (FIG. 3B) and the expression of the single chain fusion protein was analyzed by flow cytometry (FIG. 3D).

It should be understood that the foregoing disclosure emphasizes certain specific embodiments of the invention and that all modifications or alternatives equivalent thereto are within the spirit and scope of the invention as set forth in the appended claims.

What is claimed is:

1. An isolated human cell comprising
   (a) a genetically engineered disruption of the endogenous beta-2 microglobulin (B2M) gene,
   (b) one or more polynucleotides capable of encoding a single chain fusion non-classical human leukocyte antigen (HLA) class I protein, wherein the single chain fusion non-classical HLA class I protein comprises at least a portion of B2M protein covalently linked to at least a portion of an HLA-E class I α chain;
   wherein the single chain fusion non-classical HLA I protein is capable of normal function with respect to engaging the inhibitory receptors on the surface of NK cells.

2. The cell of claim 1, wherein the cell comprises genetically engineered disruptions in all copies of the endogenous cell B2M gene.

3. The cell of claim 1, wherein the cell further comprises a peptide that is presented by the single chain fusion non-classical HLA-E class I protein on the cell surface.

4. The cell of claim 1, wherein the at least a portion of B2M protein covalently linked to at least a portion of an HLA-E class I α chain is a full-length B2M protein.

5. The cell of claim 1, wherein the at least a portion of B2M protein and the at least a portion of an HLA-E class I α chain in the single chain fusion non-classical HLA class I protein are linked via a linker sequence.

6. The cell of claim 1, wherein the B2M protein of the single chain fusion non-classical human leukocyte antigen (HLA) class I protein lacks a leader sequence.

7. The cell of claim 1, wherein the HLA-E class I α chain lacks a leader sequence.

8. The cell of claim 1, wherein the cell has a normal karyotype.

9. The cell of claim 1, wherein the cell is a non-transformed cell.

10. The cell of claim 1, wherein the cell is a stem cell.

11. The cell of claim 10, wherein the stem cell is selected from the group consisting of a pluripotent stem cell, a hematopoietic stem cell, an embryonic stem cell, an induced pluripotent stem cell, an adult stem cell, a liver stem cell, a neural stem cell, a pancreatic stem cell and a mesenchymal stem cell.

12. The cell of claim 11, wherein the stem cell is a pluripotent stem cell.

13. The cell of claim 1, wherein the cell is a differentiated cell.

14. The cell of claim 13, wherein the differentiated cell is selected from the group consisting of a dendritic cell, a pancreatic islet cell, a liver cell, a muscle cell, a keratinocyte, a neuronal cell, a hematopoietic cell, a lymphocyte, a red blood cell, a platelet, a skeletal muscle cell, an ocular cell, a mesenchymal cell, a fibroblast, a lung cell, a GI tract cell, a vascular cell, an endocrine cell, an adipocyte, a marrow stromal cell, an osteoblast, a chrondrocyte, and a cardiomyocyte.

15. A pharmaceutical composition comprising the cell of claim 13 and a physiologically compatible buffer.

16. A kit comprising the cell of claim 13.

* * * * *